US009920377B2

(12) United States Patent
Kashani-Sabet et al.

(10) Patent No.: US 9,920,377 B2
(45) Date of Patent: Mar. 20, 2018

(54) FALZ FOR USE AS A TARGET FOR THERAPIES TO TREAT CANCER

(71) Applicant: Sutter West Bay Hospitals, San Francisco, CA (US)

(72) Inventors: Mohammed Kashani-Sabet, San Francisco, CA (US); Altaf A. Dar, San Bruno, CA (US)

(73) Assignee: SUTTER WEST BAY HOSPITALS, San Francisco, CA (US)

( * ) Notice: Subject to any disclaimer, the term of this patent is extended or adjusted under 35 U.S.C. 154(b) by 143 days.

(21) Appl. No.: 14/775,665

(22) PCT Filed: Mar. 15, 2014

(86) PCT No.: PCT/US2014/029986
§ 371 (c)(1),
(2) Date: Sep. 11, 2015

(87) PCT Pub. No.: WO2014/145254
PCT Pub. Date: Sep. 18, 2014

(65) Prior Publication Data
US 2016/0024590 A1 Jan. 28, 2016

Related U.S. Application Data

(60) Provisional application No. 61/790,153, filed on Mar. 15, 2013.

(51) Int. Cl.
| | | |
|---|---|---|
| C12Q 1/68 | (2006.01) | |
| A61K 45/00 | (2006.01) | |
| A61P 35/00 | (2006.01) | |
| C12N 15/113 | (2010.01) | |
| A61K 48/00 | (2006.01) | |
| G01N 33/574 | (2006.01) | |
| G01N 33/68 | (2006.01) | |
| A61K 31/7105 | (2006.01) | |
| A61K 45/06 | (2006.01) | |

(52) U.S. Cl.
CPC ........ C12Q 1/6886 (2013.01); A61K 31/7105 (2013.01); A61K 45/06 (2013.01); A61K 48/00 (2013.01); C12N 15/113 (2013.01); G01N 33/5743 (2013.01); G01N 33/57407 (2013.01); G01N 33/6872 (2013.01); C12N 2310/11 (2013.01); C12N 2310/14 (2013.01); C12Q 2600/118 (2013.01); C12Q 2600/158 (2013.01)

(58) Field of Classification Search
CPC ...................................... A61P 35/00

USPC ............ 424/174.1; 435/6.1, 6.11, 6.12, 91.1, 435/91.31, 455, 458; 514/44; 536/23.1, 536/24.5
See application file for complete search history.

(56) References Cited

U.S. PATENT DOCUMENTS

| | | | | |
|---|---|---|---|---|
| 2010/0130527 | A1* | 5/2010 | Lehrer | .................. G06F 19/20 514/291 |
| 2010/0145131 | A1 | 6/2010 | Grinberg-Rashi et al. | |
| 2011/0119776 | A1 | 5/2011 | Wong et al. | |
| 2011/0287020 | A1* | 11/2011 | Gruber | ............... A61K 38/2292 424/155.1 |
| 2015/0154345 | A1* | 6/2015 | Jones | ..................... C40B 30/02 514/238.8 |
| 2015/0337388 | A1* | 11/2015 | Garner, Jr. | .......... C12Q 1/6886 506/8 |
| 2016/0078168 | A1* | 3/2016 | Zhuo | ..................... G06F 19/22 506/9 |

FOREIGN PATENT DOCUMENTS

WO 2012055879 A1 5/2012

OTHER PUBLICATIONS

Buganim et al, PLoS One, vol. 5, No. 3, e9657, pp. 1-12 (2010)).*
Ramaswamy, et al., "A Molecular signature of metastasis in primary solid tumors," Nat Genet, Jan. 2003, vol. 33, No. 1, pp. 49-54.
Young, Lee W., International Search Report and Written Opinion, International Application No. PCT/US2014/029986, dated Oct. 27, 2014.
Angioni, C.F., Extended European Search Report, EP Application No. 14764616, dated Sep. 27, 2016.
De Semir et al., "Pleckstrin homology domain-interacting protein (PHIP) as a marker and mediator of melanoma metastasis", Proceedings of the National Academy of Sciences, vol. 109, No. 18, Apr. 17, 2012, pp. 7067-7072.
Grinberg-Rashi et al., "The Expression of Three Genes in Primary Non-Small Cell Lung Cancer is Associated with Metastatic Spread to the Brain", Clinical Cancer Research, vol. 15, No. 5, Feb. 17, 2009, pp. 1755-1761.
White Kristen et al., "Expression of BRCA1 and FAC1 in primary sporadic breast cancers", Database Accession No. PREV201200748670 and FASEB Journal, vol. 22, Apr. 22, 2008.

(Continued)

Primary Examiner — Jane J Zara
(74) Attorney, Agent, or Firm — Gavrilovich, Dodd & Lindsey LLP

(57) ABSTRACT

The disclosure provides methods for predicting and/or determining whether a subject has cancer based on the level of expression of BPTF. The disclosure also provides methods for determining whether a cancer in a subject is progressing or regressing based upon the change of expression levels of BPTF between two time points. The disclosure further provides methods to treat a subject with a cancer by administering a polynucleotide comprising an inhibitory BPTF nucleic acid and/or an agent that inhibits the expression or activity of BPTF.

7 Claims, 21 Drawing Sheets

(56) References Cited

OTHER PUBLICATIONS

Becamel, Philippe, International Preliminary Report on Patentability and Written Opinion, International Application No. PCT/US2014/029986, dated Sep. 24, 2015.

* cited by examiner

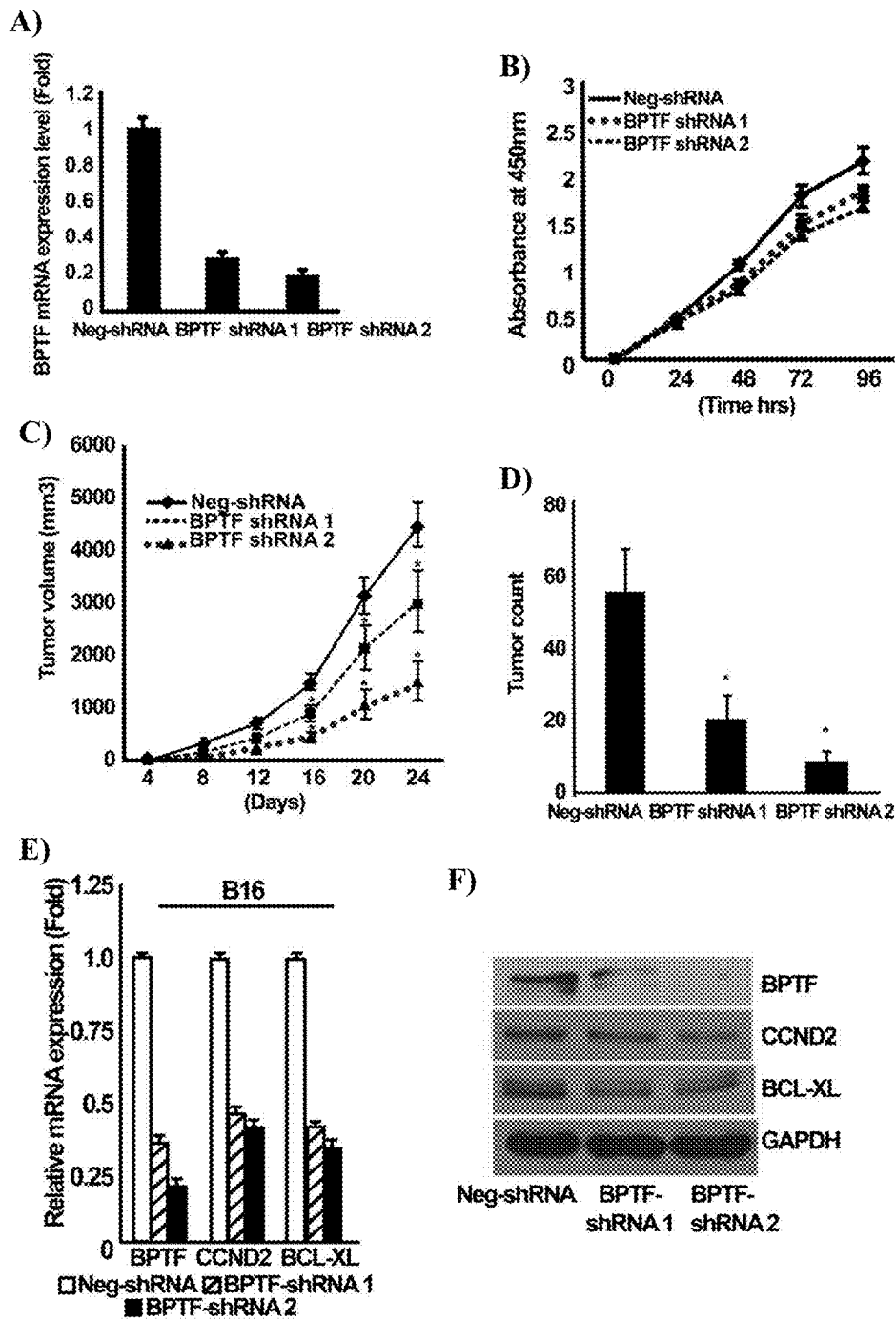
FIGURE 1A-F

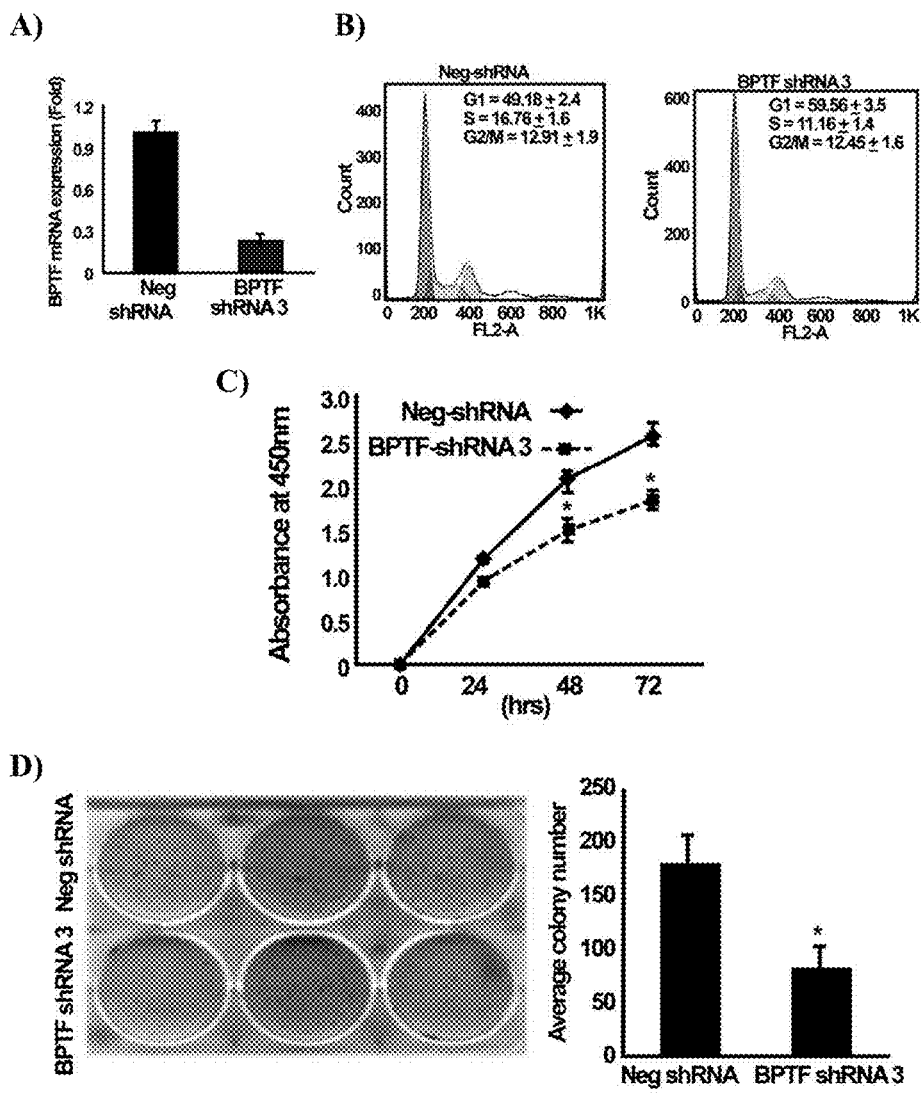
Figure 2A-D

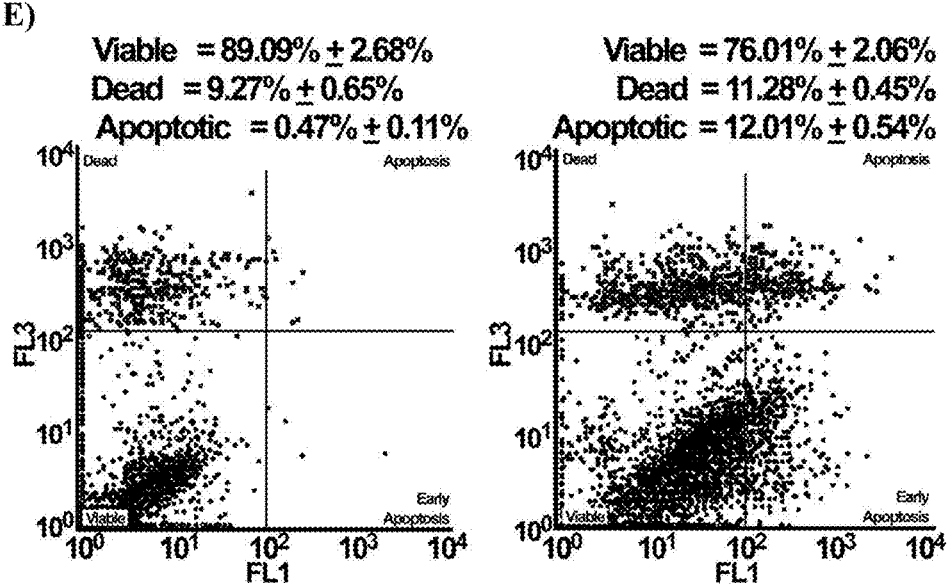
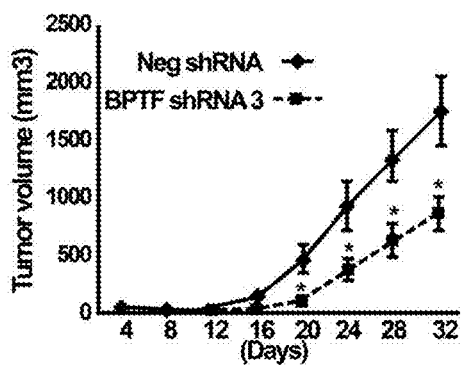
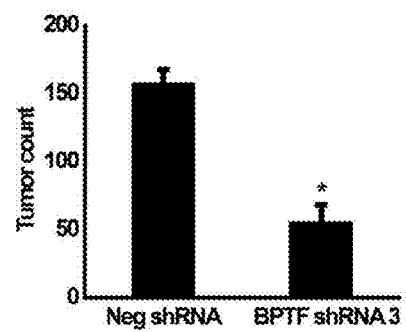
Figure 2E-G

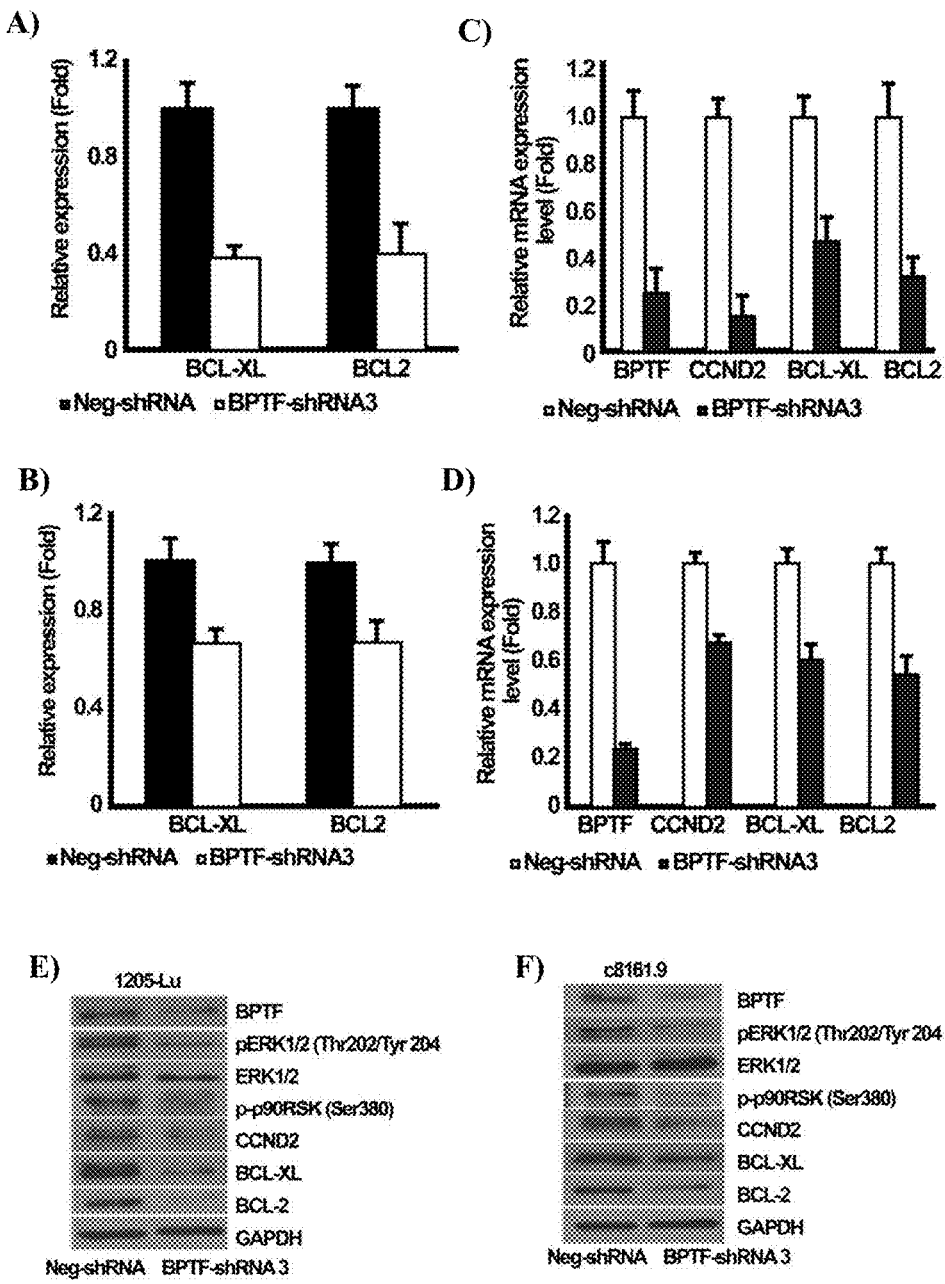
Figure 3A-F

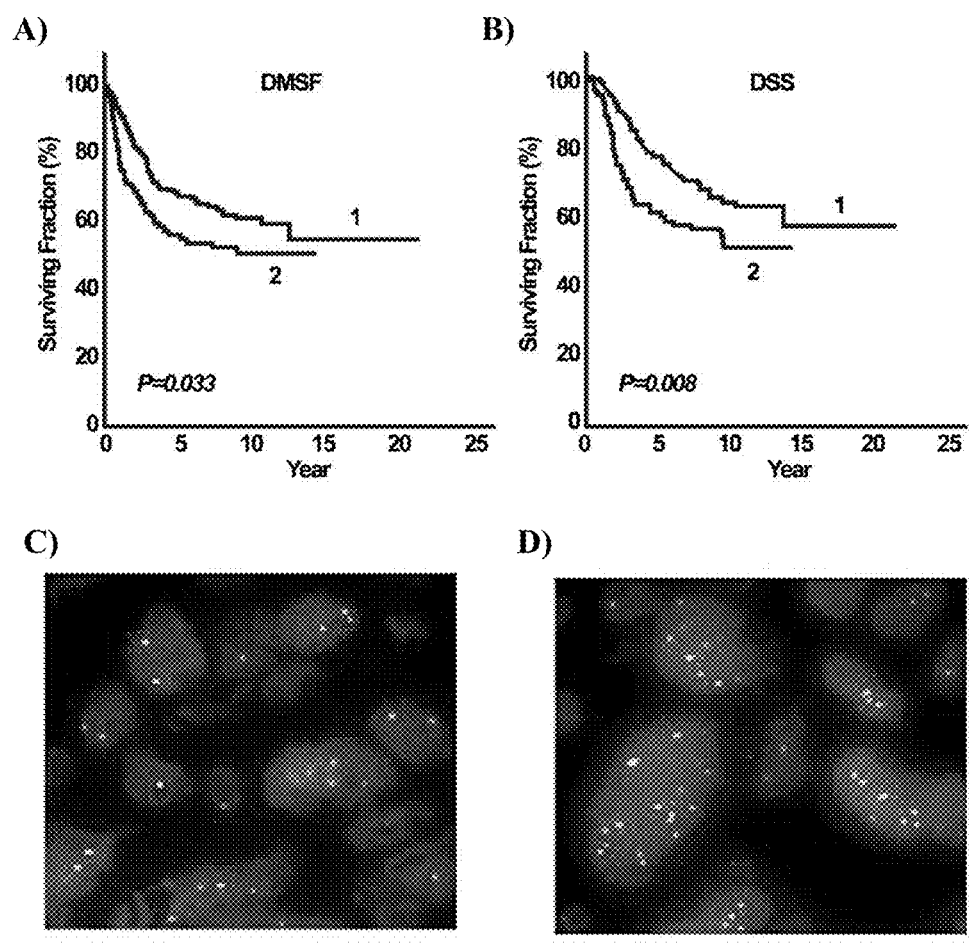
Figure 4A-D

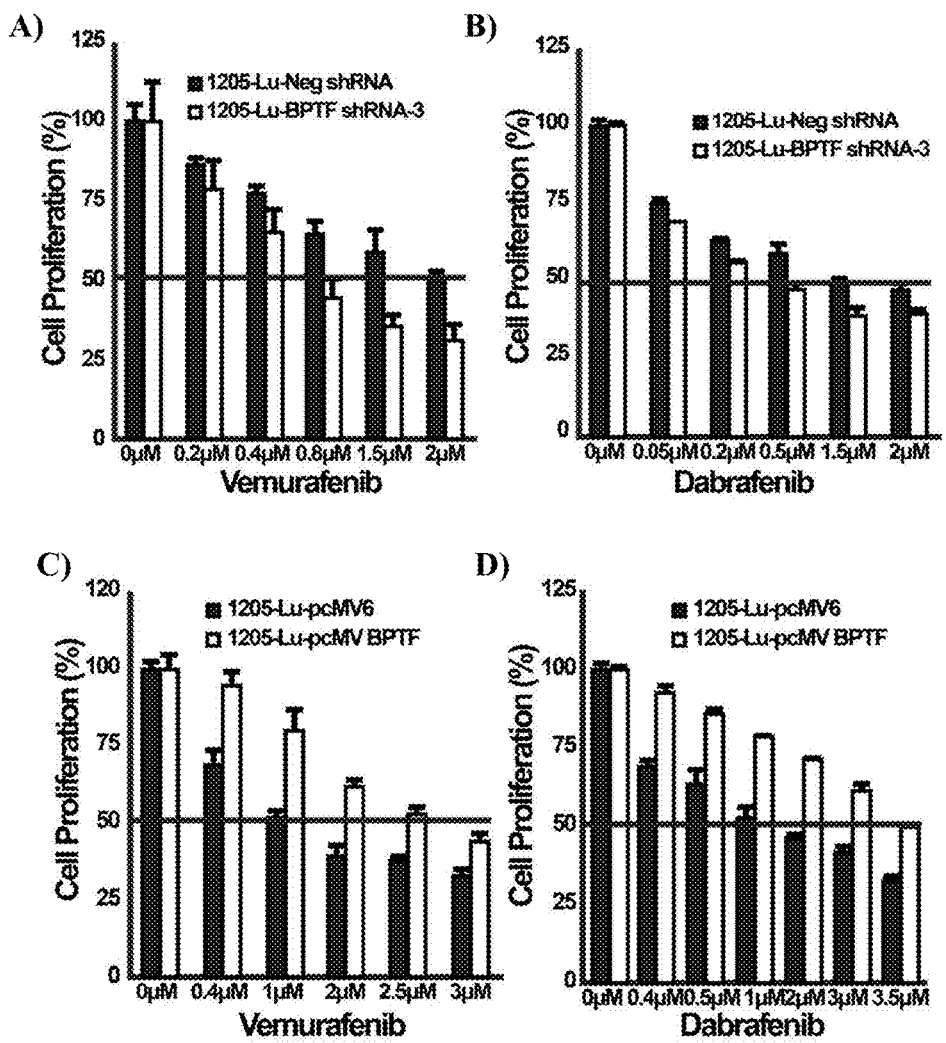
Figure 5A-D

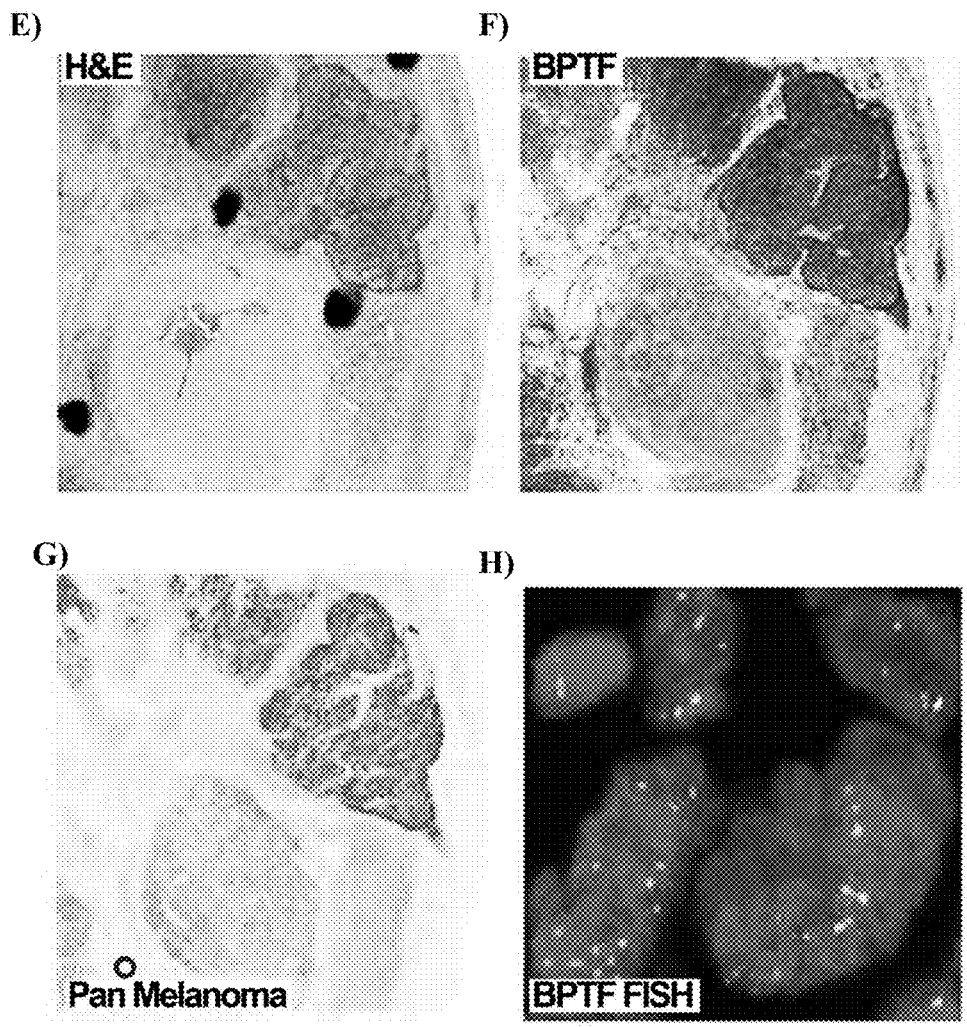
Figure 5E-H

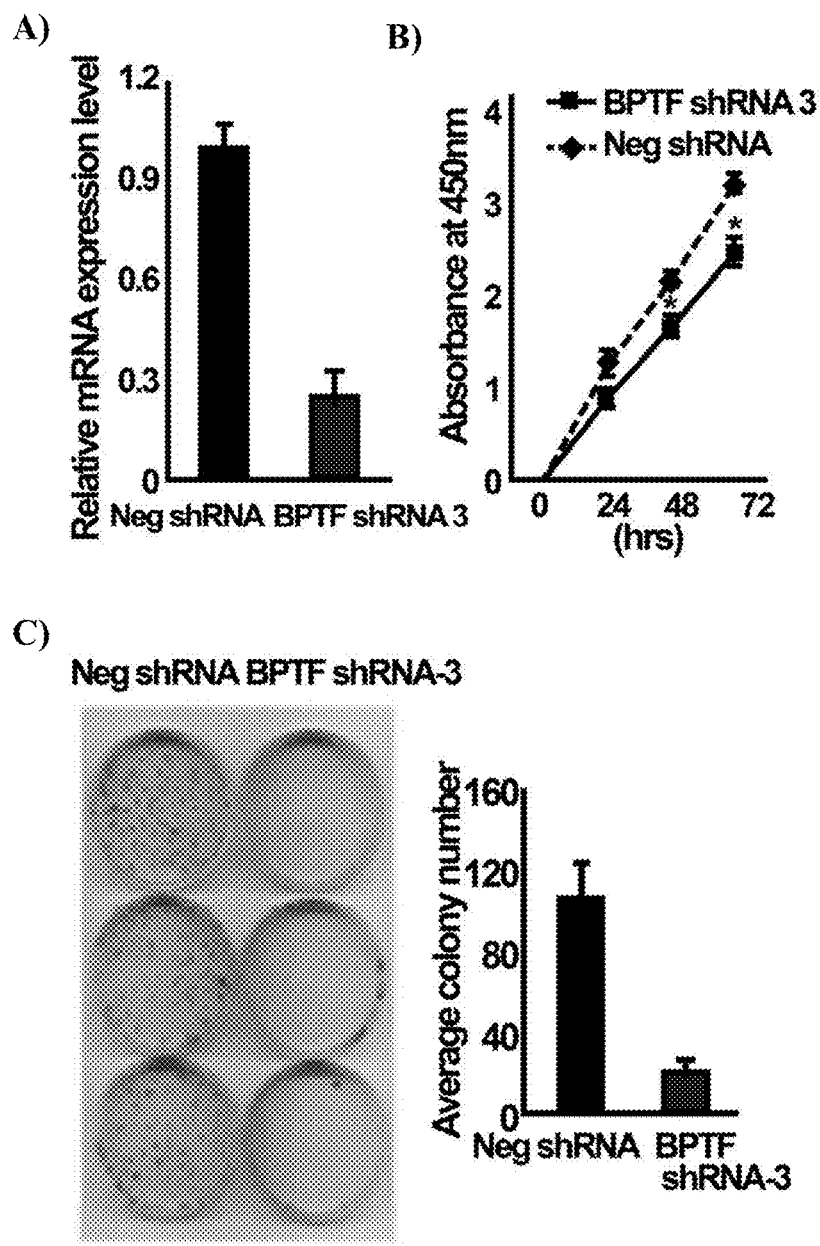
Figure 6A-C

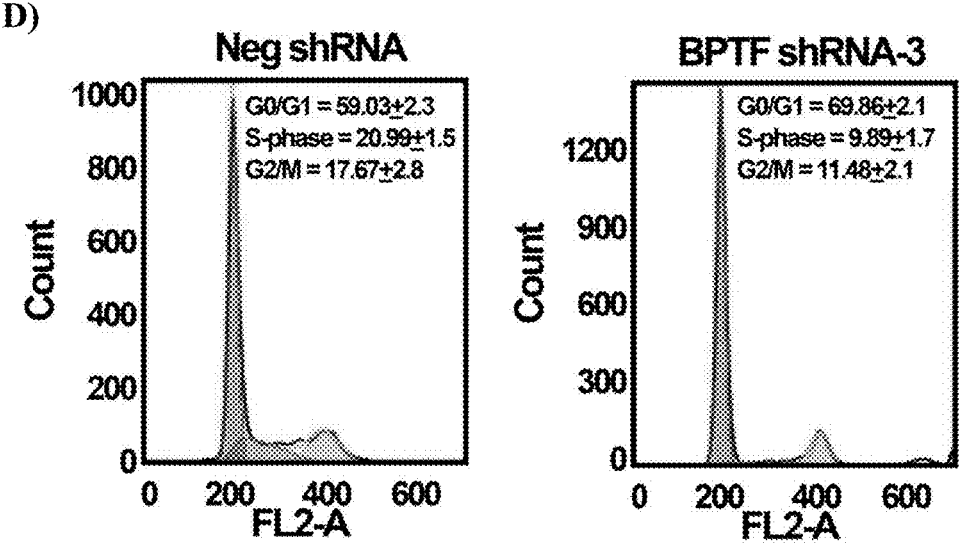
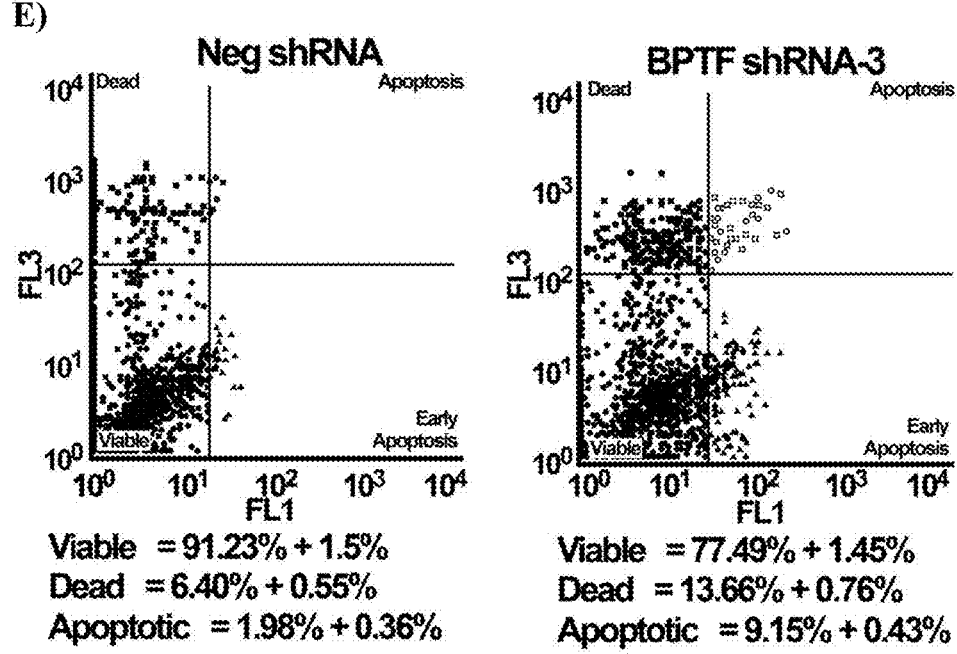
Figure 6D-E

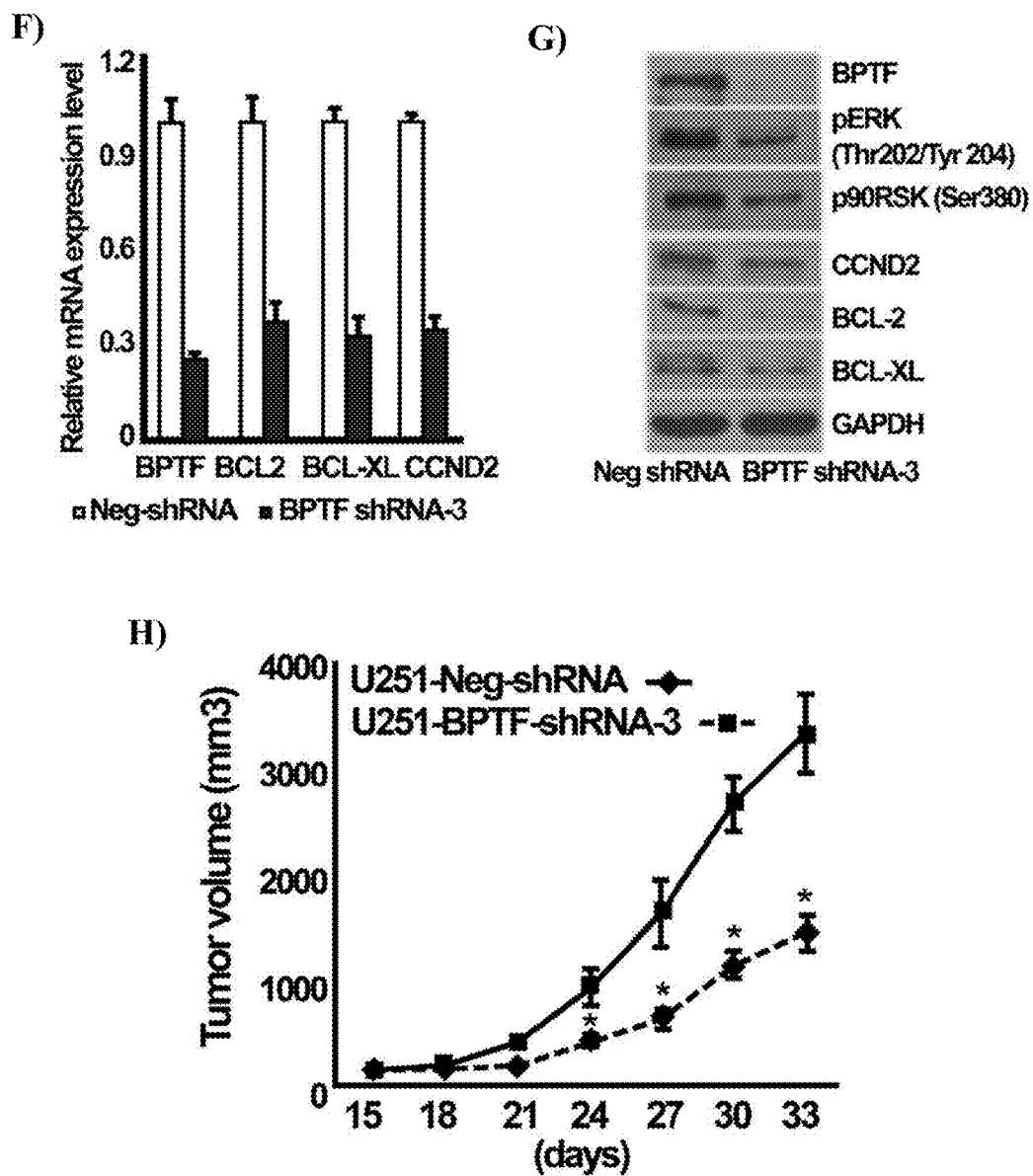
Figure 6F-H

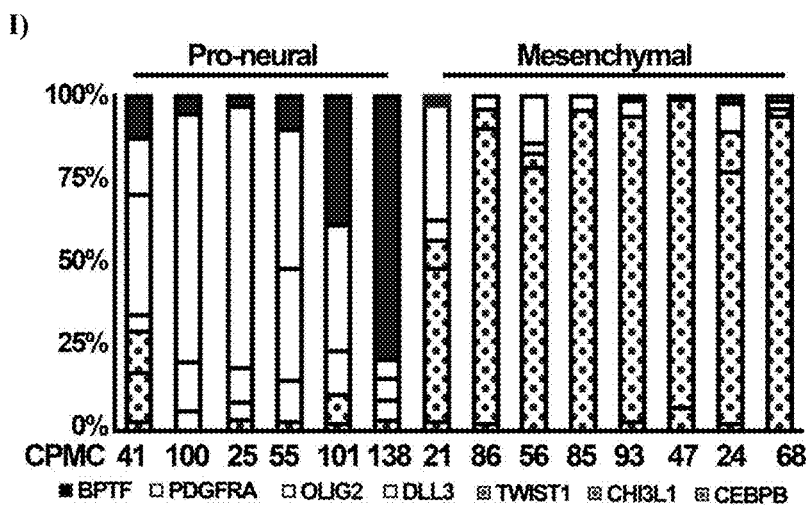
Figure 6I
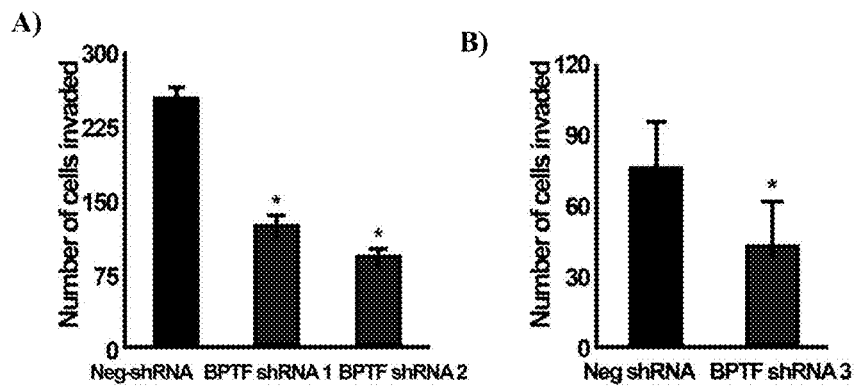
Figure 7A-B

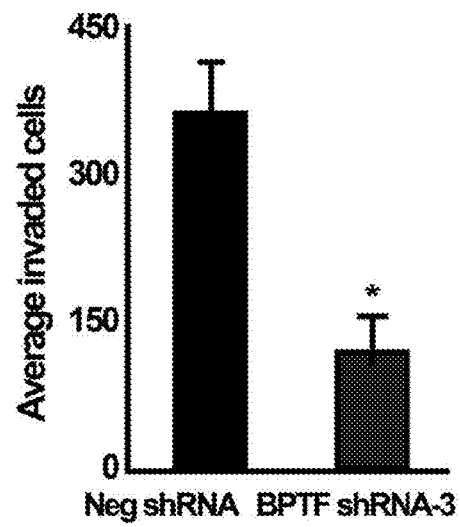
Figure 7C
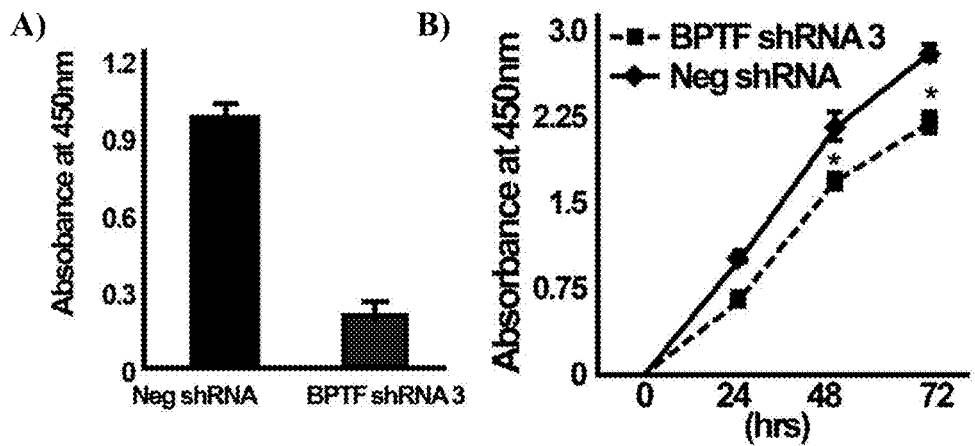
Figure 8A-B

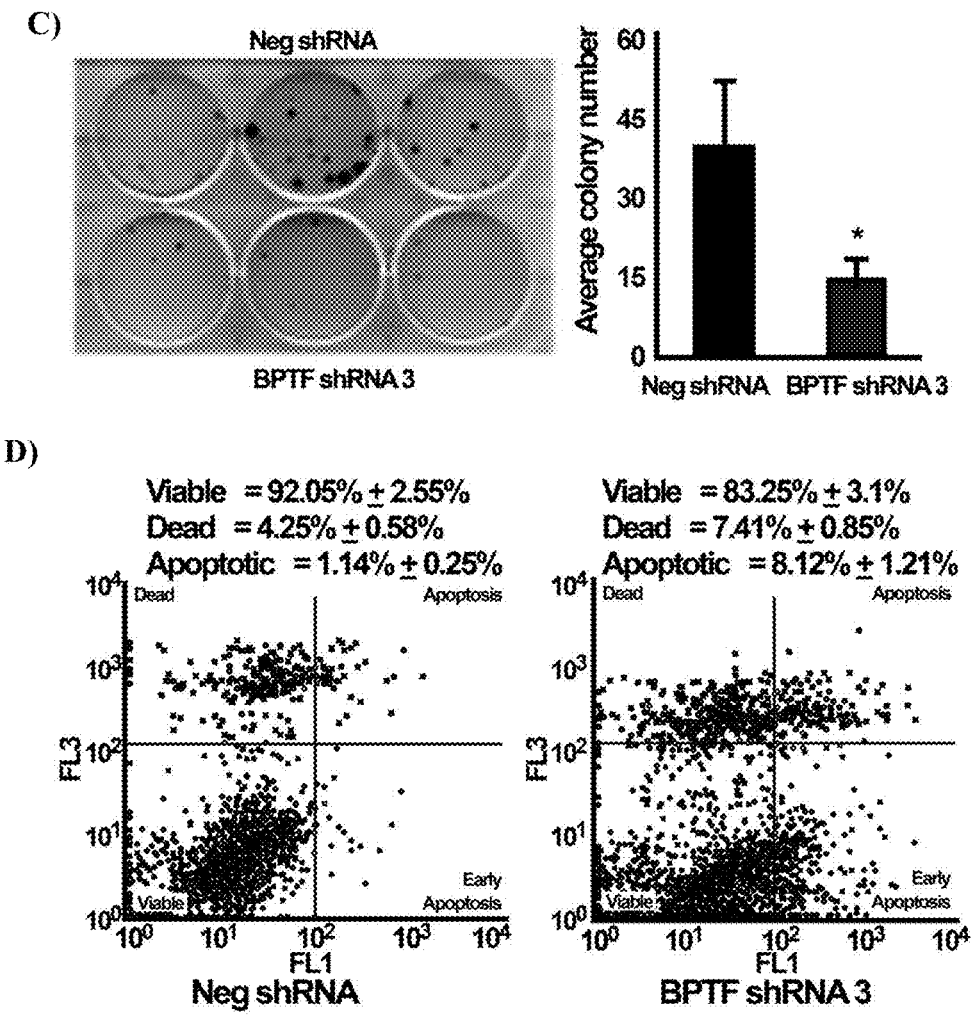
Figure 8C-D

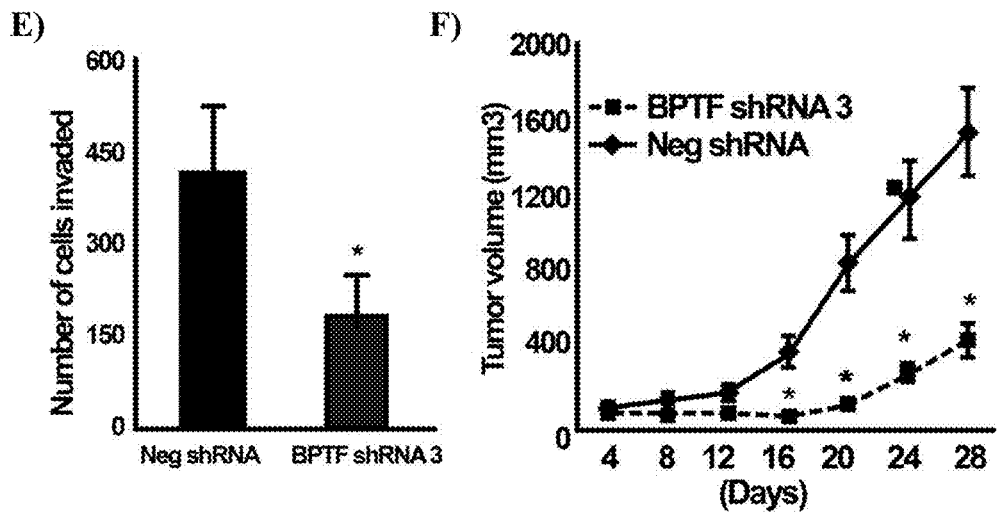
Figure 8E-F
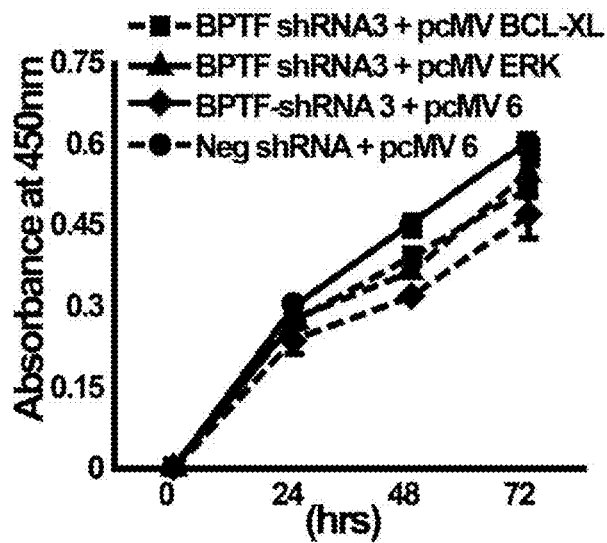
FIGURE 9

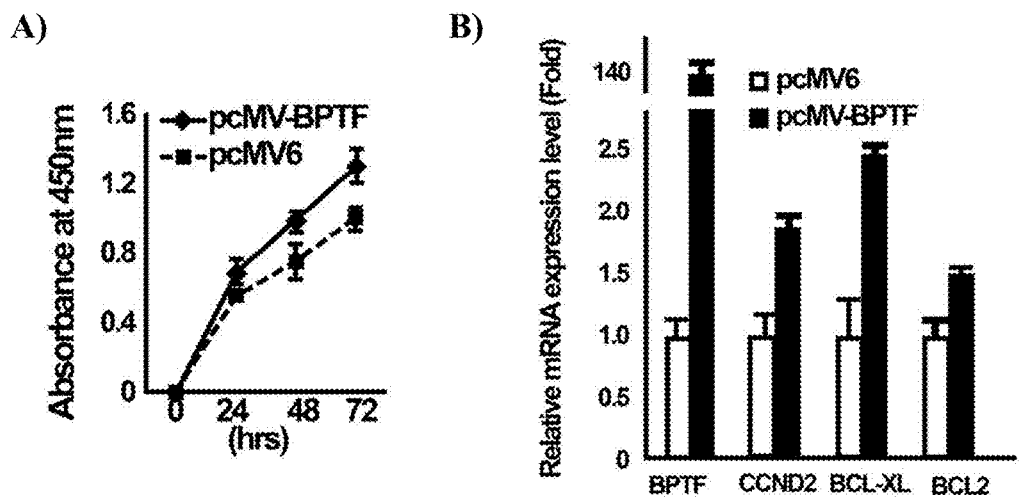
Figure 10A-B
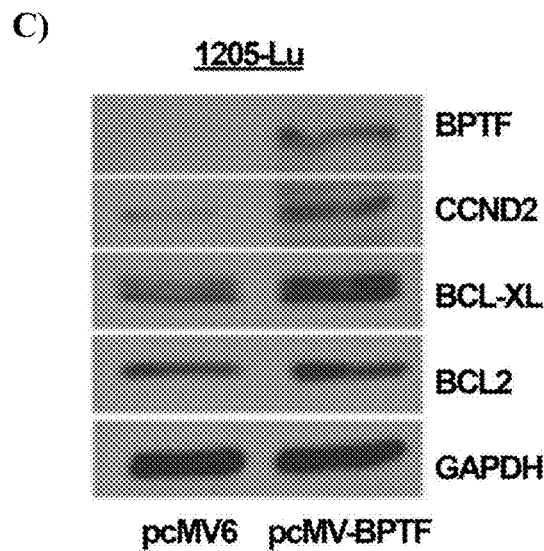
FIGURE 10C

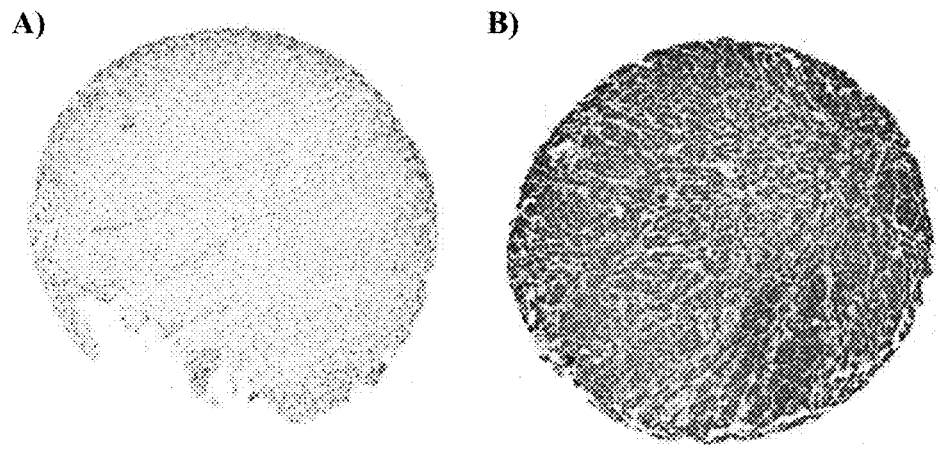
FIGURE 11A-B
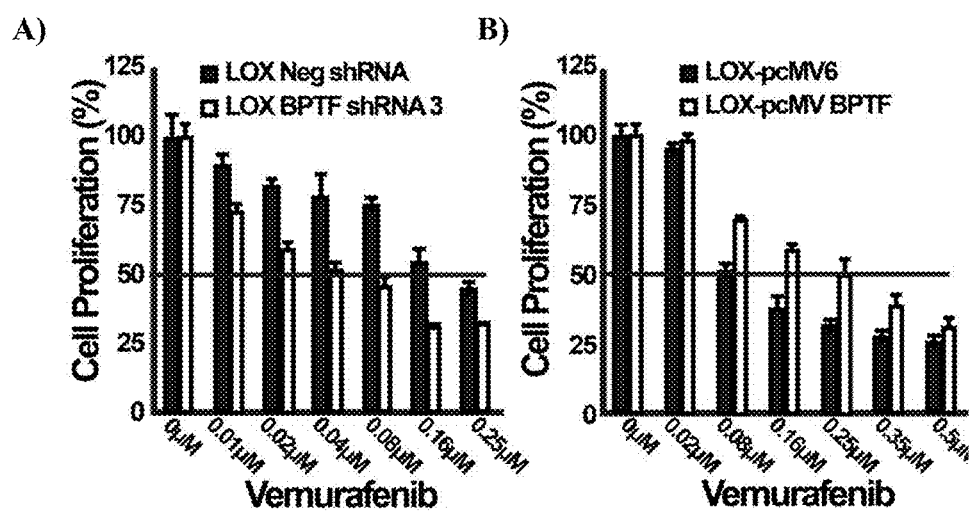
FIGURE 12A-B

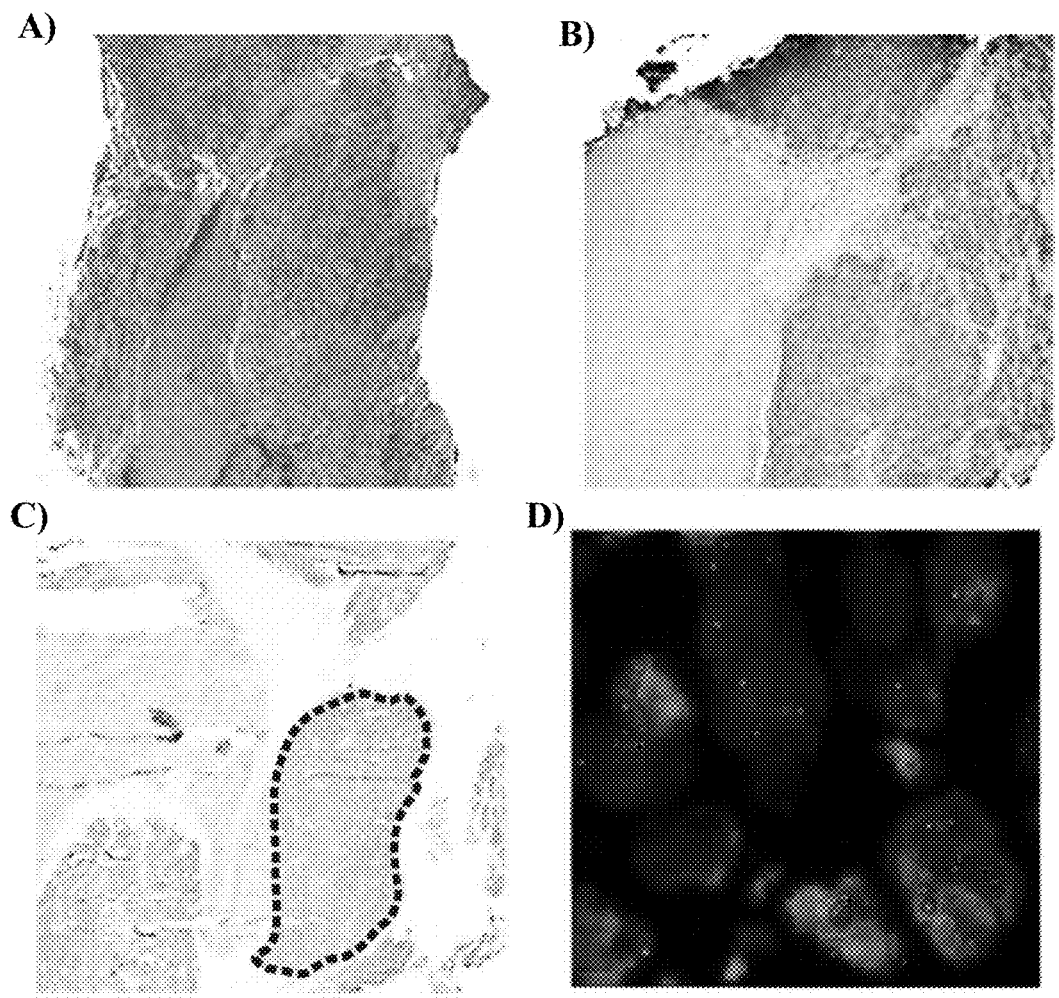
FIGURE 13A-D

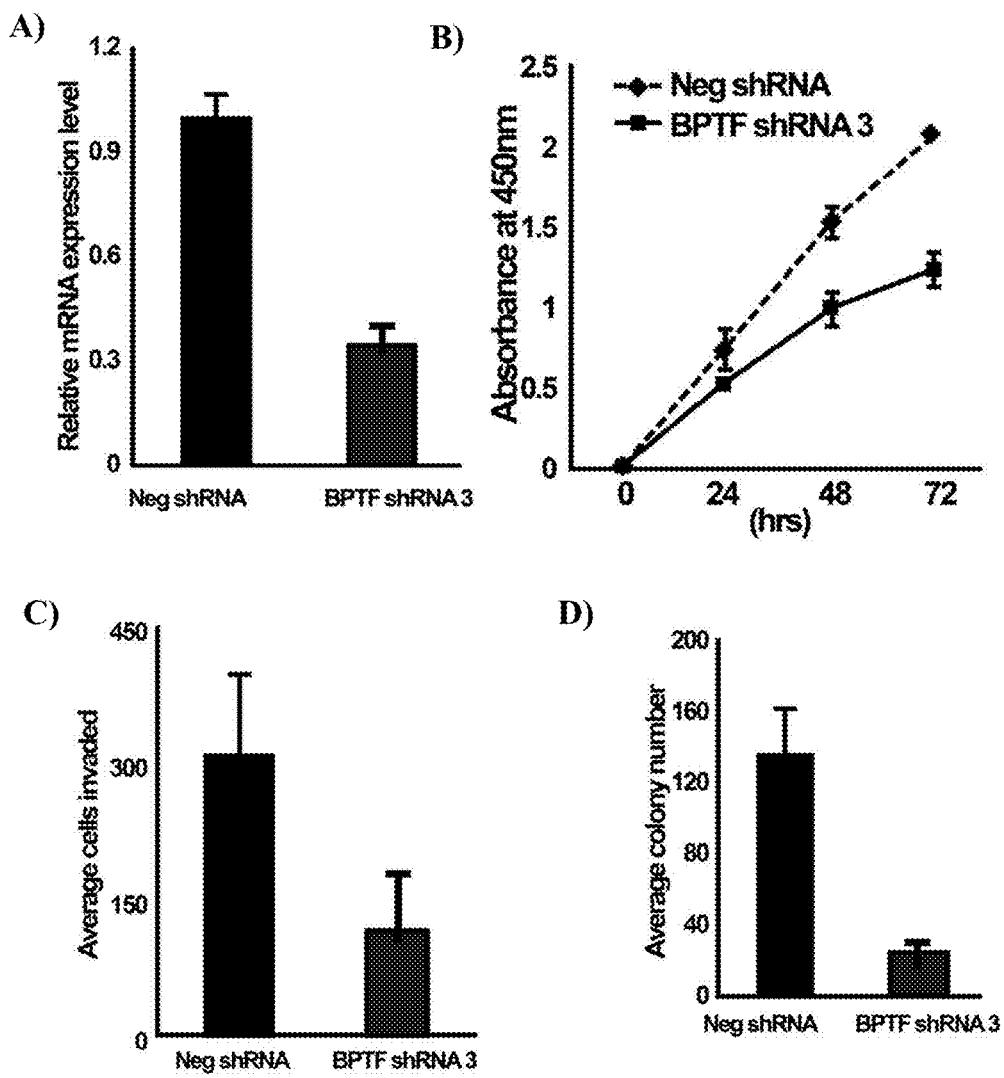
Figure 14A-D

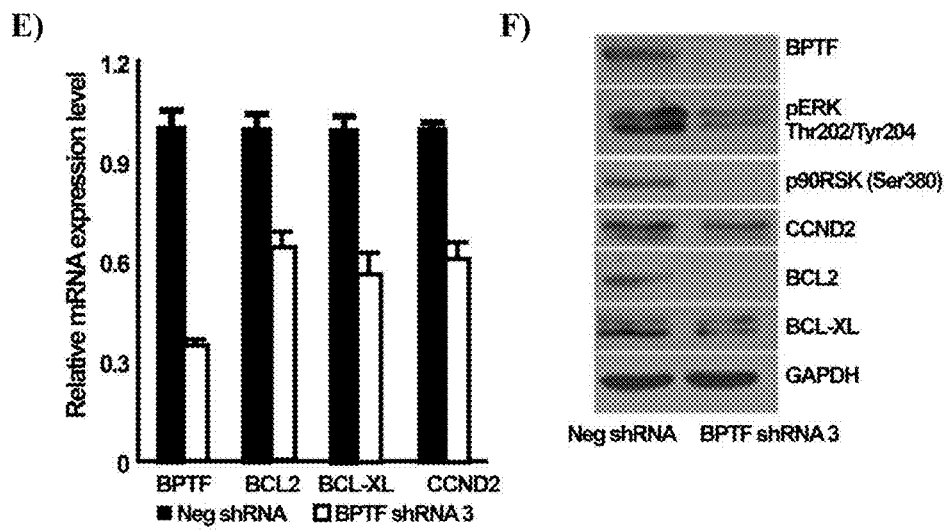
FIGURE 14E-F
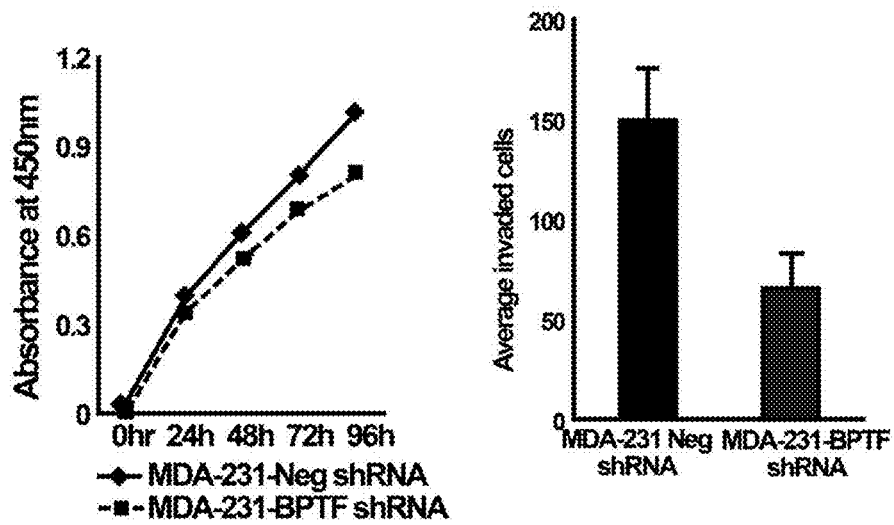
FIGURE 15

FALZ FOR USE AS A TARGET FOR THERAPIES TO TREAT CANCER

CROSS REFERENCE TO RELATED APPLICATIONS

This application is a U.S. National Stage Application filed under 35 U.S.C. § 371 and claims priority to International Application No. PCT/US2014/029986, filed Mar. 15, 2014, which application claims priority under 35 U.S.C. § 119 from Provisional Application Ser. No. 61/790,153, filed Mar. 15, 2013, the disclosures of which are incorporated herein by reference.

GOVERNMENT LICENSE RIGHTS

This invention was made with Government support under Grant Nos. CA114337 & CA122947, awarded by the National Institutes of Health and National Cancer Institute. The Government has certain rights in the invention.

TECHNICAL FIELD

The disclosure provides methods for cancer diagnosis, subject survival rate, and/or cancer progression based upon measuring the expression levels of FALZ. The disclosure further provides a method for treating a subject with cancer by inhibiting FALZ activity and/or expression.

BACKGROUND

Epigenetic mechanisms, including post-translational modifications of histones, DNA methylation, incorporation of histone variants, and nucleosome remodeling have evolved to regulate the structure of chromatin and access to DNA.

SUMMARY

BPTF (bromodomain PHD finger transcription factor; also referred to as FALZ (fetal Alzheimer antigen)), is a gene whose precise role in neoplastic transformation is unclear. The disclosure shows that FALZ expression is an independent prognostic marker for primary melanoma, and may represent a predictive biomarker of response to targeted therapy in melanoma. In addition, shRNA-mediated suppression of FALZ resulted in significantly decreased growth of melanoma, glioblastoma, and breast cancer cells in vitro and/or in vivo, suggesting the potential therapeutic utility of targeting FALZ in the therapy of melanoma as well as other solid tumors.

The disclosure provides a method of prognosis of cancer, comprising: (i) obtaining a biological sample from a subject; (ii) measuring the level of BPTF in the subject's sample; (iii) comparing the level of BPTF in the subject's sample with the mean level of BPTF from one or more control biological samples; (iv) providing a prognosis that the subject may have cancer based on having a lower (or higher) level for BPTF in comparison to the mean level of BPTF in the controls. In one embodiment, the cancer is selected from the group consisting of melanoma, breast cancer and brain cancer. In another embodiment, the subject's biological sample is from a tissue biopsy. In yet a another embodiment, the one or more control biological samples are from tissue biopsies of benign nevi. In a further embodiment, the control biological samples comprise samples from the subject. In still another embodiment, the control biological samples comprise samples not from the subject. In one embodiment, the disclosure uses a labeled antibody or nucleic acid fragment that specifically binds to a BPTF polypeptide or polynucleotide, respectively.

The disclosure provides a method of determining whether a subject has a cancer, comprising: (i) obtaining a biological sample from a subject; (ii) measuring the level of BPTF in the subject's sample; (iii) comparing the level of BPTF in the subject's sample with the mean level of BPTF from one or more control biological samples; and (iv) determining whether the subject has cancer based on having a significantly lower (or higher) level for BPTF in comparison to the mean levels for BPTF in the controls. In one embodiment, the cancer is selected from the group consisting of melanoma, breast cancer and brain cancer. In another embodiment, the subject's biological sample is from a tissue biopsy. In yet another embodiment, the one or more control biological samples are from tissue biopsies of benign nevi. In a further embodiment, the control biological samples comprise samples from the subject. In yet another embodiment, the control biological samples comprise samples not from the subject. In one embodiment, the disclosure uses a labeled antibody or nucleic acid fragment that specifically binds to a BPTF polypeptide or polynucleotide, respectively.

The disclosure provides a method of determining whether a cancer in a subject is progressing or in remission, comprising: (i) obtaining a biological sample from a subject at a first time point; (ii) measuring the level of BPTF in the subject's sample from the first time point; (iii) obtaining a biological sample from a subject at a second time point; (iv) measuring the level of BPTF in the subject's sample from the second time point; (v) comparing the levels of BPTF from the first time point with the levels from the second time point; and (vi) determining whether a cancer is progressing or is in recovery based upon the change in levels of BPTF from the two time points, wherein an increase in BPTF levels between the first time point and the second time point indicates that the cancer is in remission, and wherein an increase in BPTF levels between the first time point and the second time point indicates the cancer is progressing. In one embodiment the cancer is selected from the group consisting of melanoma, breast cancer and brain cancer. In another embodiment, the biological samples are from tissue biopsies. In yet another embodiment, the method includes administering an anti-cancer therapeutic agent to the subject following obtaining the first sample. In yet another embodiment, the method includes administering a BPTF inhibitory agent to the subject if the BPTF levels increased. In one embodiment, the disclosure uses a labeled antibody or nucleic acid fragment that specifically binds to a BPTF polypeptide or polynucleotide, respectively.

The disclosure provides a method of providing a prognosis of the survival rate of a subject who has a cancer, comprising: (i) obtaining a biological sample from a subject at a first time point; (ii) measuring the level of BPTF in the subject's sample from the first time point; (iii) obtaining a biological sample from a subject at a second time point; (iv) measuring the level of BPTF in the subject's sample from the second time point; (v) comparing the levels of BPTF from the first time point with the levels from the second time point; and (vi) providing a prognosis of the subject's survival rate based upon the change in levels of BPTF from the two time points, wherein an increase in BPTF levels between the first time point and the second time point indicates a poor survival rate for the subject, and wherein a decrease in BPTF levels between the first time point and the second time point indicates a better survival rate for the subject. In one embodiment, the cancer is selected from the group consisting of melanoma, breast cancer and brain cancer. In another embodiment, the biological samples are from tissue biopsies. In one embodiment, the disclosure uses a labeled antibody or nucleic acid fragment that specifically binds to a BPTF polypeptide or polynucleotide, respectively.

The disclosure also provides a method of treating a cancer in a subject, the method comprising: inhibiting the expression of BPTF by administering an effective amount of an inhibitory BPTF nucleic acid and/or an effective amount of an agent that inhibits the expression of BPTF. In one embodiment, the cancer is selected from the group consisting of melanoma, glioblastoma multiforme and breast cancer. In another embodiment, the inhibiting of the expression of BPTF results in inhibiting or preventing the proliferation or migration of cancer cells. In yet another embodiment, the method is used in combination with one or more additional anti-cancer therapeutic agents. In a further embodiment, the one or more additional therapeutic agents are selected from the group consisting of platinum analogs, alkylating agents, alkyl sulfonates, androgens, anti-adrenals, anti-androgens, antibiotics, anti-estrogens, aromatase inhibiting 4(5)-imidazoles, anti-metabolites, folic acid analogues, ethylenimines and methylamelamines, folic acid replenishers, nitrogen mustards, nitrosureas, purine analogs, pyrimidine analogs, topoisomerase inhibitors, thymidylate synthase inhibitors, anti-cancer antibodies, chemotherapeutics, de-methylation agents, and targeted therapeutic agents. In yet another embodiment, the method comprises administering a vector comprising an inhibitory BPTF nucleic acid to the subject. In yet a further embodiment, the vector comprises an expression vector. In still a further embodiment, the vector comprises a replication competent retroviral vector.

The disclosure also provides a composition comprising a BPTF inhibitor and a first-line anti-cancer therapeutic.

The disclosure provides for one or more embodiments set forth in the accompanying drawings and the description below. Other features, objects, and advantages of the invention will be apparent from the description and drawings, and from the claims.

DESCRIPTION OF DRAWINGS

FIG. 1A-F shows effects of shRNA-mediated suppression of Bptf expression on murine melanoma. A) Downregulation of Bptf expression at the mRNA level by two different shRNAs in B16-F10 murine melanoma cells. B) Suppression of cell proliferation following Bptf knockdown. C-D) In vivo tumor cell growth and metastatic lung tumor burden is significantly suppressed by Bptf knockdown. E-F) Suppression of CCND2 and BCL-XL expression at the mRNA and protein levels after Bptf knockdown.

FIG. 2A-G shows the effects of suppression of BPTF expression on human melanoma. A) Suppression of BPTF expression at the mRNA level in 1205-Lu cells. B) BPTF suppression induces G0/G1 arrest and reduces the S-phase of the cell cycle. CD) Significant suppression of cellular proliferation following BPTF knockdown as determined by assays of cell survival and colony formation, respectively. E) BPTF knockdown induces apoptosis in melanoma cells. F-G) In vivo tumor cell growth and metastatic tumor burden is significantly suppressed by BPTF knockdown.

FIG. 3A-D shows the effects of BPTF expression on sensitivity to DNase-I treatment and on the ERK1/2 pathway. A-B) Suppression of BPTF expression enhanced DNase-I hypersensitivity to the promoter sequences of BCL-XL and BCL-2 in 1205-Lu and C8161.9 cells. C-D) Expression of CCND2, BCL-XL and BCL-2 at the mRNA level in two melanoma cell lines after BPTF suppression in 1205-Lu and C8161.9 cells. C-F) Western blot analyses showing expression of various proteins after BPTF suppression in 1205-Lu and C8161.9 cells.

FIG. 4A-D shows BPTF levels in primary cutaneous melanoma. A-B) Kaplan-Meier analysis of DMFS and DSS in melanoma patients with highest BPTF expression levels (curve 1) versus all other patients (curve 2). C-D) Representative photomicrographs of FISH analysis showing low and high BPTF copy number in tissue samples.

FIG. 5A-H shows the effects of modulation of BPTF expression on sensitivity to selective BRAF inhibitors. A-B) BPTF knockdown sensitizes 1205-Lu melanoma cells to vemurafenib and dabrafenib. C-D) BPTF overexpression in 1205-Lu melanoma cells confers resistance to BRAF inhibitors. E) H&E staining of metastatic melanoma specimen following acquired resistance to vemurafenib. F) Immunohistochemical analysis of BPTF expression of sample in (E) showing heterogeneous pattern of BPTF staining. G) Pan-melanoma staining of specimen in (E). H) Fluorescence in situ hybridization (FISH) analysis of BPTF copy in the resistant specimen.

FIG. 6A-I shows the effects of suppression of BPTF expression on human glioblastoma cells. A) shRNA-mediated suppression of BPTF at the mRNA level in U251 cells. B-C) Significant suppression of cellular proliferation following BPTF knockdown as determined by assays of cell survival and colony formation, respectively. D) BPTF suppression induces G0/G1 arrest and reduces the S-phase of the cell cycle. E) BPTF knockdown induces apoptosis in U251 cells. F) mRNA expression of different genes following BPTF suppression. G) Western blot analysis showing expression of various proteins. H) In vivo growth of U251 cells in nude mice following BPTF suppression. I) BPTF expression in mesenchymal and proneural GBM subtypes.

FIG. 7A-C shows BPTF suppression suppresses the invasive potential of B16-F10 murine melanoma (A), 1205-Lu human melanoma (B), and U251 human GBM (C) cells.

FIG. 8A-F shows the effects of BPTF suppression on C8161.9 human melanoma cells. A) Suppression of BPTF at the mRNA level in C8161.9 melanoma cells. B-C) Significant suppression of cellular proliferation following BPTF knockdown as determined by assays of cell survival and colony formation, respectively. D) BPTF knockdown induces apoptosis in C8161.9 melanoma cells. E) BPTF knockdown suppresses the invasiveness of C8161.9 melanoma cells. F) In vivo tumor growth of C8161.9 cells is significantly suppressed by BPTF knockdown.

FIG. 9 shows the overexpression of BCL-XL or ERK rescues the effects of BPTF suppression on 1205-Lu melanoma cell survival.

FIG. 10A-C: A) BPTF overexpression enhances cellular proliferation in 1205-Lu melanoma cell lines. B) Levels of expression of various genes following BPTF overexpression. C) Western blot showing expression of various proteins following BPTF overexpression.

FIG. 11A-B shows Immunohistochemical analysis of BPTF expression in a tissue microarray showing illustrative photomicrographs of BPTF expression. A) Primary melanoma expressing low levels of BPTF; B) primary melanoma expressing high levels of BPTF.

FIG. 12A-B: A) BPTF knockdown sensitizes LOX melanoma cell lines to vemurafenib treatment. B) BPTF overexpression in LOX melanoma cell lines confers resistance to vemurafenib treatment.

FIG. 13A-D: A) H&E staining of metastatic tumor sample following resistance to dabrafenib. B) Immunohistochemical staining of tumor sample showing heterogeneous pattern of BPTF staining. C) Pan melanoma staining of metastatic melanoma. D) Fluorescence in situ hybridization (FISH) analysis of BPTF copy number in metastatic melanoma.

FIG. 14A-F: A) shRNA-mediated suppression of BPTF mRNA in LN18 human glioblastoma cells. B-C) Suppression of cellular proliferation following BPTF knockdown as determined by assays of cell survival and colony formation, respectively. D) BPTF knockdown suppresses invasiveness of LN18 cells. E-F) Level expression of various genes following BPTF suppression. F) Western blot analysis showing expression of various proteins following BPTF suppression.

FIG. 15 shows that shRNA mediated suppression of FALZ in MDA-231 breast cancer cell lines suppresses tumor cell proliferation (left panel) and invasiveness (right panel).

DETAILED DESCRIPTION

Figure 16:
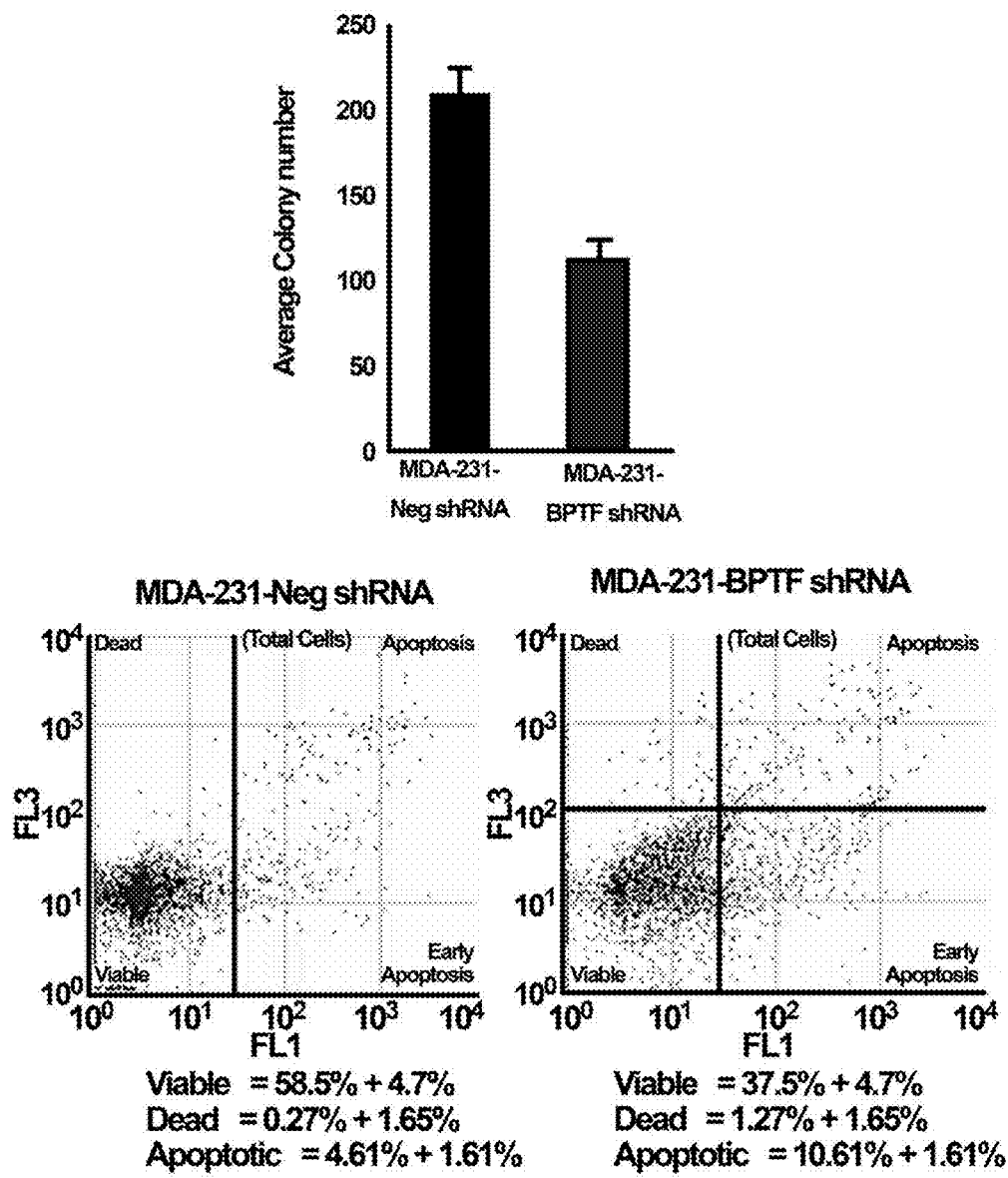
FIG. 16 shows that shRNA-mediated suppression of FALZ suppresses colony formation ability (Left panel) and induces apoptosis (right panel) in MDA-231 breast cancer cell lines.
Figure 17:
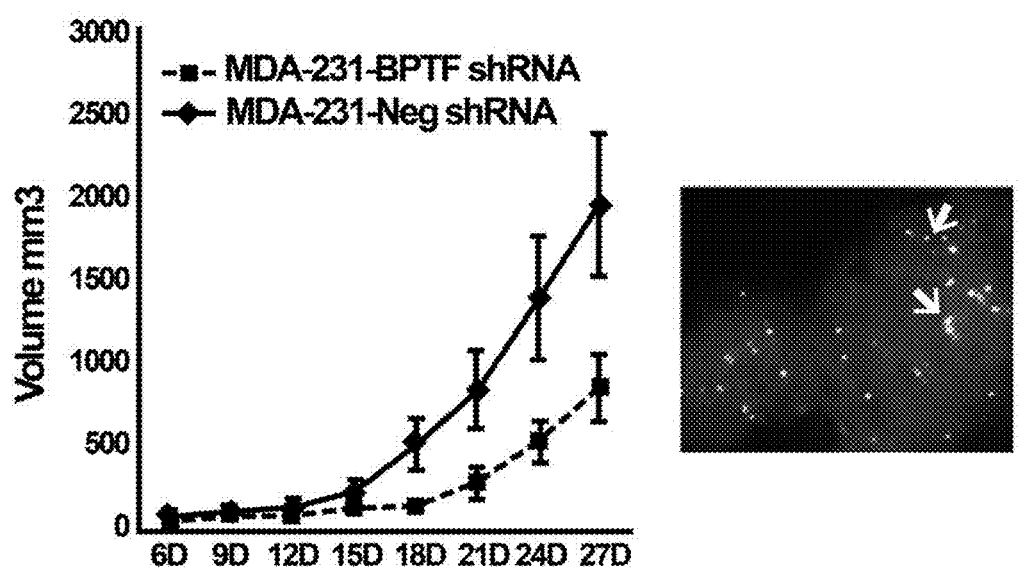
FIG. 17 shows FALZ knockdown in MDA-231 breast cancer cell lines suppresses in vivo tumor growth in nude mice (Left panel). The right panel shows FISH analysis on human breast cancer tissue specimens indicating increase in FALZ copy number.

As used herein and in the appended claims, the singular forms "a," "and," and "the" include plural referents unless the context clearly dictates otherwise. Thus, for example, reference to "a polynucleotide" includes a plurality of such polynucleotides and reference to "the cell" includes reference to one or more cells, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

The publications discussed above and throughout the text are provided solely for their disclosure prior to the filing date of the present application. Nothing herein is to be construed as an admission that the inventors are not entitled to antedate such disclosure by virtue of prior disclosure. Moreover, with respect to any term that is presented in one or more publications that is similar to, or identical with, a term that has been expressly defined in this disclosure, the definition of the term as expressly provided in this disclosure will control in all respects.

Nucleosome remodeling and the incorporation of histone variants are largely accomplished through the action of ATP-dependent chromatin-remodeling complexes, which represent critical components of the machinery that controls gene expression. ATP-dependent chromatin-remodeling factors are classified into four major subfamilies (ISWI, SWI/SNF, CHD and INO80) based upon sequence homology of the associated ATPase.

Chromatin-remodeling factors have been recognized to play an increasingly important role in tumorigenesis given the recent demonstration of mutations in chromatin regulators in various human cancers. In addition, the 17q24 locus has long been presumed to contain oncogenes, given its amplification in a number of tumors. Bromodomain PHD finger transcription factor (BPTF; also referred to as FALZ) (whose gene resides on 17q24), the largest component of the NURF complex, has been implicated in embryonic development, thymocyte maturation, and chromatin remodeling. The NURF complex in mammals is a well-characterized ATP-dependent chromatin-remodeling complex. However, little is known about the functional role played by BPTF in tumorigenesis.

Nucleosome remodeling factor (NURF), identified in *Drosophila melanogaster*, is a key member of the ISWI family of ATP-dependent chromatin-remodeling factors. In mammals, BPTF (bromodomain PHD finger transcription factor) represents the orthologue of the *Drosophila* NURF301, the largest subunit of the NURF chromatin-remodeling complex. The NURF301 homolog exists across all eukaryotic species and appears to be evolutionarily conserved. NURF301 participates in the regulation of expression of engrailed 1 and 2, presumably by changing the periodic alignment of nucleosomes.

The NURF complex mediates some of its cellular functions through interaction with sequence-specific transcription factors. In *Drosophila*, heat shock factor (HSF), GAGA, and the artificial domain VP16 have been shown to interact with multiple surfaces on NURF301 and weakly with ISWI. NURF301 has two well-characterized domains that bind specific histone post-translational modifications. The PHD finger juxtaposed to the bromodomain interacts with H3K4me2/3 and the adjacent bromodomain binds H4K16ac. In addition, NURF likely interacts directly with DNA in a sequence-specific fashion. BPTF (also referred to as FALZ) has been reported to be essential in embryonic development and involved in ATP-dependent chromatin remodeling.

The disclosure demonstrates that BPTF (sometimes referred to as FALZ herein) is significantly overexpressed in metastatic melanomas and breast cancer by cDNA microarray analysis and FISH. The human BPTF gene (SEQ ID NO:1) is located on chromosome 17q24, which is a hotspot for chromosomal changes in many tumors. Amplification of 17q24 has been shown in breast cancer, and increased 17q24 copy number has been observed in other solid tumors. A translocation occurring at the 17q24.3 locus encompassing the BPTF gene was demonstrated in lung embryonic cells. FAC1 (Fetal Alz-50-reactive clone 1) a truncated form of BPTF, is upregulated in neurodegenerative diseases, exhibits sequence-specific DNA binding activity, and may function in transcriptional regulation. While the importance of remodeling complexes such as NURF is well understood, to date, the functional role of BPTF in tumorigenesis has been incompletely characterized.

This disclosure provides a functional and biological role of BPTF in melanoma, glioblastoma multiforme (GBM), and breast cancer. Although these cancer types were specifically analyzed, the role of BPTF in other tumors and cancers is contemplated. The disclosure demonstrates that targeted suppression of BPTF suppresses melanoma, GBM, and breast cancer cell proliferation; that BPTF copy number is elevated in a significant proportion of melanomas and breast cancers, and BPTF overexpression is a marker of reduced survival in human melanoma patients. Furthermore, BPTF modulates the ERK pathway and confers acquired resistance to selective BRAF inhibitors in BRAF-mutant melanoma cells.

The disclosure demonstrates the functional and biological significance of BPTF in tumor progression, with a specific focus on melanoma, glioblastoma, and breast cancer. Suppression of BPTF expression in murine melanoma cells and breast cancer cells resulted in significant suppression of tumor cell proliferation and invasiveness. In vivo studies confirmed the powerful role played by BPTF in melanoma progression, as a significant decrease in tumor cell growth and metastatic tumor count was observed by using different shRNAs targeting BPTF. The effects of BPTF on cell cycle progression and on in vitro and in vivo tumor cell growth were confirmed in two human melanoma and GBM cell lines as well as in breast cancer cells.

To gain mechanistic insight into BPTF function in melanoma cells, integrated analyses identified the downregulation of BCL2, BCL-XL and CCND2, which are key mediators of tumor cell proliferation, cell cycle progression, and apoptosis, following suppression of BPTF expression. The downregulation of these genes was confirmed by qRT-PCR and western blot analyses in melanoma and GBM cell lines. As the NURF complex in mammals has been shown to influence nucleosome positioning and nuclease hypersensitivity sites in vitro, the disclosure demonstrates that suppression of BPTF expression enhanced sensitivity to DNase I treatment of the BCL2 and BCL-XL genes.

Beyond the mechanistic analysis of BPTF action in melanoma, breast cancer and GBM, a detailed analysis of the role of BPTF as a biomarker of melanoma was also performed. FISH analysis of primary melanoma revealed elevated BPTF copy number in 36% of cases, in contrast with benign nevi in which increased BPTF copy number was absent. This suggests the potential utility of BPTF as a potential diagnostic marker to distinguish melanoma from nevi. Furthermore, the increased BPTF copy number observed may provide a mechanism for BPTF activation in melanoma, identifying a genetic basis for the overexpression of BPTF observed in the gene expression profiling analysis. In addition, digital imaging analysis of BPTF immunostaining identified BPTF overexpression as an independent predictor of distant metastasis-free and disease specific survival in human melanoma patients. Thus, these studies showed that BPTF is both a predictor and a promoter of distant metastasis, the lethal event in melanoma progression. Taken together, these findings establish BPTF as a novel target, molecular marker and mediator of melanoma tumorigenesis and tumor progression. In addition, analysis of BPTF expression in GBM tissues and breast cancer cells indicated that BPTF expression was enriched in the pro-neural subtype of GBM, which responds poorly to chemotherapeutic agents and in breast cancer cells.

BRAF is a major oncogenic driver in melanoma by virtue of point mutations in 40-50% of cases. Mutant BRAF constitutively activates the MAP kinase pathway, and transduces pro-proliferative and pro-survival signals in melanoma cells, in addition to promoting tumor cell invasion and angiogenesis. Importantly, suppression of BPTF expression produced pronounced anti-tumor effects in melanoma cells harboring either mutant (1205-Lu) or wild type (C8161.9) BRAF, and resulted in significantly reduced levels of phosphorylated ERK1/2 (Thr204/Tyr204) as well as its direct target p90RSK (Ser380), which represent downstream effectors of the MAPK pathway. Intriguingly, three of the genes that were suppressed upon BPTF knockdown (BCL2, BCL-XL and CCND2) are regulated by ERK. These findings provide evidence that BPTF activates the MAPK pathway and thereby enhances tumor cell proliferation, invasiveness and survival while suppressing tumor cell apoptosis.

Treatment of metastatic melanoma patients harboring a BRAF mutation with selective BRAF inhibitors has been shown to confer an overall survival advantage. However, complete responses are rare and acquired resistance to these agents develops in the majority of treated cases. Several mechanisms of acquired resistance have been described, primarily including reactivation of the MAPK pathway [via N-RAS mutations or COT/MAP3K8 kinase overexpression], activation of platelet-derived growth factor receptor β or via activation of the PI3K pathway (via overexpression of IGF1R. The disclosure shows that modulation of BPTF expression (by either overexpression or shRNA-mediated downregulation) significantly modulated sensitivity of mutant BRAF melanoma cells to selective BRAF inhibitors and further provides new evidence that chromatin-remodeling factors are involved in promoting acquired resistance to targeted therapies in cancer. In addition to the mechanistic analysis of sensitivity to BRAF inhibitors in melanoma cell lines, analysis of specimens prior to and following progression with selective BRAF inhibitors indicated increased BPTF copy number upon therapeutic resistance in a subset of cases. This suggests that BPTF activation can be selected for during resistance to targeted therapy in melanoma, given that it can promote melanoma cell proliferation and survival.

Surprisingly, there was a significant difference in the immunohistochemical analysis of BPTF expression in the pre-treatment and progressing lesions. While BPTF expression in the pre-treatment metastatic tumor was homogeneous, analysis of the progressing lesions identified, in some tumors, distinct clones of cells with divergent morphology and BPTF expression. One clone of tumor cells (devoid of BPTF staining) represented apoptotic cells that appeared to have responded to therapy, while the other clone identified surviving cells (with prominent BPTF staining) that possibly represented the resistant clone. This leads to the intriguing speculation that the metastatic tumor resistant to targeted therapy is not homogeneously resistant, but rather composed of cell subpopulations that are still actively responding to treatment. These observations are consistent with the recent demonstration of intratumor molecular heterogeneity of renal cell carcinoma, and are supported by a recent study that showed heterogeneous immunohistochemical marker expression in metastatic melanoma following progression on targeted therapy. Taken together, these results clearly support efforts at examining the potential utility of combinatorial therapies that are planned or under way targeting some of the aforementioned mechanisms of resistance. In addition, they suggest BPTF targeting as a possible approach to overcome resistance to BRAF inhibitors, or as a possible combinatorial treatment for metastatic melanomas with mutant BRAF.

In a recent study, BPTF was among a group of chromatin-remodeling factors mutated in liver cancers by whole-genome sequencing. Analysis of the COSMIC database reveals mutations in BPTF in a small number of skin cancers, including melanoma. The disclosure demonstrates an oncogenic role for BPTF in melanoma, breast cancer and glioblastoma, driven in part by increased copy number in a subset of cases. The results presented herein assign a novel functional role for BPTF in tumor progression by virtue of its effects on tumor cell proliferation and survival, via activation of BCL2, BCL-XL, CCND2, and ERK. BPTF overexpression is an independent predictor of survival associated with melanoma. Further, increased levels of BPTF promote resistance to therapies targeting mutant BRAF and may be selected for during acquired resistance to these agents.

In view of the data provided herein and the examples below, the disclosure provides methods and compositions useful for (a) treating cancers having an aberrant expression of BPTF, (b) increasing targeted therapy using existing first line chemotherapeutics and antibodies by inhibiting induced drug resistance resulting from BPTF expression, and (c) diagnostics useful for identifying progression and therapy of cancer. The methods of treatment described herein can use inhibitor nucleic acid therapy (e.g., shRNA, siRNA, antisense molecules and the like) to downregulate BPTF expression. Alternatively, the disclosure can improve a therapy by combining a BPTF inhibitor (e.g., a bromodomain inhibitor) with first-line therapeutics. Exemplary bromodomain inhibitors are described in, e.g., U.S. Pat. Publ. No. 2014/0066410, the disclosure of which is incorporated herein by reference). In this latter embodiment, the therapeutic method and compositions would be a combination of a bromodomain inhibitor and a first-line therapeutic for the cancer. The bromodomain inhibitor can be administered prior to, in combination with, or after administration of a first-line therapeutic/chemotherapeutic.

As used herein, the term "antisense oligonucleotide" refers to an unmodified or modified nucleic acid having a nucleotide sequence complementary to a BPTF polynucleotide sequence including polynucleotide sequences associated with the transcription or translation of BPTF (e.g., a promoter of a BPTF polynucleotide), where the antisense polynucleotide is capable of hybridizing to a BPTF polynucleotide sequence. Of particular interest are antisense polynucleotides capable of inhibiting transcription and/or translation of BPTF polypeptide-encoding polynucleotide either in vitro or in vivo. Such antisense oligonucleotides can be delivered to a target cell through gene therapy (e.g., recombinant viral vectors), operably linked to charge neutralizing moieties (e.g., TAT or other protein transduction domains, see, e.g., US Pat. Publ. Nos. 2009/0093425, 2009/0093026, and 2006/0222657, the disclosure of which are incorporated herein by reference) or direct nucleic acid delivery techniques.

As used herein; the terms "siRNA oligonucleotides", "RNAi oligonucleotides", "short interfering RNA", or "siRNA" are used interchangeably and refer to oligonucleotides that work through post-transcriptional gene silencing, also known as RNA interference (RNAi). The terms refer to a double stranded nucleic acid molecule capable of RNA interference "RNAi", (see Kreutzer et al., WO 00/44895; Zernicka-Goetz et al. WO 01/36646; Fire, WO 99/32619; Mello and Fire, WO 01/29058). SiRNA molecules are generally RNA molecules but further encompass chemically modified nucleotides and non-nucleotides. siRNA gene-targeting experiments have been carried out by transient siRNA transfer into cells (achieved by such classic methods as liposome-mediated transfection, electroporation, or microinjection). Molecules of siRNA are 21- to 23-nucleotide RNAs, with characteristic 2- to 3-nucleotide 3'-overhanging ends resembling the RNase III processing products of long double-stranded RNAs (dsRNAs) that normally initiate RNAi.

Effective exploitation of the siRNA pathway to mediate gene silencing depends, in part, on efficient methods of intracellular delivery of siRNA. siRNA molecules tend to be short-lived in the cell, not readily deliverable to cell types that are difficult to transfect and relatively expensive to produce via chemical syntheses. (Jacks et al., (2005) Biotechniques 39: 215-224; Bernards et al., (2006) Nature Methods 3: 701-706).

One method for efficient intracellular delivery of siRNA is the use of short hairpin RNAs, or "shRNAs". shRNAs are single stranded RNA molecules that include two complementary sequences joined by a non-complementary region. In vivo, the complementary sequences anneal to create a double-stranded helix with an unpaired loop at one end. The resulting lollipop-shaped shaped structure is called a stem loop and can be recognized by the RNAi machinery and processed intracellularly into short duplex RNAs having siRNA-like properties.

shRNA can be synthesized in a cell by transcription from a DNA template that has been inserted into an appropriate vector. Useful shRNAs are typically 50-70 nucleotides in length, with two complementary sequences of 19-29 nucleotides separated by a 5-10 nucleotide loop. shRNA construction is generally effected by one of dime methods: annealing of complementary oligonucleotides; promoter-based polymerase chain reaction (PCR); or primer extension. Many vector systems employ RNA Pol III promoters; Pol III-mediated transcription is advantageous because it initiates at a well-defined start-site, produces a non-poly (A) containing transcript and Pol III promoters are active in all cell types. (Brummelkamp et al., (2002) Science 296: 550-553; McIntyre, G. and Fanning, G. (2006) BMC Biotechnology 6: 1-8).

shRNA-encoding vector systems provide a renewable intracellular source of gene-silencing reagents that can mediate persistent gene silencing after stable integration of the vector into the host genome. Moreover, the shRNA cassette can be readily inserted into retroviral, lentiviral or adenoviral vectors to facility delivery of shRNA into a broad range of cell types, including nondividing primary cultures. Regulatable versions of, shRNA vectors are particularly useful for genetic screens.

Alternatively, iRNA molecules can be delivered through charge neutralization processes and compositions. For example, US Pat. Publ. Nos. 2009/0093425, 2009/0093026, and WO/2014/031575, which are incorporated herein by reference.

In one embodiment, the disclosure provide methods and compositions for treating a cancer wherein the cancer cells comprise over expression of a BPTF, the method comprising administering a composition comprising a nucleic acid inhibitor of BPTF. Such nucleic acid inhibitors can include, for example, siRNA, shRNA and precursors thereof. For example, the disclosure demonstrates that shRNA can be used to knockdown expression of BPTF and provide beneficial results. Such shRNAs include, but are not limited to, BPTF shRNA1: TGGCTGTGATCGGTGTCAGAATTGG-TACC (SEQ ID NO:3; wherein T can be U); BPTF shRNA2: GGTGATGAAGCATAATGCTGTA ATAGAAC (SEQ ID NO:4; wherein T can be U); and BPTF shRNA3 (SEQ ID NO:5; wherein T can be U): ATTTAGATTCAT-CATAAGGCG as well as any of the forgoing comprising a modified based, charge neutralization moiety and the like. The inhibitory nucleic acids are administered in a therapeutically effective amount.

As used herein, the term "therapeutically effective amount" is meant to refer to an amount of a medicament which produces a medicinal effect observed as reduction or reverse in one or more clinical endpoints, growth and/or survival of cancer cell, metastasis of cancer cells in an individual, or reduced resistance of a cancer cells to a chemotherapeutic of first-line anti-cancer agent, when a therapeutically effective amount of the medicament is administered to the individual. Therapeutically effective amounts are typically determined by the effect they have compared to the effect observed when a composition which includes no active ingredient is administered to a similarly situated individual. The precise effective amount for a subject will depend upon the subject's size and health, the nature and extent of the condition, and the therapeutics or combination of therapeutics selected for administration. However, the effective amount for a given situation is determined by routine experimentation and is within the judgment of the clinician.

As used herein, the terms "in combination with" or "in conjunction with" refer to administration of the BPTF modulators of the disclosure with other therapeutic regimens.

As used herein, the term "susceptible" refers to patients for whom BPTF therapy is an acceptable method of treatment, e.g., patients who are likely to respond positively. Cancer patients susceptible to BPTF therapy express high levels of BPTF relative to those patients not susceptible to BPTF therapy. Cancer patients who are not good candidates for BPTF therapy include cancer patients with tumor samples that lack or have lower levels of BPTF in or on their cancer cells.

As used herein, the term "detecting" means to establish, discover, or ascertain evidence of an activity (for example, gene expression) or biomolecule (for example, a polypeptide).

As used herein, the phrase "homologous nucleotide sequence," or "homologous amino acid sequence," or variations thereof, refers to sequences characterized by a homology, at the nucleotide level or amino acid level, of at least a specified percentage and is used interchangeably with "sequence identity". Homologous nucleotide sequences include those sequences coding for isoforms of proteins. Such isoforms can be expressed in different tissues of the same organism as a result of, for example, alternative splicing of RNA. Alternatively, isoforms can be encoded by different genes. Homologous nucleotide sequences include nucleotide sequences encoding for a protein of a species other than humans, including, but not limited to, mammals. Homologous nucleotide sequences also include, but are not limited to, naturally occurring allelic variations and mutations of the nucleotide sequences set forth herein. Homologous amino acid sequences include those amino acid sequences which contain conservative amino acid substitutions and which polypeptides have the same binding and/or activity.

Percent homology or identity can be determined by, for example, the Gap program (Wisconsin Sequence Analysis Package, Version 8 for UNIX, Genetics Computer Group, University Research Park, Madison Wis.), using default settings, which uses the algorithm of Smith and Waterman (Adv. Appl. Math., 1981, 2, 482-489). In some embodiments, homology between the probe and target is between about 50% to about 60%. In some embodiments, nucleic acids have nucleotides that are about 60%, about 70%, about 80%, about 85%, about 90%, about 92%, about 94%, about 95%, about 97%, about 98%, about 99% and about 100% homologous to SEQ ID NO:1, or a portion thereof. The disclosure further provides partial of full complements of SEQ ID NO:1 or its homologs.

Homology may also be at the polypeptide level. In some embodiments, polypeptides are about 60%, about 70%, about 80%, about 85%, about 90%, about 92%, about 94%, about 95%, about 97%, about 98%, about 99% and about 100% homologous to SEQ ID NO:2, or a portion thereof.

As used herein, the term "probe" refers to nucleic acid sequences of variable length. In some embodiments probes comprise at least about 10 and as many as about 6,000 nucleotides. In some embodiments probes comprise at least 12, at least 14, at least 16, at least 18; at least 20, at least 25, at least 50 or at least 75 consecutive nucleotides. Probes are used in the detection of identical; similar, or complementary nucleic acid sequences. Longer length probes are usually obtained from natural or recombinant sources, are highly specific to the target sequence, and are much slower to hybridize to the target than are oligomers. Probes may be single- or double-stranded and are designed to have specificity in PCR, hybridization membrane-based, in situ hybridization (ISH), fluorescent in situ hybridization (FISH), or ELISA-like technologies.

As used herein, the term "mixing" refers to the process of combining one or more compounds, cells, molecules, and the like together in the same area. This may be performed, for example, in a test tube, petri dish, or any container that allows the one or more compounds, cells, or molecules, to be mixed.

As used herein the term "isolated" refers to a polynucleotide, a polypeptide, an antibody, or a host cell that is in an environment different from that in which the polynucleotide, the polypeptide, or the antibody naturally occurs. Methods of isolating cells are well known to those skilled in the art. A polynucleotide, a polypeptide, or an antibody which is isolated is generally substantially purified.

As used herein, the term "substantially purified" refers to a compound (e.g., either a polynucleotide or a polypeptide or an antibody) that is removed from its natural environment and is at least 60% free, at least 75% free, and at least 90% free from other components with which it is naturally associated.

As used herein, the term "binding" means the physical or chemical interaction between two or more biomolecules or compounds. Binding includes ionic, non-ionic, hydrogen bonds, Van der Waals, hydrophobic interactions, etc. Binding can be either direct or indirect; indirect being through or due to the effects of another biomolecule or compound. Direct binding refers to interactions that do not take place through or due to the effect of another molecule or compound but instead are without other substantial chemical intermediates.

As used herein, the term "contacting" means bringing together, either directly or indirectly, one molecule into physical proximity to a second molecule. The molecule can be in any number of buffers, salts, solutions, etc. "Contacting" includes, for example, placing a polynucleotide into a beaker, microtiter plate, cell culture flask, or a microarray, or the like, which contains a nucleic acid molecule. Contacting also includes, for example, placing an antibody into a beaker, microtiter plate, cell culture flask, or microarray, or the like, which contains a polypeptide. Contacting may take place in vivo, ex vivo, or in vitro.

As used herein, the phrase "stringent hybridization conditions" or "stringent conditions" refers to conditions under which a probe, primer, or oligonucleotide will hybridize to its target sequence, but to a minimal number of other sequences. Stringent conditions are sequence-dependent and will be different in different circumstances. Longer sequences will hybridize with specificity to their proper complements at higher temperatures. Generally, stringent conditions are selected to be about 5° C. lower than the thermal melting point ($T_m$) for the specific sequence at a defined ionic strength and pH. The $T_m$ is the temperature (under defined ionic strength, pH and nucleic acid concentration) at which 50% of the probes complementary to the target sequence hybridize to the target sequence at equilibrium. Since the target sequences are generally present in excess, at $T_m$, 50% of the probes are hybridized to their complements at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 to 50 nucleotides) and at least about 60° C. for longer probes, primers or oligonucleotides. Stringent conditions may also be achieved with the addition of destabilizing agents, such as formamide.

As used herein, the term "moderate stringency conditions" refers to conditions under which a probe, primer, or oligonucleotide will hybridize to its target sequence, but to a limited number of other sequences. Moderate conditions are sequence-dependent and will be different in different circumstances. Moderate conditions are well-known to the art skilled and are described in, inter alia, Maniatis et al. (Molecular Cloning: A Laboratory Manual, Cold Spring Harbor Laboratory; 2nd Edition (December 1989)).

The nucleic acid compositions described herein can be used; for example, to produce polypeptides, as probes for the detection of mRNA in biological samples (e.g., extracts of human cells) or cDNA produced from such samples, to generate additional copies of the polynucleotides, to generate ribozymes or oligonucleotides (single and double stranded), and as single stranded DNA probes or as triple-strand forming oligonucleotides. The probes described herein can be used to, for example, determine the presence or absence of the polynucleotides provided herein in a sample. The polypeptides can be used to generate antibodies specific for a polypeptide associated with cancer, which antibodies are in turn useful in diagnostic methods, prognostic methods, and the like as discussed in more detail herein. Polypeptides are also useful as targets for therapeutic intervention, as discussed in more detail herein. Antibodies of the disclosure may also be used, for example, to purify, detect, and target the polypeptides of the present invention, including both in vitro and in vivo diagnostic and therapeutic methods. For example, the antibodies are useful in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988). These and other uses are described in more detail below. Antibodies to BPTF are known (e.g., from Bethyl Laboratories, Inc., Montgomery, Tex., USA).

As used herein the term "imaging agent" refers to a composition linked to an antibody, small molecule, or probe of the disclosure that can be detected using techniques known to those of skill in the art. As used herein, the term "evidence of gene expression" refers to any measurable indicia that a gene is expressed.

The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, amino acid copolymers, lipid aggregates and inactive virus particles. Such carriers are well known to those of ordinary skill in the art. Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles.

Specific examples of cancers that can be treated by the methods and compositions of the disclosure include, but are not limited to, BPTF associated cancers. As used herein, "BPTF associated cancer" refers to a cancer characterized by cells that differentially express BPTF relative to non-cancerous cells. The disclosure is also applicable to any tumor cell-type where BPTF plays a role in cancer cell growth, tumor formation, cancer cell proliferation, cancer cell metastasis, cell migration, resistance to therapeutics, and angiogenesis. In some embodiments, the cancer is breast cancer, skin cancer, esophageal cancer, liver cancer, pancreatic cancer, prostatic cancer, uterine cancer, cervical cancer, lung cancer, bladder cancer, ovarian cancer, multiple myeloma and melanoma.

The disclosure provides methods and compositions that provide for the treatment, inhibition, and management of diseases and disorders associated with BPTF overexpression as well as the treatment, inhibition, and management of symptoms of such diseases and disorders. Some embodiments of the invention relate to methods and compositions comprising compositions that treat, inhibit or manage cancer including, without limitation, cancer metastases, cancer cell proliferation, cancer cell growth and cancer cell invasion.

The disclosure further provides methods including other active ingredients in combination with the BPTF modulators and inhibitors of the disclosure. In some embodiments, the methods further comprise administering one or more conventional cancer therapeutics to the patient. In some embodiments the methods of the disclosure further comprise treating the patient with one or more of chemotherapy, radiation therapy or surgery in combination with a BPTF modulator or inhibitor. The administration of BPTF in combination with any other therapy can be performed prior to, simultaneously with, or subsequent to the administration of the non-BPTF therapy.

The disclosure also provides diagnostic and/or imaging methods using the BPTF modulators of the disclosure, particularly BPTF inhibitory antibodies and small inhibitory RNA molecules (e.g., siRNA, shRNA and the like), to diagnose cancer and/or predict cancer progression. In some embodiments, the methods of the disclosure provide methods of imaging and localizing tumors and/or metastases and methods of diagnosis and prognosis of a cancer. In some embodiments, the methods of the disclosure provide methods to evaluate the appropriateness of BPTF-related therapy.

The disclosure provides BPTF modulators and inhibitors for, inter alia, the treatment, diagnosis, detection or imaging of cancer. BPTF modulators or inhibitors are also useful in the preparation of medicaments for the treatment of cancer.

In some embodiments, the BPTF modulator or inhibitor is an oligonucleotide, a small molecule, a mimetic, or an antibody. In some embodiments, the BPTF modulator inhibits a BPTF biological activity by 25%, 50%, 60%, 70%, 75%, 80%, 90%, 95%, 97%, 98%, 99% or 100%, as compared to a control. In some embodiments, the BPTF modulator inhibits BPTF expression by at least 25%, 50%, 60%, 70%, 75%, 80%, 90%, 95%, 97%; 98%, 99% or 100%, as compared to a control.

As used herein a BPTF modulator includes any agent that modulates the expression or activity of BPTF. A "modulator" can be antagonistic or agonistic. For treatment of cancers, the BPTF modulator is an inhibitory or antagonistic molecule. Exemplary BPTF inhibitory agents include inhibitory antibodies, small molecule inhibitors (e.g., bromodomain inhibitors), and inhibitor nucleic acid molecules. BPTF inhibitory antibodies include antibodies that inhibit or reduce the biological activity of a BPTF polypeptide (e.g., a polypeptide comprising a sequence of SEQ ID NO:2, a mutant or variant thereof).

In some embodiments the BPTF modulator is a monoclonal antibody, a polyclonal antibody, a chimeric antibody, a human antibody, a humanized antibody, a single-chain antibody, or a Fab fragment. The antibody may be labeled with, for example, an enzyme, radioisotope, or fluorophore. In some embodiments, the BPTF modulator is a monoclonal antibody which binds to BPTF consisting of a sequence as set forth in SEQ ID NO:2. In diagnostic applications the antibody can be labeled with a detectable label.

In some embodiments the antibody is a humanized antibody. Humanized antibodies may be achieved by a variety of methods including, for example: (1) grafting the non-human complementary determining regions (CDRs) onto a human framework and constant region (a process referred to in the art as "humanizing"), or, alternatively, (2) transplanting the entire non-human variable domains, but "cloaking" them with a human-like surface by replacement of surface residues (a process referred to in the art as "veneering"). In the invention, humanized antibodies will include both "humanized" and "veneered" antibodies. Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016; and in the following scientific publications: Marks et al., Bio/Technology 10; 779-783 (1992); Lonberg et al., Nature 368 856-859 (1994); Morrison, Nature 368, 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995); Jones et al., Nature 321:522-525 (1986); Morrison et al., Proc. Natl. Acad. Sci; U.S.A., 81:6851-6855 (1984); Morrison and Oi, Adv. Immunol., 44:65-92 (1988); Verhoeyer et al.; Science 239:1534-1536 (1988); Padlan, Molec. Immun. 28:489-498 (1991); Padlan, Molec. Immunol. 31(3):169-217 (1994); and Kettleborough, C. A. et al., Protein Eng. 4(7):773-83 (1991) each of which is incorporated herein by reference.

An antibody to BPTF may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the disclosure may be recombinantly fused or conjugated to molecules useful as labels in detection assays and effector molecules such as heterologous polypeptides, drugs; radionuclides, or toxins. See, e.g., PCT publications WO 92/08495; WO 91/14438; WO 89/12624; U.S. Pat. No. 5,314,995; and EP 396,387.

In addition to chimeric and humanized antibodies, fully human antibodies can be derived from transgenic mice having human immunoglobulin genes (see, e.g., U.S. Pat. Nos. 6,075,181, 6,091,001, and 6,114,598, all of which are incorporated herein by reference), or from phage display libraries of human immunoglobulin genes (see, e.g. McCafferty et al., Nature, 348:552-554 (1990). Clackson et al., Nature, 352:624-628 (1991), and Marks et al., J. Mol. Biol., 222:581-597 (1991)).

Monoclonal antibodies can be prepared using the method of Kohler et al. (1975) Nature 256:495-496, or a modification thereof. Typically, a mouse is immunized with a solution containing an antigen. Immunization can be performed by mixing or emulsifying the antigen-containing solution in saline, preferably in an adjuvant such as Freund's complete adjuvant, and injecting the mixture or emulsion parenterally. Any method of immunization known in the art may be used to obtain the monoclonal antibodies of the invention. After immunization of the animal, the spleen (and optionally, several large lymph nodes) are removed and dissociated into single cells. The spleen cells may be screened by applying a cell well suspension to a plate or well coated with the antigen of interest. The B cells expressing membrane bound immunoglobulin specific for the antigen bind to the plate and are not rinsed away. Resulting B cells, or all dissociated spleen cells, are then induced to fuse with myeloma cells to form hybridomas, and are cultured in a selective medium. The resulting cells are plated by serial or limiting dilution and are assayed for the production of antibodies that specifically bind the antigen of interest (and that do not bind to unrelated antigens). The selected monoclonal antibody (mAb)-secreting hybridomas are then cultured either in vitro (e.g., in tissue culture bottles or hollow fiber reactors), or in vivo (as ascites in mice).

As an alternative to the use of hybridomas for expression, antibodies can be produced in a cell line such as a CHO or myeloma cell lines, as disclosed in U.S. Pat. Nos. 5,545,403; 5,545,405; and 5,998,144; each incorporated herein by reference. Briefly the cell line is transfected with vectors capable of expressing a light chain and a heavy chain, respectively. By transfecting the two proteins on separate vectors, chimeric antibodies can be produced. Immunol. 147:8; Banchereau et al. (1991) Clin. Immunol. Spectrum 3:8; and Banchereau et al. (1991) Science 251:70; all of which are herein incorporated by reference.

The phrase "complementarity determining region" refers to amino acid sequences which together define the binding affinity and specificity of the natural FY region of a native immunoglobulin binding site. See, e.g., Chothia et al., J. Mol. Biol. 196:901-917 (1987); Kabat et al., U.S. Dept. of Health and Human Services NaI Publication No. 91-3242 (1991). The phrase "constant region" refers to the portion of the antibody molecule, that confers effector functions. In the present invention, mouse constant regions are substituted by human constant regions. The constant regions of the subject humanized antibodies are derived from human immunoglobulins. The heavy chain constant region can be selected from any of the five isotypes: alpha, delta, epsilon, gamma or mu. One method of humanizing antibodies comprises aligning the non-human heavy and light chain sequences to human heavy and light chain sequences, selecting and replacing the non-human framework with a human framework based on such alignment, molecular modeling to predict the conformation of the humanized sequence and comparing to the conformation of the parent antibody. This process is followed by repeated back mutation of residues in the CDR region that disturb the structure of the CDRs until the predicted conformation of the humanized sequence model closely approximates the conformation of the non-human CDRs of the parent non-human antibody. Such humanized antibodies may be further derivatized to facilitate uptake and clearance, e.g., via Ashwell receptors. See, e.g., U.S. Pat. Nos. 5,530,101 and 5,585,089 which are incorporated herein by reference.

Humanized antibodies can also be produced using transgenic animals that are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/10741 also discloses transgenic non-primate mammalian hosts capable of mounting an immune response to an immunogen, wherein the antibodies have primate constant and/or variable regions, and wherein the endogenous immunoglobulin-encoding loci are substituted or inactivated. WO 96/30498 discloses the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions. Antibodies of the present invention can also be produced using human engineering techniques as discussed in U.S. Pat. No. 5,766,886, which is incorporated herein by reference.

Antibodies of the disclosure may be administered to a subject via in vivo therapeutic antibody gene transfer as discussed by Fang et al. (2005), Nat. Biotechnol. 23, 584-590. For example recombinant vectors can be generated to deliver a multicistronic expression cassette comprising a peptide that mediates enzyme independent, cotranslational self-cleavage of polypeptides placed between MAb heavy and light chain encoding sequences. Expression leads to stoichiometric amounts of both MAb chains. A preferred example of the peptide that mediates enzyme independent, cotranslational self-cleavage is the foot-and-mouth-disease derived 2A peptide.

Fragments of the antibodies are suitable for use in the methods of the invention so long as they retain the desired affinity of the full-length antibody. Thus, a fragment of an anti-BPTF antibody will retain the ability to bind to BPTF. Such fragments are characterized by properties similar to the corresponding full-length anti-BPTF antibody, that is, the fragments will specifically bind a human BPTF antigen expressed on the surface of a human cell.

In some embodiments, the antibodies bind to one or more epitopes in a domain of BPTF. In some embodiments, the antibodies modulate one or more BPTF related biological activities. In some embodiments the antibodies inhibit one or more of cancer cell growth, tumor formation, and cancer cell proliferation.

Antibodies are defined to be "specifically binding" if: 1) they exhibit a threshold level of binding activity, and/or 2) they do not significantly cross-react with known related polypeptide molecules. The binding affinity of an antibody can be readily determined by one of ordinary skill in the art, for example, by Scatchard, analysis (Scatchard, Ann. NY Acad. Sci. 51: 660-672, 1949).

The disclosure provides methods for treating and/or preventing cancer or symptoms of cancer in a subject comprising administering to the subject a therapeutically effective amount of one or more BPTF inhibitors of the disclosure. In some embodiments the cancer is a cancer associated with BPTF overexpression. In some embodiments, the cancer is breast cancer, skin cancer, esophageal cancer, liver cancer, pancreatic cancer, prostatic cancer, uterine cancer, cervical cancer, lung cancer, bladder cancer, ovarian cancer, multiple myeloma or melanoma. In some embodiments, the cancer is in a non-hormonally regulated tissue.

A therapeutically effective amount of the inhibitor compound can be determined empirically, according to procedures well known to medicinal chemists, and will depend, inter alia, on the age of the patient, severity of the condition, and on the ultimate pharmaceutical formulation desired. Administration of the modulators of the invention can be carried out, for example, by inhalation or suppository or to mucosal tissue such as by lavage to vaginal, rectal, urethral, buccal and sublingual tissue, orally, topically, intranasally, intraperitoneally, parenterally, intravenously, intralymphatically, intratumorly, intramuscularly, interstitially, intra-arterially, subcutaneously, intraoccularly, intrasynovial, transepithelial, and transdermally. In some embodiments, the inhibitors are administered by lavage, orally or inter-arterially. Other suitable methods of introduction can also include rechargeable or biodegradable devices and slow or sustained release polymeric devices. As discussed above, the therapeutic compositions of this disclosure can also be administered as part of a combinatorial therapy with other known anti-cancer agents or other known anti-bone disease treatment regimen.

The disclosure further provides methods of modulating a BPTF-related biological activity in a patient. The methods comprise administering to the patient an amount of a BPTF inhibitor effective to inhibit one or more BPTF biological activities. Suitable assays for measuring BPTF biological activities are set forth supra and infra.

The disclosure also provides methods of inhibiting cancer cell growth in a patient in need thereof comprising administering a therapeutically effective amount of one or more BPTF inhibitors to the patient. Suitable assays for measuring BPTF-related cell growth are known to those skilled in the art and are set forth supra and infra.

The disclosure further provides methods of inhibiting cancer in a patient in need thereof. The methods comprise determining if the patient is a candidate for BPTF therapy as described herein (e.g., wherein BPTF is overexpressed) and administering a therapeutically effective amount of one or more BPTF inhibitors to the patient if the patient is a candidate for BPTF therapy. If the patient is not a candidate for BPTF therapy, the patient is treated with conventional cancer treatment.

The disclosure further provides methods of inhibiting cancer in a patient, diagnosed or suspected of having a cancer. The methods comprise administering a therapeutically effective amount of one or more BPTF inhibitors to the patient.

The disclosure also provides methods of modulating one or more symptoms of cancer in a patient comprising administering to said patient a therapeutically effective amount of the BPTF inhibitory compositions described herein.

The disclosure also provides methods for inhibiting migration of cancer cells in a patient in need thereof comprising administering to the patient a therapeutically effective amount of a BPTF inhibitor. Suitable assays for measuring BPTF-related cell migration are known to those skilled in the art.

The disclosure also provides methods for prophylactically treating a patient who is predisposed to develop cancer, a cancer metastasis or who has had a metastasis and is therefore susceptible to a relapse or recurrence. The methods are particularly useful in high-risk individuals who, for example, have a family history of cancer or of metastasizing tumors, or show a genetic predisposition for a cancer metastasis. In some embodiments the tumors are BPTF-related tumors. A "BPTF-related" tumor or cancer is a tumor or cancer which shows an increased expression of BPTF compared to the same non-tumor or cancer cell type. Additionally, the methods are useful to prevent patients from having recurrences of BPTF-related tumors who have had BPTF-related tumors removed by surgical resection or treated with a conventional cancer treatment.

The disclosure also provides methods of inhibiting cancer progression and/or causing cancer regression comprising administering to the patient a therapeutically effective amount of a BPTF inhibitor.

In some embodiments, the patient in need of anti-cancer treatment is treated with the BPTF inhibitor of the disclosure in conjunction with chemotherapy and/or radiation therapy. For example, following administration of the BPTF inhibitor, the patient may also be treated with a therapeutically effective amount of anti-cancer radiation. In some embodiments chemotherapeutic treatment is provided in combination with BPTF inhibitor. In some embodiments BPTF inhibitors are administered in combination with chemotherapy and radiation therapy.

Methods of treatment comprise administering single or multiple doses of one or more BPTF inhibitors to the patient. In some embodiments the BPTF inhibitors are administered as injectable pharmaceutical compositions that are sterile, pyrogen free and comprise the BPTF modulators in combination with a pharmaceutically acceptable carrier or diluent.

In some embodiments, the therapeutic regimens of the disclosure are used with conventional treatment regimens for cancer including, without limitation, surgery, radiation therapy, hormone ablation and/or chemotherapy. Administration of the BPTF inhibitors of the disclosure may take place prior to, simultaneously with, or after conventional cancer treatment. In some embodiments, two or more different BPTF inhibitors are administered to the patient.

In some embodiments the amount of BPTF inhibitor administered to the patient is effective to inhibit one or more of cancer cell growth, tumor formation, cancer cell proliferation, cancer cell metastasis, cancer cell migration, angiogenesis, and the like. In some embodiments, the amount of BPTF inhibitor administered to the patient is effective to increase cancer cell death through apoptosis.

In some embodiments the disclosure provides compositions comprising two or more BPTF inhibitors to provide still improved efficacy against cancer. In, some embodiments the BPTF inhibitors are inhibitory nucleic acid molecules (e.g., shRNA, siRNA and antisense molecules) or inhibitory antibodies. Concurrent administration of two or more therapeutic agents does not require that the agents be administered at the same time or by the same route, so long as there is an overlap in the time period during which the agents are exerting their therapeutic effect. Simultaneous or sequential administration is contemplated, as is administration on different days or weeks.

In some embodiments the methods of the disclosure contemplate the administration of combinations, or "cocktails", of different BPTF inhibitory agents.

Cancer chemotherapeutic agents that can be used in combination with BPTF inhibitory agents of the disclosure include, without limitation, alkylating agents, such as carboplatin and cisplatin; nitrogen mustard alkylating agents; nitrosourea alkylating agents, such as carmustine (BCNU); antimetabolites, such as methotrexate; folinic acid; purine analog antimetabolites, mercaptopurine; pyrimidine analog antimetabolites, such as fluorouracil (5-FU) and gemcitabine (Gemzar®); hormonal antineoplastics, such as goserelin, leuprolide, and tamoxifen; natural antineoplastics, such as aldesleukin, interleukin-2, docetaxel, etoposide (VP-16), interferon alfa, paclitaxel (Taxol®), and tretinoin (ATRA); antibiotic natural antineoplastics, such as bleomycin, dactinomycin, daunorubicin, doxorubicin, daunomycin and mitomycins including mitomycin C; and vinca alkaloid natural antineoplastics, such as vinblastine, vincristine, vindesine; hydroxyurea; aceglatone, adriamycin, ifosfamide, enocitabine, epitiostanol, aclarubicin, ancitabine, procarbazine hydrochloride, carboquone, carboplatin, carmofur, chromomycin A3, antitumor polysaccharides, antitumor platelet factors, cyclophosphamide (Cytoxin®), Schizophyllan, cytarabine (cytosine arabinoside), dacarbazine, thioinosine, thiotepa, tegafur, dolastatins, dolastatin analogs such as auristatin, CPT-11 (irinotecan), mitozantrone, vinorelbine, teniposide, aminopterin, caminomycin, esperamicins (See, e.g., U.S. Pat. No. 4,675,187), neocarzinostatin, OK-432, bleomycin, furtulon, broxuridine, busulfan, honvan, peplomycin, bestatin (Ubenimex®), interferon-β, mepitiostane, mitobronitol, melphalan, laminin peptides, lentinan, *Coriolus versicolor* extract, tegafur/uracil, estramustine (estrogen/mechlorethamine).

Additional agents which may be used as therapy for cancer patients include EPO, G-CSF, ganciclovir; antibiotics, leuprolide; meperidine; zidovudine (AZT); interleukins 1 through 18, including mutants and analogues; interferons or cytokines, such as interferons alpha, beta, and gamma hormones, such as luteinizing hormone releasing hormone (LHRH) and analogues and, gonadotropin releasing hormone (GnRH); growth factors, such as transforming growth factor-β (TGF-β), fibroblast growth factor (FGF), nerve growth factor (NGF), growth hormone releasing factor (GHRF), epidermal growth factor (EGF), fibroblast growth factor homologous factor (FGFHF), hepatocyte growth factor (HGF), and insulin growth factor (IGF); tumor necrosis factor-α & β (TNF-α & β); invasion inhibiting factor-2 (IIF-2); bone morphogenetic proteins 1-7 (BMP 1-7); somatostatin; thymosin-alpha-1; gamma-globulin; superoxide dismutase (SOD); complement factors; anti-angiogenesis factors; antigenic materials; and pro-drugs. In addition, a BPTF inhibitor can be combined with a targeted agent, including but not limited to those targeting BRAF (vemurafenib or dabrafenib), MEK (trametinib), HER2 (e.g., herceptin), and EGFR (e.g., gefitinib). Other targeting combinations include a BPTF inhibitor and one or more of the following: Erbitux (cetuximab), Yervoy (ipilimumab) and pertuzumab. Examples of such therapies also include, by no way of limitation, small-molecule kinase inhibitors such as Imatinib (Gleevec), Sunitinib (Sutent), Sorafenib (Nexavar), Erlotinib (Tarceva), Dasatinib (Sprycel), Nilotinib (Tasigna), Lapatinib (Tykerb), Crizotinib (Xalkori), Ruxolitinib (Jakafi), Vandetanib (Caprelsa), Pazopanib (Votrient), afatinib, alisertib, amuvatinib, axitinib, bosutinib, brivanib, canertinib, cabozantinib, cediranib, crenolanib, dacomitinib, danusertib, dovitinib, foretinib, ganetespib, ibrutinib, iniparib, lenvatinib, linifanib, linsitinib, masitinib, momelotinib, motesanib, neratinib, niraparib, oprozomib, olaparib, pictilisib, ponatinib, quizartinib, regorafenib, rigosertib, rucaparib, saracatinib, saridegib, tandutinib, tasocitinib, telatinib, tivantinib, tivozanib, tofacitinib, vatalanib, veliparib, vismodegib, volasertib, BMS-540215, BMS777607, JNJ38877605, TKI258, GDC-0941 (Folkes, et al., J. Med. Chem. 2008, 51, 5522), BZE235, and others.

A prodrug refers to a precursor or derivative form of a pharmaceutically active substance that is less cytotoxic or non-cytotoxic to tumor cells compared to the parent drug and is capable of being enzymatically activated or converted into an active or the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, b-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use herein include, but are not limited to, those chemotherapeutic agents described above.

In some embodiments, the methods and compositions of the disclosure are particularly useful in breast cancer, brain cancer (glioblastoma multiforme), skin cancer, esophageal cancer, liver cancer, pancreatic cancer, prostatic cancer, uterine cancer, cervical cancer, lung cancer, bladder cancer, ovarian cancer, multiple myeloma and melanoma.

The disclosure also provides pharmaceutical compositions comprising one or more of the BPTF inhibitors described herein and a pharmaceutically acceptable carrier. In some embodiments the pharmaceutical compositions are prepared as injectables, either as liquid solutions or suspensions; solid forms suitable for solution in, or suspension in, liquid vehicles prior to injection can also be prepared. Liposomes are included within the definition of a pharmaceutically acceptable carrier. Pharmaceutically acceptable salts can also be present in the pharmaceutical composition, e.g., mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington: The Science and Practice of Pharmacy (1995) Alfonso Gennaro, Lippincott, Williams, & Wilkins.

The disclosure also provides methods for detecting BPTF. In some embodiments, BPTF can be detected in a patient in vivo or in a patient sample in vitro. In some embodiments the method comprises administering to a patient a composition comprising one or more BPTF inhibitors that bind to a BPTF polypeptide or nucleic acid and detecting the localization of the BPTF agent that is labeled with a detectable label in the patient. In some embodiments the patient sample comprises cancer cells. In some embodiments the BPTF inhibitor is linked to an imaging agent or is detectably labeled. In some embodiments, the BPTF inhibitor or binding agent is a BPTF antibody conjugated to an imaging agent and is administered to a patient to detect one or more tumors or to determine susceptibility of the patient to BPTF therapy. The labeled antibodies will bind to BPTF polypeptides in or on cells and thereby accumulate at a tumor site. Using standard imaging techniques, the site of the tumors can be detected.

The disclosure also provides methods of imaging/detecting cells or tumors expressing or overexpressing BPTF comprising contacting a composition comprising an agent (e.g., a nucleic acid or antibody) that binds to BPTF with a sample and detecting the presence of the BPTF in the sample. In some embodiments the sample is a patient sample. In some embodiments the patient sample comprises cancer cells.

Methods of detection are well known to those of skill in the art. For example, methods of detecting polynucleotides include, but are not limited to PCR, Northern blotting, Southern blotting, RNA protection, and DNA hybridization (including in situ hybridization). Methods of detecting polypeptides include, but are not limited to, Western blotting, ELISA, enzyme activity assays, slot blotting, peptide mass fingerprinting, electrophoresis, immunochemistry and immunohistochemistry. Other examples, of detection methods include, but are not limited to, radioimmunoassay (RIA), chemiluminescence immunoassay, fluoroimmunoassay, time-resolved fluoroimmunoassay (TR-FIA), two color fluorescent microscopy, or immunochromatographic assay (ICA), all well known by those of skill in the art. In some embodiments, polynucleotide expression is detected using PCR methodologies and polypeptide production is detected using ELISA technology.

Suitable probes for Northern blot hybridization of a given nucleic acid can be produced from the nucleic acid sequences of BPTF (e.g., SEQ ID NO:1). Methods for preparation of labeled DNA and RNA probes, and the conditions for hybridization thereof to target nucleotide sequences, are described in Molecular Cloning: A Laboratory Manual, J. Sambrook et al., eds., 2nd edition, Cold Spring Harbor Laboratory Press, 1989, Chapters 10 and 11.

In one example, the nucleic acid probe can be labeled with, e.g., a radionucleotide, such as $^3H$, $^{32}P$, $^{33}P$, $^{14}C$, or $^{35}S$; a heavy metal; or a ligand capable of functioning as a specific binding pair member for a labeled ligand (e.g., biotin, avidin or an antibody), a fluorescent molecule, a chemiluminescent molecule, or an enzyme. Probes can be labeled to high specific activity by nick translation, random priming, or other methods known to one of skill in the art. For example, by replacing preexisting nucleotides with highly radioactive nucleotides according to the nick translation method, it is known to prepare $^{32}P$-labeled nucleic acid probes with a specific activity well in excess of $10^8$ cpm/microgram.

Autoradiographic detection of hybridization can then be performed by exposing hybridized filters to photographic film. Densitometric scanning of the photographic films exposed by the hybridized filters provides an accurate measurement of miRNA transcript levels. In another embodiment, gene transcript levels can be quantified by computerized imaging systems, such the Molecular Dynamics 400-B 2D Phosphorimager available from Amersham Biosciences, Piscataway, N.J.

In another embodiment, the random-primer method can be used to incorporate an analogue, for example, the dTTP analogue 5-(N—(N-biotinyl-epsilon-aminocaproyl)-3-aminoallyl)deoxyuridine triphosphate, into the probe molecule. The biotinylated probe oligonucleotide can be detected by reaction with biotin-binding proteins, such as avidin, streptavidin, and antibodies (e.g., anti-biotin antibodies) coupled to fluorescent dyes or enzymes that produce color reactions.

In a further embodiment, determining the levels of an expression can be accomplished using the technique of in situ hybridization. This technique requires fewer cells than the Northern blotting technique, and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects. The practice of the in situ hybridization technique is described in more detail in U.S. Pat. No. 5,427,916, the disclosure of which is incorporated herein by reference.

The relative number of gene transcripts in cells can also be determined by reverse transcription of gene transcripts, followed by amplification of the reverse-transcribed transcripts by polymerase chain reaction (RT-PCR). The levels of gene transcripts can be quantified in comparison with an internal standard, for example, the level of mRNA from a "housekeeping" gene present in the same sample. A suitable "housekeeping" gene for use as an internal standard includes, e.g., myosin or glyceraldehyde-3-phosphate dehydrogenase (G3PDH). The methods for quantitative RT-PCR and variations thereof are within the skill in the art. In another embodiment, a high throughput stem loop real-time quantitative polymerase chain reaction (RT-qPCR) is used to detect miRNA expression. See Mestdagh et al., *Nucleic Acid Research* 36(21) (2008)).

An "expression profile" or "hybridization profile" of a particular sample is essentially a fingerprint of the state of the sample; while two states may have any particular gene similarly expressed, the evaluation of a number of genes simultaneously allows the generation of a gene expression profile that is unique to the state of the cell. That is, normal tissue may be distinguished from a cancer tissue, and within a cancer tissue, different prognosis states (good or poor long term survival prospects, for example) may be determined. By comparing expression profiles of a cancer tissue in different states, information regarding which genes are important (including both up- and downregulation of genes) in each of these states is obtained. The identification of sequences that are differentially expressed in a cancer tissue or normal tissue, as well as differential expression resulting in different prognostic outcomes, allows the use of this information in a number of ways. For example, a particular treatment regime may be evaluated (e.g., to determine whether a chemotherapeutic drug acts to improve the long-term prognosis in a particular patient). Similarly, diagnosis may be done or confirmed by comparing patient samples with the known expression profiles. Furthermore, these gene expression profiles (or individual genes) allow screening of drug candidates that suppress the cancer expression profile or convert a poor prognosis profile to a better prognosis profile.

According to the expression profiling methods described herein, total RNA from a sample from a subject suspected of having a cancer (e.g., melanoma, breast cancer, GBM) is quantitatively reverse transcribed to provide a set of labeled target oligodeoxynucleotides complementary to the RNA in the sample. The target oligodeoxynucleotides are then hybridized to a microarray comprising RNA-specific probe oligonucleotides to provide a hybridization profile for the sample. The result is a hybridization profile for the sample representing the expression pattern of genes in the sample. The hybridization profile comprises the signal from the binding of the target oligodeoxynucleotides from the sample to the BPTF-specific probe oligonucleotides in the microarray. The profile may be recorded as the presence or absence of binding (signal vs. zero signal). Typically the profile recorded includes the intensity of the signal from each hybridization. The profile is compared to the hybridization profile generated from a control sample. An alteration in the signal is indicative of a chemotherapy response in the subject.

Other techniques for measuring gene expression are also within the skill in the art, and include various techniques for measuring rates of RNA transcription and degradation, including Rnase Protection Assays, Nuclear run-ons, slot blotting, etc.

In another embodiment, the disclosure provides a method for prognosticating the presence of a cancer in a subject. The method comprises the step of determining whether or not BPTF is over-expressed or under-expressed in a biological sample from the subject, relative to the expression of BPTF from one or more control samples. In a particular embodiment, the level of over-expression of BPTF from a subject's biological sample in comparison to a control biological sample indicates whether the subject's sample is malignant. The cancer can be, for example, GBM, melanoma or breast cancer.

In yet another embodiment, the disclosure provides a method of determining the progression of cancer in a subject. The method comprises the step of measuring the expression level of BPTF from biological samples taken from patient having a cancer at various time points, such that the change in the expression level of BPTF between samples from the different time points indicates the progression or recovery from the cancer in the subject. In a particular embodiment, if the level of expression of BPTF is increasing between earlier and later time points this indicates that the subject's cancer is progressing to later stages of cancer. In an alternate embodiment, if the level of expression of BPTF is decreasing between earlier and later time points this indicates that the subject's cancer is in the process of remission. In a further embodiment, said cancer is melanoma, breast cancer or GBM.

In yet another embodiment, the disclosure provides a method of determining the survival rate of a subject with cancer. The method comprises the step of measuring the level of BPTF from biological samples taken from patient having a cancer at various time points, such that the change in the level of BPTF between samples from the different time points indicates a decreased or increased survival rate of the subject. In a particular embodiment, if the level of expression or over-expression of BPTF is increasing between earlier and later time points this would indicate that the subject's survival rate is decreasing. In an alternate embodiment, if the level of BPTF is decreasing between earlier and later time points this would indicate that the subject's survival rate is improving. In a further embodiment, said cancer is melanoma, breast cancer or GBM. The level of BPTF can be determined through protein detection, DNA detection techniques as well as measuring RNA expression.

In another embodiment, the disclosure provides a method of treating a cancer, the method comprising administering an effective amount of an agent that inhibits the expression or activity of BPTF.

The terms "treat", "treating" and "treatment", as used herein, refer to ameliorating symptoms associated with a disease or condition, for example, a melanoma, including preventing or delaying the onset of the disease symptoms, and/or lessening the severity or frequency of symptoms of the disease or condition. The terms "subject" and "individual" are defined herein to include animals, such as mammals, including but not limited to, primates, cows, sheep, goats, horses, dogs, cats, rabbits, guinea pigs, rats, mice or other bovine, ovine, equine, canine, feline, rodent, or murine species. In a preferred embodiment, the mammal is a human.

As used herein, an "effective amount" of BPTF inhibitor is an amount sufficient to inhibit proliferation or invasiveness of a cancer cell in a subject suffering from a cancer. One skilled in the art can readily determine an effective amount of a BPTF inhibitor to be administered to a given subject, by taking into account factors, such as the size and weight of the subject; the extent of disease penetration; the age, health and sex of the subject; the route of administration; and whether the administration is regional or systemic.

Cancers that may be treated by compositions comprising polynucleotides comprising inhibitory BPTF agents and/or agents that decrease BPTF expression, include, tumors that are not vascularized, or not yet substantially vascularized, as well as vascularized tumors. The cancers may be comprised of non-solid tumors (such as leukemias and lymphomas) or may be solid tumors.

In a particular embodiment, the disclosure provides a method of treating cancer, such as melanoma, breast cancer or GBM, in a subject, the method comprising administering an effective amount of an agent that inhibits the expression or activity of BPTF. In another embodiment, the agent is a shRNA. In another embodiment, the agent is a double-stranded miRNA mimic. miRNA mimic technology is well known in the art. See e.g., Wang, Z., 2009, miRNA mimic technology, In MicroRNA Interference Technologies, pages 93-100, Springer-Link Publications. In another embodiment, the agent is an oligonucleotide based BPTF drug.

Expression vectors encoding shRNA or miRNA molecules to BPTF can be delivered to cells of a subject for the treatment or prevention of a cancer. The nucleic acid molecules are delivered to the cells of a subject in a form in which they can be taken up and are advantageously expressed so that therapeutically effective levels can be achieved. Expression vectors that are able to express BPTF shRNA are commercially available from various vendors.

Methods for delivering polynucleotides comprising inhibitory nucleic acid agents that decrease BPTF expression to the cell include using a delivery system, such as liposomes, polymers, microspheres, gene therapy vectors, modified nucleic acids (e.g., charge neutralized nucleic acids) and naked DNA vectors.

Transducing viral (e.g., retroviral, adenoviral, lentiviral and adeno-associated viral) vectors can be used for somatic cell gene therapy, especially because of their high efficiency of infection and stable integration and expression (see, e.g., Cayouette et al., *Human Gene Therapy* 8:423-430 (1997); Kido et al., *Current Eye Research* 15:833-844 (1996); Bloomer et al., *Journal of Virology* 71:6641-6649 (1997); Naldini et al., *Science* 272:263-267 (1996); and Miyoshi et al., *Proc. Natl. Acad. Sci. U.S.A.* 94:10319 (1997)). For example, a polynucleotide encoding an inhibitory nucleic acid to BPTF can be cloned into a retroviral vector and its expression can be driven from an endogenous promoter, from the retroviral long terminal repeat, or from a promoter specific for a target cell type of interest. Other viral vectors that can be used include, for example, a vaccinia virus, a bovine papilloma virus, or a herpes virus, such as Epstein-Barr Virus (also see, for example, the vectors of Miller, *Human Gene Therapy* 15-14, (1990); Friedman, *Science* 244:1275-1281 (1989); Eglitis et al., *BioTechniques* 6:608-614 (1988); Tolstoshev et al., *Current Opinion in Biotechnology* 1:55-61 (1990); Sharp, *The Lancet* 337:1277-1278 (1991); Cornetta et al., *Nucleic Acid Research and Molecular Biology* 36(31):1-322 (1987); Anderson, *Science* 226:401-409 (1984); Moen, *Blood Cells* 17:407-416 (1991); Miller et al., *Biotechnology* 7:980-990 (1989); Le Gal La Salle et al., *Science* 259:988-990 (1993); and Johnson, *Chest* 107:77S-83S (1995)). Retroviral vectors are particularly well developed and have been used in clinical settings (Rosenberg et al., *N. Engl. J. Med* 323:370 (1990); Anderson et al., U.S. Pat. No. 5,399,346; Gruber et al., U.S. Pat. Publ. No. 2011/0287020A1). Non-viral approaches can also be employed for the introduction of an inhibitory nucleic acid to BPTF based therapeutic to a cell of a patient diagnosed as having a neoplasia. For example, a polynucleotide comprising an inhibitory nucleic acid to BPTF can be introduced into a cell by administering the nucleic acid in the presence of cationic lipid (Feigner et al., *Proc. Natl. Acad. Sci. U.S.A.* 84:7413 (1987); Ono et al., *Neuroscience Letters* 17:259 (1990); Brigham et al., *Am. J. Med. Sci.* 298:278 (1989); and Staubinger et al., *Methods in Enzymology* 101:512 (1983)); asialoorosoinucoid-polylysine conjugation (Wu et al. *Journal of Biological Chemistry* 263:14621 (1988); Wu et al., *Journal of Biological Chemistry* 264:16985 (1989); or by micro-injection under surgical conditions (Wolff et al., *Science* 247:1465 (1990). A polynucleotide comprising an inhibitory nucleic acid to BPTF and/or an agent that inhibits BPTF expression can be administered in combination with a liposome and protamine.

In another embodiment, the disclosure provides therapeutic compositions comprising polynucleotides comprising an inhibitory nucleic acid to BPTF that inhibit the expression of BPTF for the treatment of a cancer, such as melanoma. In another embodiment, the disclosure provides a pharmaceutical composition comprising an agent that inhibits the expression of BPTF.

Polynucleotides comprising an inhibitory nucleic acid to BPTF and/or agents that inhibit the expression of BPTF may be administered as part of a pharmaceutical composition. The pharmaceutical composition is preferably sterile and contains a therapeutically effective amount of a polynucleotide molecule comprising an inhibitory BPTF nucleic acid and/or an agent that inhibits the expression of BPTF in a unit of weight or volume suitable for administration to a subject.

The therapeutic polynucleotide molecule comprising an inhibitory BPTF nucleic acid and/or agents that inhibit the expression of BPTF may be administered with a pharmaceutically-acceptable carrier, in unit dosage form. Conventional pharmaceutical practice may be employed to provide suitable formulations or compositions to administer the compounds to patients suffering from a cancer.

Carrier as used herein includes pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt forming counterions such as sodium; and/or nonionic surfactants such as TWEEN™, polyethylene glycol (PEG), and PLURONICS™.

Polynucleotides comprising an inhibitory BPTF nucleic acid and/or agents that inhibits the expression of BPTF may also be entrapped in microcapsules prepared, for example, by interfacial polymerization, for example, hydroxymethylcellulose or gelatin-microcapsules and poly(methylmethacylate) microcapsules, respectively, in colloidal drug delivery systems (for example, liposomes, albumin microspheres, microemulsions, nano-particles, and nanocapsules) or in macroemulsions. The formulations to be used for in vivo administration must be sterile. This is readily accomplished by filtration through sterile filtration membranes. Sustained-release preparations may be prepared. Suitable examples of sustained-release preparations include semipermeable matrices of solid hydrophobic polymers comprising a polynucleotide comprising an inhibitory BPTF nucleic acid and/or an agent which inhibits BPTF expression, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release of molecules for shorter time periods.

In another embodiment, the pharmaceutical compositions comprising polynucleotides comprising an inhibitory BPTF nucleic acid and/or agents that inhibits the expression of BPTF are administered in conjunction with other therapeutic agents. "Conjunction" with respect to administering other therapeutic agents, refers to agents that may administered prior to, concurrently, or subsequent to pharmaceutical compositions comprising polynucleotides comprising an inhibitory BPTF nucleic acid and/or agents which inhibit BPTF expression.

In another embodiment, the disclosure provides a kit for determining a subject likelihood of having cancer and/or progression of cancer, said kit comprising: a) an oligonucleotide complementary to BPTF; and b) optionally, reagents for the formation of the hybridization between said oligonucleotide and BPTF. In another embodiment, the kit optionally includes directions for monitoring the nucleic acid molecule levels of a marker in a biological sample derived from a subject. In another embodiment, the kit comprises a sterile container which contains the primer, probe, or other detection regents; such containers can be boxes, ampoules, bottles, vials, tubes, bags, pouches, blister-packs, or other suitable container form known in the art. Such containers can be made of plastic, glass, laminated paper, metal foil, or other materials suitable for holding nucleic acids. The instructions will generally include information about the use of the primers or probes described herein and their use in diagnosing a cancer. Preferably, the kit further comprises any one or more of the reagents described in the diagnostic assays described herein. In other embodiments, the instructions include at least one of the following: description of the primer or probe; methods for using the enclosed materials for the diagnosis of a cancer; precautions; warnings; indications; clinical or research studies; and/or references. The instructions may be printed directly on the container (when present), or as a label applied to the container, or as a separate sheet, pamphlet, card, or folder supplied in or with the container.

In another embodiment, the disclosure provides an apparatus for determining the expression levels of BPTF, said apparatus comprising a solid support, wherein a surface of said solid support is linked to an oligonucleotide complementary to BPTF. In one embodiment, the apparatus is a micro-array. The examples of solid support include, but are not limited to, a glass or nitro-cellulose slide that is used to bind nucleic acids.

The following examples are intended to illustrate but not limit the disclosure. While they are typical of those that might be used, other procedures known to those skilled in the art may alternatively be used.

EXAMPLES

Cell Culture and Transfection.
C8161.9 and 1205-Lu human melanoma and B16-F10 murine melanoma cells were obtained as described (Bagheri et al., 2006; Dar et al., 2011). U251 and LN18 glioblastoma cell lines were purchased from ATCC (Manassas, Va.). C8161.9 cells were grown in DMEM/F12 with 5% fetal bovine serum (FBS) (Invitrogen Life Technologies, Carlsbad, Calif.); 1205-Lu cells were grown in TU2% medium; and B16-F10 cells were grown in RPMI-1640 with 5% FBS. U251 and LN18 were grown in DMEM with 5% FBS. All cells were grown at 37° C. in an atmosphere containing 5% $CO_2$. Transient transfection was carried out by Lipofectamine-2000 (Invitrogen Life Technologies, Carlsbad, Calif.) according to the manufacturer's protocol.

Plasmids.
Plasmids pcMV6-BPTF, pcMV6-Entry and BPTF targeting shRNA vector set (4 clones) pGFP-V-RS were purchased from Origene (Origene Technologies Rockville Md.). BPTF shRNA 1 and BPTF shRNA 2 were used from this set for the murine cell line. The lentiviral-based shRNA vector set (5 clones) targeting BPTF (RHS4533_NM_0059, incorporated herein by reference) was purchased from Openbiosystems (Lafayette, Colo.).

RNA Extraction and cDNA Synthesis.
RNA extraction and cDNA synthesis were performed using techniques common in the art.

Quantitative Real-Time PCR (qRT-PCR).
mRNAs were assayed using the TaqMan Gene Expression Assays in accordance with the manufacturer's instructions (Applied Biosystems). TaqMan probes for BPTF, HPRT1, CCND2, BCL-XL, TWIST1, RAB14, CEBPB, CHI3L1, DLL3, OLIG2, PDGFRA and BCL2 were purchased from Applied Biosystems (Foster City, Calif.).

Cell Viability, Colony Formation, Cell Cycle Analyses, and BRAF Inhibitor Treatment.
Cell viability and colony formation were performed and cell cycle analysis was performed as described using common techniques in the art. Cells were treated with varying concentrations of vemurafenib for 72 hrs or dabrafenib (Chemitek, Indianapolis, Ind.) for 48 hrs or as indicated. DMSO was used as a vehicle.

Western Blot Analysis.
Western blot analysis was performed. Target proteins were detected by using specific antibodies against BPTF (Bethyl Laboratories Montgomery, Tex.), BCL2, and GAPDH (Santa Cruz Biotechnology, Santa Cruz, Calif.), and ERK1/2, pERK1/2, CCND2, BCL-XL, p90RSK (Cell Signaling Technology, Danvers, Mass.).

Lentiviral Transduction and Stable Cell Generation.
Selected shRNAs cloned into the pLKO1-vector were co-transfected into 293T cells along with expression vectors containing the GAG/POL, REV and VSVG genes. Lentiviruses were harvested 48 hrs after transfection. Sub-confluent human melanoma or glioblastoma cells were infected with each harvested lentiviruses in the presence of 8 µg/ml of polybrene, and were selected in 1 µg/ml of puromycin at 48 hrs post-infection in their respective culture medium. B16-

F10 cells were transfected with BPTF shRNA1, BPTF shRNA 2 or Neg shRNA vectors and stable transformants were selected with 2 ug/ml of puromycin.

Invasion Assays.

A Matrigel assay for tumor invasion was performed using routine techniques. For B16-F10, 1205-Lu and C8161.9 cells, insert chambers were coated with 15 µl matrigel at 6 mg/ml protein, 17 µl and 7 mg/ml for C8161.9 cells and 15 µl and 5 mg/ml for 1205-Lu and U251 cell lines.

Quantification of DNase I Sensitivity.

Cells were harvested and resuspended in ice-cold lysis buffer (100 mM KCL, 50 mM Tris-CL [pH 7.9], 50% [vol/vol] glycerol, 200 mM β-mercaptoethanol, and 5 mM $MgCl_2$) and incubated for 10 minutes. Nuclei were recovered from the lysed cells by subjecting the suspension to centrifugation at 13,000 g for 15 minutes at 4° C. and resuspending the cells in Buffer A (50 mM Tris-Cl [pH 7.9], 3 mM $MgCl_2$, 0.2 mM phenylmethylsulfonyl fluoride, 100 mM NaCl, and 1 mM dithiothreitol). Nuclei were digested with DNase I for 3 minutes at room temperature in Buffer A. The samples were then treated with proteinase K and the DNA was recovered using the QIAGEN PCR purification kit (Qiagen, Valencia, Calif.). DNase-treated DNA was subjected to qPCR using specific primers for BCL2 and BCL-XL.

Tissue Arrays and Immunostaining.

The tissue microarrays utilized were previously created using core diameters of 1.0 mm taken from the paraffin blocks. Slides were prepared from formalin-fixed tissue microarrays and stained with anti-human BPTF antibody at a 1:100 dilution (Bethyl Laboratories Montgomery, Tex.). Microwave antigen retrieval was conducted in 10 mM citrate buffer, pH 6.0. Endogenous peroxidase was blocked with 3% $H_2O_2$, and additional blocking was performed with normal rabbit serum. The primary antibody was diluted in 1.0% BSA in PBS and applied overnight at 4° C. Antibody staining was observed by using biotin-labeled anti-goat IgG and avidin-biotin (Vector Laboratories, Burlingame, Calif.) followed by diaminobenzidine. Sections were counterstained with hematoxylin.

Digital Evaluation of Immunohistochemical Staining.

The whole slide image of tissue microarray sections was captured using a Mirax MIDI high-resolution scanning system (Carl Zeiss Micro Imaging, Jena, Germany). The digitization process was controlled via software using a Marlin CCD Camera (Allied Vision Technologies GmbH, Germany) with a Zeiss Plan-Apopchromat 20x/0.8NA objective (Carl Zeiss Optronics GmBh, Oberkochen, Germany) to generate images at a resolution of 0.32 microns/pixel. Regions with an identifiable melanocytic lesion were selected for evaluation, and immunohistochemical staining was calculated by applying a segmentation feature with two different phase measurement masks recognizing nuclei (hematoxylin-stained) and cytoplasm (brown-immunostained). Image analysis was performed by computer-assisted color segmentation to determine the percentage of positive color-expressing pixels. For each positive pixel, the intensity (defined as the average of red, green and blue color values) was calculated for subsequent analysis. Statistical methods used to assess the significance of various prognostic factors on melanoma outcome were previously described (Bagheri et al., 2006).

Gene Expression Profiling.

Total RNA was extracted from cells using the RNeasy kit (Qiagen, Valencia, Calif.). Ten micrograms of total RNA, along with universal mouse reference RNA (Stratagene, Santa Clara, Calif.), was converted to aminoallyl-modified cDNA by oligo(dT)-primed polymerization using SuperScript II reverse transcriptase (Invitrogen), coupled to N-hydroxysuccinimidyl esters of Cy3 or Cy5 (Amersham Pharmacia, Pittsburgh, Pa.), and then hybridized to a microarray slide as described (Haqq et al., 2005). After linear normalization, log (base 2) transformation, and supervised hierarchical clustering, the resulting cluster data table was imported into the significance analysis of microarrays software package. Delta was chosen to limit the output gene list so that 5% predicted false positives would be included.

FISH and Microscopy.

BAC clones RP11-304I14, RP11-1134M2, RP11-29C18 and CTD-2314M10 were used to detect the BPTF locus on 17q24.3 (February 2009 freeze of the UCSC Genome Browser, http://genome.ucsc.edu). All clones were obtained from the Children's Hospital of Oakland Research Institute (CHORI). BAC DNA was prepared with the Large-Construct kit (Qiagen, Valencia, Calif.) and labeled by nick translation with Alexa Fluor 488 dUTP's (Molecular Probes, Green Island, N.Y.) as described (Wiegant and Raap, 2001). The quality and mapping of all probes was verified by hybridization to normal metaphase spreads in combination with a commercially available centromeric probe for chromosome 17 (Openbiosystems, Lafayette, Colo.), before tissue analysis. Hybridization on tissue sections was performed as described previously (Wiegant and Raap, 2001). Images were taken with a Zeiss Axio Imager Z2 controlled by Axiovision software (Zeiss, Jena, Germany).

Analysis of FISH Results.

The FISH signals were assessed and counted manually from images with several Z stack layers. A minimum of 30 nuclei from each case were evaluated and the signals were interpreted according to guidelines described previously (Munne et al., 1998) and were recorded as 2, 3, 4, or greater.

Animal Studies.

All animal care was in accordance with institutional guidelines and a protocol that was approved by the University of California San Francisco Committee on Animal Research and California Pacific Medical Center Research Institute. Groups of 45-day-old female C57B1/6 (Charles River) were inoculated by tail vein injection with 30,000 B16-F10 BPTF stables cells. $1\times10^6$ 1205-Lu cells were injected by tail vain in nude mice. For subcutaneous injection $1\times10^6$ 1205-Lu, B16-F10, or C8161.9 cells and $2\times10^6$ U251 cells were injected, respectively.

Statistical Analysis.

All quantified data represents an average of at least triplicate samples or as indicated. Error bars represent standard deviation of the mean. Statistical significance was determined by the Student's t-test or Mann-Whitney test and two-tailed p values <0.05 were considered significant.

BPTF Knockdown Suppresses Proliferation, In Vivo Growth, and Metastatic Potential of Murine Melanoma.

The functional role of BPTF in melanoma was initially assessed using shRNA-mediated targeting in the B16-F10 murine melanoma model. BPTF expression was suppressed significantly by two different anti-BPTF shRNAs (1 and 2) as determined by quantitative real-time PCR (qRT-PCR) (FIG. 1A). ShRNA-mediated suppression of BPTF expression substantially suppressed the proliferative ability of B16-F10 cells when compared to a control shRNA (FIG. 1B). BPTF shRNA-expressing cells also exhibited significantly reduced invasion into Matrigel®, when compared to control shRNA-expressing cells (FIG. 7A). Subcutaneous injection of BPTF shRNA-expressing cells showed a significant suppression in tumor cell growth (FIG. 1C). Intravenous inoculation of BPTF shRNA in C57B1/6 mice showed a highly significant reduction in metastatic tumor count in the lungs (FIG. 1D). These results demonstrate a significant role for BPTF in the proliferative and metastatic potential of melanoma.

Due to the uncharacterized role of BPTF in cancer, cDNA microarray analyses were performed to identify the global patterns of gene expression following suppression of BPTF expression. cDNA microarray analysis was performed on B16-F10 clones stably expressing BPTF shRNA 2 vs. the control vector. Analysis of microarrays identified downregulation of expression of 27 genes, as well as overexpression of 1008 genes. The downregulated genes included Bcl-xl and Ccnd2, key mediators of tumor cell proliferation and apoptosis. The differential expression of these genes (as well as Bcl-2) in B16-F10 melanoma was confirmed by qRT-PCR and by western blot analysis (FIG. 1E-F).

BPTF Knockdown Suppresses Proliferation, In Vivo Growth and Metastatic Potential of Human Melanoma.

Having demonstrated a functional role for BPTF in murine melanoma cells, the role in the progression of human melanoma was analyzed. Targeting BPTF using a different shRNA (BPTF shRNA 3) than those used for the murine studies resulted in significant suppression of BPTF expression in 1205-Lu human melanoma cells, which harbor mutant BRAF (FIG. 2A). Suppression of BPTF led to G1/G0 cell cycle arrest and a significant reduction in S-phase when compared to the control shRNA vector (FIG. 2B). BPTF knockdown had a significant effect on the proliferative ability of melanoma cells, as evidenced by the suppression of cell survival (FIG. 2C) and colony formation ability (FIG. 2D, $p<0.02$), and was accompanied by significantly increased apoptotic index of 1205-Lu cells (FIG. 2E, $p<0.02$). Similar effects on melanoma cell proliferation and survival were observed using two other shRNAs targeting human BPTF. Suppression of BPTF also led to a significant decrease in 1205-Lu invasiveness into Matrigel® (FIG. 7B). Subcutaneous tumor cell growth in nude mice was considerably suppressed in BPTF shRNA-expressing cells when compared to control shRNA-expressing cells (FIG. 2F). Finally, suppression of BPTF expression resulted in 66% reduction in the metastatic tumor burden in the lungs of nude mice upon intravenous inoculation of 1205-Lu cells (FIG. 2G). These antitumor effects were confirmed following shRNA-mediated suppression of BPTF in the highly aggressive C8161.9 melanoma cell line, which harbors wild type BRAF (FIG. 8A-E). Taken together, these studies demonstrate that BPTF plays an important role in promoting the proliferative and metastatic potential of both BRAF-wild type and mutant melanoma cell lines.

BPTF Regulates the Expression of BCL2, BCL-XL, CCND2, and the ERK1/2 Pathway.

FAC1, the truncated form of BPTF, exhibits sequence-specific DNA binding activity. Analysis of the promoter regions of BCL2 and BCL-XL indicated the presence of possible consensus sequences for BPTF. The sensitivity DNase I treatment in the promoter regions of these genes was assessed in two human melanoma cell lines stably expressing control versus BPTF shRNA. DNase I hypersensitivity may be due to transcription factor binding or changes in nucleosome positioning or packing (Gross and Garrard, 1988). Using qPCR analysis, the DNA regions containing the putative BPTF binding sites within the BCL2 and BCL-XL were quantitated, and were found to be present at substantially reduced levels in both 1205-Lu and C8161.9 human melanoma cells expressing BPTF shRNA (FIG. 3A-B). Thus, the promoter regions of BCL2 and BCL-XL exhibited increased sensitivity to DNase I treatment in human melanoma cells with reduced BPTF expression. It was then confirmed that the downregulation of these genes at the mRNA level in human melanoma cells following BPTF shRNA expression (FIG. 3C-D). As these genes mediate pro-survival pathways, the proliferative signaling pathways regulated by BPTF expression were examined, and a substantial suppression in levels of pERK1/2 (Thr202/Tyr204) in BPTF shRNA-expressing melanoma cells was observed (FIG. 3E-F). p90RSK (Ser380), the downstream target of pERK, was also suppressed by BPTF knockdown. BCL2 and BCL-XL, which represent additional effectors of the ERK pathway (Boucher et al., 2000), were also modulated by BPTF knockdown, in addition to CCND2, in 1205-Lu and C8161.9 human melanoma cells (FIG. 3E-F). Overexpression of either ERK1/2 or BCL-XL cDNA in melanoma cells stably-expressing BPTF shRNA reversed the suppression in cell survival following BPTF knockdown, indicating that the pro-proliferative function of BPTF is mediated, at least in part, by ERK1/2 and BCL-XL (FIG. 9).

Conversely, overexpression of BPTF in 1205-Lu cells resulted in significantly increased proliferative capacity (FIG. 10A), and was accompanied by upregulation in expression of CCND2, BCL-XL and BCL2 at the mRNA and protein levels (FIG. 10B-C).

Quantitation of BPTF Levels in Melanocytic Neoplasms.

Having determined functional roles for BPTF in promoting murine and human melanoma proliferation and metastasis, immunohistochemical analysis of BPTF expression was performed on a tissue microarray cohort of 311 human melanoma patients (Rangel et al., 2006), and quantitated BPTF levels (FIG. 11) using a digital imaging analysis (Kashani-Sabet et al., 2009). By Kaplan-Meier analysis, high levels of BPTF expression were significantly predictive of reduced distant metastasis-free survival (DMFS, $p=0.03$, FIG. 4A) and disease-specific survival (DSS, $p=0.008$, FIG. 4B). By multivariate Cox regression analysis, increasing BPTF expression was an independent predictor of DMFS (Table 1) and DSS (Table 2). Thus, BPTF overexpression directly correlated with the development of distant metastasis and with reduced survival in human melanoma, and was an independent predictor of survival.

TABLE 1

Multivariate Cox regression analysis of impact of various prognostic factors on distant-free survival of melanoma cohort.

| Prognostic factor | Chi-square | Risk Ratio | P value |
| --- | --- | --- | --- |
| Tumor thickness | 12.3 | 1.51 | .0005 |
| BPTF expression level | 7.64 | 1.01 | .0057 |
| Ulceration | 4.72 | 1.57 | .03 |
| Mitotic rate | 4.35 | 1.05 | .037 |
| Site | 1.25 | 1.25 | .26 |
| Sex | .1 | .98 | .75 |
| Age | 0.30 | 1.12 | .59 |

TABLE 2

Multivariate Cox regression analysis of impact of various prognostic factors on disease-specific survival of melanoma cohort.

| Prognostic factor | Chi-square | Risk Ratio | P value |
| --- | --- | --- | --- |
| Tremor thickness | 12.4 | 1.56 | .0004 |
| BPTF expression level | 7.49 | 1.01 | .0062 |
| Mitotic rate | 5.26 | 1.06 | .02 |
| Ulceration | 2.85 | 1.46 | .09 |
| Site | 0.30 | 1.12 | .58 |

TABLE 2-continued

Multivariate Cox regression analysis of impact of various prognostic factors on disease-specific survival of melanoma cohort.

| Prognostic factor | Chi-square | Risk Ratio | P value |
|---|---|---|---|
| Sex | 0.01 | .98 | .92 |
| Age | 0.19 | 1.03 | .66 |

To determine BPTF copy number in melanoma, interphase fluorescence in situ hybridization (FISH) was performed on 81 benign nevus samples and 77 primary melanomas. All nevi had 2 copies of the BPTF gene, whereas 64% of the melanomas had more than 2 copies (2 to 2.9 copies), 22% had more than 3 copies (3 to 3.9 copies) and 14% had more than 4 copies, (Table 3). FIG. 4C-D shows representative FISH photomicrographs illustrative of low and high BPTF copy number. These findings indicate that the BPTF copy number is elevated in a significant proportion of primary melanomas, further supporting its oncogenic role.

TABLE 3

BPTF copy number for Melanoma and Nevi samples.

| Copy Number | Cases | % |
|---|---|---|
| Nevi | | |
| 2 | 81 | 100 |
| Melanoma | | |
| 2 | 49 | 64 |
| 3 | 17 | 22 |
| 4 | 11 | 14 |

BPTF Regulates Sensitivity to Selective BRAF Inhibitors.

ERK1/2 is a downstream target of BRAF within the MAP kinase pathway, and is significantly suppressed following treatment with selective BRAF inhibitors (Greger et al., 2012; Joseph et al., 2010). Given the downregulation of activated ERK1/2 following shRNA-mediated suppression of BPTF in human melanoma cells, the level of BPTF expression was assessed to determine the sensitivity to selective BRAF inhibitors. BPTF shRNA-expressing 1205-Lu cells were 3.2-fold more sensitive to vemurafenib treatment (FIG. 5A), and 2.8-more sensitive to dabrafenib treatment (FIG. 5B), when compared to control shRNA-expressing cells. Conversely, overexpression of BPTF in 1205-Lu cells significantly reduced their sensitivity to vemurafenib or dabrafenib treatment (2.5 to 3.4 fold, respectively) (FIG. 5C-D). The regulation of sensitivity of human melanoma cells to selective BRAF inhibition following modulation of BPTF expression was confirmed in the BRAF-mutant expressing LOX cell line (FIG. 12).

In addition, samples acquired from eight metastatic melanoma patients prior to initiation of and following progression to the selective BRAF inhibitors vemurafenib or dabrafenib were subjected to genotyping, immunohistochemical staining and FISH analysis. Five patients were treated with vemurafenib and three with dabrafenib. Following acquired resistance to targeted therapy, five patients had wild type NRAS and three had heterozygous NRAS mutation (codon-61). In a patient treated with vemurafenib, immunohistochemical analysis of BPTF expression indicated that, while BPTF expression was homogeneous in a metastatic specimen prior to BRAF inhibitor treatment, in the progressing specimen BPTF expression was heterogeneous, with one clone of cells with absent BPTF expression (suggestive of cells responding to treatment) and another clone of cells with high levels of BPTF expression (suggestive of cells resistant to treatment) (FIG. 5E-F). Immunohistochemical analysis using antibodies targeting the melanocyte antigens MART1, HMB45 and tyrosinase revealed positive staining in both of these regions (FIG. 5G), confirming the melanocytic lineage of these cells. TUNEL staining identified many of the cells expressing little or no BPTF expression as having undergone apoptosis. FISH analysis revealed heterogeneity in BPTF copy number in the progressing specimen (FIG. 5H). In addition, there was an increase in mean BPTF copy number (from $2.6\pm1.9$ to $3.5\pm2.5$) when comparing the pre-treatment and progressing specimens. Similar findings are shown in specimens from a patient treated with vemurafenib (FIG. 13). Overall, six (75%) out of the eight patients' post-treatment tumor were characterized by heterogeneity of BPTF expression. Taken together, these results suggest that increased levels of BPTF can mediate acquired resistance to selective BRAF inhibitors in melanoma patients, and can be selected for during the development of acquired resistance to these agents.

BPTF Promotes Glioblastoma Progression.

Examination of whether BPTF was involved in the progression of other solid tumors was performed. As melanocytes are derived from the embryonic neural crest, and as BPTF expression is abundant in the human fetal brain (Bowser et al., 1995), experiments were performed that were aimed to determine the functional role of BPTF in the progression of GBM, which is also of neuroectodermal origin. Stable suppression of BPTF expression by BPTF shRNA 3 (FIG. 6A) in U251 human GBM cells resulted in significantly reduced proliferation, as determined by assays of cell survival (FIG. 6B) and colony formation (FIG. 6C). Suppression of BPTF expression led to a significant G1/G0 cell cycle arrest, with a concomitant suppression in the S-phase (FIG. 6D, $p<0.01$), and in the induction of apoptosis (FIG. 6E, $p<0.02$). BPTF suppression also significantly reduced the invasiveness of U251 cells (FIG. 7C). BPTF knockdown resulted in suppression of the expression of BCL2, BCL-XL and CCND2 in GBM cells (FIG. 6F-G), accompanied by a significant suppression in phosphorylated ERK1/2 and p90RSK (FIG. 6G). In vivo studies showed a highly significant reduction in U251 tumor cell growth following subcutaneous inoculation upon BPTF suppression (FIG. 6H). Similar effects were observed following suppression of BPTF cells in LN18 cells (FIG. 14). Thus, these results demonstrate a functional role for BPTF in promoting glioblastoma progression by activating genes and pathways similar to those identified in melanoma cells.

Finally, the molecular subtypes of GBM in which BPTF expression is enriched were identified. Analysis of the TCGA data set revealed BPTF overexpression to occur most commonly in the pro-neural subset of GBMs (Verhaak et al., 2010). In order to confirm this observation, BPTF expression levels were observed in an independent sample of 14 GBMs that were classified as either pro-neural or mesenchymal by virtue of expression of several established classification markers (the mesenchymal markers CEBPB, CHI3L1 TWIST1, and the pro-neural markers, DLL3, OLIG2 and PDGFRA). BPTF expression (as determined by qRT-PCR analysis) was significantly higher in the pro-neural versus the mesenchymal subset of GBMs (FIG. 6I).

A number of embodiments have been described herein. Nevertheless, it will be understood that various modifications may be made without departing from the spirit and scope of this disclosure. Accordingly, other embodiments are within the scope of the following claims.

What is claimed is:

1. A method of treating a cancer in a subject, the method comprising:
   inhibiting the expression of BPTF by administering an effective amount of an inhibitory BPTF nucleic acid and/or an effective amount of an agent that inhibits the expression of BPTF in a cancer cell, wherein the cancer is selected from the group consisting of melanoma and breast cancer.

2. The method of claim 1, wherein the inhibiting of the expression of BPTF results in inhibiting or preventing the proliferation or migration of cancer cells.

3. The method of claim 1, wherein the method is used in combination with one or more additional anti-cancer therapeutic agents.

4. The method of claim 3, wherein the one or more additional therapeutic agents are selected from the group consisting of platinum analogs, alkylating agents, alkyl sulfonates, androgens, anti-adrenals, anti-androgens, antibiotics, anti-estrogens, aromatase inhibiting 4(5)-imidazoles, anti-metabolites, folic acid analogues, ethylenimines and methylamelamines, folic acid replenishers, nitrogen mustards, nitrosureas, purine analogs, pyrimidine analogs, topoisomerase inhibitors, thymidylate synthase inhibitors, anti-cancer antibodies, chemotherapeutics, de-methylation agents, and targeted therapeutic agents.

5. The method of claim 1, wherein the method comprises administering a vector comprising an inhibitory BPTF nucleic acid to the subject.

6. The method of claim 5, wherein the vector comprises an expression vector.

7. The method of claim 5, wherein the vector comprises a replication competent retroviral vector.

* * * * *

SEQUENCE LISTING

<160> NUMBER OF SEQ ID NOS: 5

<210> SEQ ID NO 1
<211> LENGTH: 9700
<212> TYPE: DNA
<213> ORGANISM: Homo sapiens
<220> FEATURE:
<221> NAME/KEY: CDS
<222> LOCATION: (472)..(8817)

<400> SEQUENCE: 1

```
agccgccact gcgtccggcc ctccccgtca gctttcccct ctcccgccgc ctgggctcca      60
acaagagggg ccggcggggc aggccgacca agcagcccgc ggctcccgct gcggagcgct     120 gcgcccggc  cccgccgccg ccgccgccca cgtccggacc catcggggc  tcccctcgcc     180 gatacgcggt agtagccggg gcaggtgggc agccgccagg ctgaggtggc gcccaagacg     240
cggctgagct cgcccagggt gggcagcagt agccggagga agccgccgcc gccgccgccg     300 gccccccca  gcaccagcgc cccgggccgg ggggggcgag gaggcggggg cggcacgacg     360 ggggcgggg  gcgcggcgg  ccacctgtcc cggaccaccg cggcccggag ggccgtcaac     420
aaagtggtgt acgatgacca cgagagcgag gcggtggagg aagaggagga c atg gtc    477
                                                         Met Val
                                                           1
```

| | | | | | | | | | | | | | | | | |
|---|---|---|---|---|---|---|---|---|---|---|---|---|---|---|---|---|
| tcc | gag | gag | gag | gag | gag | gag | gac | ggc | gac | gcc | gag | gag | acc | cag | gat | 525 |
| Ser | Glu | Glu | Glu | Glu | Glu | Glu | Asp | Gly | Asp | Ala | Glu | Glu | Thr | Gln | Asp | |
| | 5 | | | | 10 | | | | | 15 | | | | | | |

| | | | | | | | | | | | | | | | | |
|---|---|---|---|---|---|---|---|---|---|---|---|---|---|---|---|---|
| tct | gag | gac | gac | gag | gag | gat | gag | atg | gaa | gag | gac | gac | gat | gac | tcc | 573 |
| Ser | Glu | Asp | Asp | Glu | Glu | Asp | Glu | Met | Glu | Glu | Asp | Asp | Asp | Asp | Ser | |
| | 20 | | | | | 25 | | | | | 30 | | | | | |

| | | | | | | | | | | | | | | | | |
|---|---|---|---|---|---|---|---|---|---|---|---|---|---|---|---|---|
| gat | tat | ccg | gag | gag | atg | gaa | gac | gac | gac | gac | gac | gcc | agt | tac | tgc | 621 |
| Asp | Tyr | Pro | Glu | Glu | Met | Glu | Asp | Asp | Asp | Asp | Asp | Ala | Ser | Tyr | Cys | |
| 35 | | | | | 40 | | | | | 45 | | | | | 50 | |

| | | | | | | | | | | | | | | | | |
|---|---|---|---|---|---|---|---|---|---|---|---|---|---|---|---|---|
| acg | gaa | agc | agc | ttc | agg | agc | cat | agt | acc | tac | agc | agc | act | cca | ggt | 669 |
| Thr | Glu | Ser | Ser | Phe | Arg | Ser | His | Ser | Thr | Tyr | Ser | Ser | Thr | Pro | Gly | |
| | | | | 55 | | | | | 60 | | | | | 65 | | |

| | | | | | | | | | | | | | | | | |
|---|---|---|---|---|---|---|---|---|---|---|---|---|---|---|---|---|
| agg | cga | aaa | cca | aga | gta | cat | cgg | cct | cgt | tct | cct | ata | ttg | gaa | gaa | 717 |
| Arg | Arg | Lys | Pro | Arg | Val | His | Arg | Pro | Arg | Ser | Pro | Ile | Leu | Glu | Glu | |
| | | | 70 | | | | | 75 | | | | | 80 | | | |

| | | | | | | | | | | | | | | | | |
|---|---|---|---|---|---|---|---|---|---|---|---|---|---|---|---|---|
| aaa | gac | atc | ccg | ccc | ctt | gaa | ttt | ccc | aag | tcc | tct | gag | gat | tta | atg | 765 |
| Lys | Asp | Ile | Pro | Pro | Leu | Glu | Phe | Pro | Lys | Ser | Ser | Glu | Asp | Leu | Met | |
| | | 85 | | | | | 90 | | | | | 95 | | | | |

| | | | | | | | | | | | | | | | | |
|---|---|---|---|---|---|---|---|---|---|---|---|---|---|---|---|---|
| gtg | cct | aat | gag | cat | ata | atg | aat | gtc | att | gcc | att | tac | gag | gta | ctg | 813 |
| Val | Pro | Asn | Glu | His | Ile | Met | Asn | Val | Ile | Ala | Ile | Tyr | Glu | Val | Leu | |
| | 100 | | | | | 105 | | | | | 110 | | | | | |

| | | | | | | | | | | | | | | | | |
|---|---|---|---|---|---|---|---|---|---|---|---|---|---|---|---|---|
| cgg | aac | ttt | ggc | act | gtt | ttg | aga | tta | tct | cct | ttt | cgc | ttt | gag | gac | 861 |
| Arg | Asn | Phe | Gly | Thr | Val | Leu | Arg | Leu | Ser | Pro | Phe | Arg | Phe | Glu | Asp | |
| 115 | | | | | 120 | | | | | 125 | | | | | 130 | |

| | | | | | | | | | | | | | | | | |
|---|---|---|---|---|---|---|---|---|---|---|---|---|---|---|---|---|
| ttt | tgt | gca | gct | ctg | gtg | agc | caa | gag | cag | tgc | aca | ctc | atg | gca | gag | 909 |
| Phe | Cys | Ala | Ala | Leu | Val | Ser | Gln | Glu | Gln | Cys | Thr | Leu | Met | Ala | Glu | |
| | | | | 135 | | | | | 140 | | | | | 145 | | |

| | | | | | | | | | | | | | | | | |
|---|---|---|---|---|---|---|---|---|---|---|---|---|---|---|---|---|
| atg | cat | gtt | gtg | ctt | ttg | aaa | gca | gtt | ctg | cgt | gaa | gaa | gac | act | tcc | 957 |
| Met | His | Val | Val | Leu | Leu | Lys | Ala | Val | Leu | Arg | Glu | Glu | Asp | Thr | Ser | |
| | | | 150 | | | | | 155 | | | | | 160 | | | |

| | | | | | | | | | | | | | | | | |
|---|---|---|---|---|---|---|---|---|---|---|---|---|---|---|---|---|
| aat | act | acc | ttt | gga | cct | gct | gat | ctg | aaa | gat | agc | gtt | aat | tcc | aca | 1005 |
| Asn | Thr | Thr | Phe | Gly | Pro | Ala | Asp | Leu | Lys | Asp | Ser | Val | Asn | Ser | Thr | |
| | | 165 | | | | | 170 | | | | | 175 | | | | |

| | | | | | | | | | | | | | | | | |
|---|---|---|---|---|---|---|---|---|---|---|---|---|---|---|---|---|
| ctg | tat | ttc | ata | gat | ggg | atg | acg | tgg | cca | gag | gtg | ctg | cgg | gtg | tac | 1053 |
| Leu | Tyr | Phe | Ile | Asp | Gly | Met | Thr | Trp | Pro | Glu | Val | Leu | Arg | Val | Tyr | |
| | 180 | | | | | 185 | | | | | 190 | | | | | |

```
tgt gag agt gat aag gag tac cat cac gtt ctt cct tac caa gag gca   1101
Cys Glu Ser Asp Lys Glu Tyr His His Val Leu Pro Tyr Gln Glu Ala
195                 200                 205                 210 gag gac tac cca tat gga cca gta gag aac aag atc aaa gtt cta cag   1149
Glu Asp Tyr Pro Tyr Gly Pro Val Glu Asn Lys Ile Lys Val Leu Gln
                215                 220                 225 ttt cta gtc gat cag ttt ctt aca aca aat att gct cga gag gaa ttg   1197
Phe Leu Val Asp Gln Phe Leu Thr Thr Asn Ile Ala Arg Glu Glu Leu
            230                 235                 240 atg tct gaa ggg gtg ata cag tat gat gac cat tgt agg gtt tgt cac   1245
Met Ser Glu Gly Val Ile Gln Tyr Asp Asp His Cys Arg Val Cys His
        245                 250                 255 aaa ctt ggg gat ttg ctt tgc tgt gag aca tgt tca gca gta tac cat   1293
Lys Leu Gly Asp Leu Leu Cys Cys Glu Thr Cys Ser Ala Val Tyr His
    260                 265                 270 ttg gaa tgt gtg aag cca cct ctt gag gag gtg cca gag gac gag tgg   1341
Leu Glu Cys Val Lys Pro Pro Leu Glu Glu Val Pro Glu Asp Glu Trp
275                 280                 285                 290 cag tgt gaa gtc tgt gta gca cac aag gtg cct ggt gtg act gac tgt   1389
Gln Cys Glu Val Cys Val Ala His Lys Val Pro Gly Val Thr Asp Cys
                295                 300                 305 gtt gct gaa atc caa aaa aat aaa cca tat att cga cat gaa cct att   1437
Val Ala Glu Ile Gln Lys Asn Lys Pro Tyr Ile Arg His Glu Pro Ile
            310                 315                 320 gga tat gat aga agt cgg agg aaa tac tgg ttc ttg aac cga aga ctc   1485
Gly Tyr Asp Arg Ser Arg Arg Lys Tyr Trp Phe Leu Asn Arg Arg Leu
        325                 330                 335 ata ata gaa gaa gat aca gaa aat gaa aat gaa aag aaa att tgg tat   1533
Ile Ile Glu Glu Asp Thr Glu Asn Glu Asn Glu Lys Lys Ile Trp Tyr
    340                 345                 350 tac agc aca aag gtc caa ctt gca gaa tta att gac tgt cta gac aaa   1581
Tyr Ser Thr Lys Val Gln Leu Ala Glu Leu Ile Asp Cys Leu Asp Lys
355                 360                 365                 370 gat tat tgg gaa gca gaa ctc tgc aaa att cta gaa gaa atg cgt gaa   1629
Asp Tyr Trp Glu Ala Glu Leu Cys Lys Ile Leu Glu Glu Met Arg Glu
                375                 380                 385 gaa atc cac cga cac atg gac ata act gaa gac ctg acc aat aag gct   1677
Glu Ile His Arg His Met Asp Ile Thr Glu Asp Leu Thr Asn Lys Ala
            390                 395                 400 cgg ggc agt aac aaa tcc ttt ctg gcg gca gct aat gaa gaa att ttg   1725
Arg Gly Ser Asn Lys Ser Phe Leu Ala Ala Ala Asn Glu Glu Ile Leu
        405                 410                 415 gag tcc ata aga gcc aaa aag gga gac att gat aat gtt aaa agc cca   1773
Glu Ser Ile Arg Ala Lys Lys Gly Asp Ile Asp Asn Val Lys Ser Pro
    420                 425                 430 gaa gaa aca gaa aaa gac aag aat gag act gag aat gac tct aaa gat   1821
Glu Glu Thr Glu Lys Asp Lys Asn Glu Thr Glu Asn Asp Ser Lys Asp
435                 440                 445                 450 gct gag aaa aac aga gaa gaa ttt gaa gac cag tcc ctt gaa aaa gac   1869
Ala Glu Lys Asn Arg Glu Glu Phe Glu Asp Gln Ser Leu Glu Lys Asp
                455                 460                 465 agt gac gac aaa aca cca gat gat gac cct gag caa gga aaa tct gag   1917
Ser Asp Asp Lys Thr Pro Asp Asp Asp Pro Glu Gln Gly Lys Ser Glu
            470                 475                 480 gta ggt gat ttc aaa tcg gag aag tcc aac ggg gag cta agt gaa tct   1965
Val Gly Asp Phe Lys Ser Glu Lys Ser Asn Gly Glu Leu Ser Glu Ser
        485                 490                 495 cct gga gct gga aaa gga gca tct ggt tca act cga atc atc acc aga   2013
Pro Gly Ala Gly Lys Gly Ala Ser Gly Ser Thr Arg Ile Ile Thr Arg
    500                 505                 510
```

```
ttg cgg aat cca gat agc aaa ctt agt cag ctg aag agc cag cag gtg     2061
Leu Arg Asn Pro Asp Ser Lys Leu Ser Gln Leu Lys Ser Gln Gln Val
515                 520                 525                 530 gca gcc gct gca cat gaa gca aat aaa tta ttt aag gag ggc aaa gag     2109
Ala Ala Ala Ala His Glu Ala Asn Lys Leu Phe Lys Glu Gly Lys Glu
                535                 540                 545 gta ctg gta gtt aac tct caa gga gaa att tca cgg ttg agc acc aaa     2157
Val Leu Val Val Asn Ser Gln Gly Glu Ile Ser Arg Leu Ser Thr Lys
550                 555                 560 aag gaa gtg atc atg aaa gga aat atc aac aat tat ttt aaa ttg ggt     2205
Lys Glu Val Ile Met Lys Gly Asn Ile Asn Asn Tyr Phe Lys Leu Gly
            565                 570                 575 caa gaa ggg aag tat cgc gtc tac cac aat caa tac tcc acc aat tca     2253
Gln Glu Gly Lys Tyr Arg Val Tyr His Asn Gln Tyr Ser Thr Asn Ser
        580                 585                 590 ttt gct ttg aat aag cac cag cac aga gaa gac cat gat aag aga agg     2301
Phe Ala Leu Asn Lys His Gln His Arg Glu Asp His Asp Lys Arg Arg
595                 600                 605                 610 cat ctt gca cat aag ttc tgt ctg act cca gca gga gag ttc aaa tgg     2349
His Leu Ala His Lys Phe Cys Leu Thr Pro Ala Gly Glu Phe Lys Trp
                615                 620                 625 aac ggt tct gtc cat ggg tcc aaa gtt ctt acc ata tct act ctg aga     2397
Asn Gly Ser Val His Gly Ser Lys Val Leu Thr Ile Ser Thr Leu Arg
                630                 635                 640 ctg act atc acc caa tta gaa aac aac atc cct tca tcc ttt ctt cat     2445
Leu Thr Ile Thr Gln Leu Glu Asn Asn Ile Pro Ser Ser Phe Leu His
            645                 650                 655 ccc aac tgg gca tca cat agg gca aat tgg atc aag gca gtt cag atg     2493
Pro Asn Trp Ala Ser His Arg Ala Asn Trp Ile Lys Ala Val Gln Met
        660                 665                 670 tgt agc aaa ccc aga gaa ttt gca ttg gct tta gcc att ttg gag tgt     2541
Cys Ser Lys Pro Arg Glu Phe Ala Leu Ala Leu Ala Ile Leu Glu Cys
675                 680                 685                 690 gca gtt aaa cca gtt gtg atg cta cca ata tgg cga gaa ttt tta gga     2589
Ala Val Lys Pro Val Val Met Leu Pro Ile Trp Arg Glu Phe Leu Gly
                695                 700                 705 cat acc agg tta cac cgg atg aca tca att gaa aga gaa gaa aag gag     2637
His Thr Arg Leu His Arg Met Thr Ser Ile Glu Arg Glu Glu Lys Glu
                710                 715                 720 aaa gtc aaa aaa aaa gag aag aaa cag gaa gaa gaa gaa acg atg cag     2685
Lys Val Lys Lys Lys Glu Lys Lys Gln Glu Glu Glu Glu Thr Met Gln
            725                 730                 735 caa gcg aca tgg gta aaa tac aca ttt cca gtt aag cat cag gtt tgg     2733
Gln Ala Thr Trp Val Lys Tyr Thr Phe Pro Val Lys His Gln Val Trp
        740                 745                 750 aaa caa aaa ggt gaa gag tac aga gtg aca gga tat ggt ggt tgg agc     2781
Lys Gln Lys Gly Glu Glu Tyr Arg Val Thr Gly Tyr Gly Gly Trp Ser
755                 760                 765                 770 tgg att agt aaa act cat gtt tat agg ttt gtt cct aaa ttg cca ggc     2829
Trp Ile Ser Lys Thr His Val Tyr Arg Phe Val Pro Lys Leu Pro Gly
                775                 780                 785 aat act aat gtg aat tac aga aag tcg tta gaa gga acc aaa aat aat     2877
Asn Thr Asn Val Asn Tyr Arg Lys Ser Leu Glu Gly Thr Lys Asn Asn
                790                 795                 800 atg gat gaa aat atg gat gag tca gat aaa aga aaa tgt tca cga agt     2925
Met Asp Glu Asn Met Asp Glu Ser Asp Lys Arg Lys Cys Ser Arg Ser
            805                 810                 815 cca aaa aaa ata aaa ata gag cct gat tct gaa aaa gat gag gta aaa     2973
Pro Lys Lys Ile Lys Ile Glu Pro Asp Ser Glu Lys Asp Glu Val Lys
```

-continued

| | | | | | | | | | | | | | | | |
|---|---|---|---|---|---|---|---|---|---|---|---|---|---|---|---|
| | | 820 | | | | 825 | | | | | 830 | | | | |
| ggt | tca | gat | gct | gca | aaa | gga | gca | gac | caa | aat | gaa | atg | gat | atc | tca | 3021 |
| Gly | Ser | Asp | Ala | Ala | Lys | Gly | Ala | Asp | Gln | Asn | Glu | Met | Asp | Ile | Ser |
| 835 | | | | 840 | | | | | 845 | | | | | 850 | |

| aag | att | act | gag | aag | aag | gac | caa | gat | gtg | aag | gag | ctc | tta | gat | tct | 3069 |
| Lys | Ile | Thr | Glu | Lys | Lys | Asp | Gln | Asp | Val | Lys | Glu | Leu | Leu | Asp | Ser |
| | | | | 855 | | | | | 860 | | | | | 865 | |

| gac | agt | gat | aaa | ccc | tgc | aag | gaa | gaa | cca | atg | gaa | gta | gac | gat | gac | 3117 |
| Asp | Ser | Asp | Lys | Pro | Cys | Lys | Glu | Glu | Pro | Met | Glu | Val | Asp | Asp | Asp |
| | | 870 | | | | | 875 | | | | | 880 | | | |

| atg | aaa | aca | gag | tca | cat | gta | aat | tgt | cag | gag | agt | tct | caa | gta | gat | 3165 |
| Met | Lys | Thr | Glu | Ser | His | Val | Asn | Cys | Gln | Glu | Ser | Ser | Gln | Val | Asp |
| | 885 | | | | | 890 | | | | | 895 | | | | |

| gtg | gtc | aat | gtt | agt | gag | ggt | ttt | cat | cta | agg | act | agt | tac | aaa | aag | 3213 |
| Val | Val | Asn | Val | Ser | Glu | Gly | Phe | His | Leu | Arg | Thr | Ser | Tyr | Lys | Lys |
| 900 | | | | | 905 | | | | | 910 | | | | | |

| aaa | aca | aaa | tca | tcc | aaa | cta | gat | gga | ctt | ctt | gaa | agg | aga | att | aaa | 3261 |
| Lys | Thr | Lys | Ser | Ser | Lys | Leu | Asp | Gly | Leu | Leu | Glu | Arg | Arg | Ile | Lys |
| 915 | | | | 920 | | | | | 925 | | | | | 930 | |

| cag | ttt | aca | ctg | gaa | gaa | aaa | cag | cga | ctc | gaa | aaa | atc | aag | ttg | gag | 3309 |
| Gln | Phe | Thr | Leu | Glu | Glu | Lys | Gln | Arg | Leu | Glu | Lys | Ile | Lys | Leu | Glu |
| | | | | 935 | | | | | 940 | | | | | 945 | |

| ggt | gga | att | aag | ggt | ata | gga | aag | act | tct | aca | aat | tct | tca | aaa | aat | 3357 |
| Gly | Gly | Ile | Lys | Gly | Ile | Gly | Lys | Thr | Ser | Thr | Asn | Ser | Ser | Lys | Asn |
| | | | 950 | | | | | 955 | | | | | 960 | | |

| ctc | tct | gaa | tca | cca | gta | ata | acg | aaa | gca | aaa | gaa | ggg | tgt | cag | agt | 3405 |
| Leu | Ser | Glu | Ser | Pro | Val | Ile | Thr | Lys | Ala | Lys | Glu | Gly | Cys | Gln | Ser |
| | | 965 | | | | | 970 | | | | | 975 | | | |

| gac | tcg | atg | aga | caa | gaa | cag | agc | cca | aat | gca | aat | aat | gat | caa | cct | 3453 |
| Asp | Ser | Met | Arg | Gln | Glu | Gln | Ser | Pro | Asn | Ala | Asn | Asn | Asp | Gln | Pro |
| | 980 | | | | | 985 | | | | | 990 | | | | |

| gag | gac | ttg | att | cag | gga | tgt | tca | caa | agt | gat | tcc | tca | gtt | ctt | | 3498 |
| Glu | Asp | Leu | Ile | Gln | Gly | Cys | Ser | Gln | Ser | Asp | Ser | Ser | Val | Leu | |
| 995 | | | | 1000 | | | | | 1005 | | | | | | |

| aga | atg | agt | gat | cct | agt | cat | acc | aca | aac | aaa | ctt | tat | cca | aaa | | 3543 |
| Arg | Met | Ser | Asp | Pro | Ser | His | Thr | Thr | Asn | Lys | Leu | Tyr | Pro | Lys | |
| 1010 | | | | 1015 | | | | | 1020 | | | | | | |

| gat | cga | gtg | tta | gat | gat | gtc | tcc | att | cgg | agc | cca | gaa | aca | aaa | | 3588 |
| Asp | Arg | Val | Leu | Asp | Asp | Val | Ser | Ile | Arg | Ser | Pro | Glu | Thr | Lys | |
| 1025 | | | | 1030 | | | | | 1035 | | | | | | |

| tgt | ccg | aaa | caa | aat | tcc | att | gaa | aat | gac | ata | gaa | gaa | aaa | gtc | | 3633 |
| Cys | Pro | Lys | Gln | Asn | Ser | Ile | Glu | Asn | Asp | Ile | Glu | Glu | Lys | Val | |
| 1040 | | | | 1045 | | | | | 1050 | | | | | | |

| tct | gac | ctt | gcc | agt | aga | ggc | cag | gaa | ccc | act | aag | agt | aaa | acc | | 3678 |
| Ser | Asp | Leu | Ala | Ser | Arg | Gly | Gln | Glu | Pro | Thr | Lys | Ser | Lys | Thr | |
| 1055 | | | | 1060 | | | | | 1065 | | | | | | |

| aaa | gga | aat | gat | ttt | ttc | atc | gat | gac | tct | aaa | cta | gcc | agt | gca | | 3723 |
| Lys | Gly | Asn | Asp | Phe | Phe | Ile | Asp | Asp | Ser | Lys | Leu | Ala | Ser | Ala | |
| 1070 | | | | 1075 | | | | | 1080 | | | | | | |

| gat | gat | att | ggt | act | ttg | atc | tgt | aag | aac | aaa | aaa | ccg | ctc | ata | | 3768 |
| Asp | Asp | Ile | Gly | Thr | Leu | Ile | Cys | Lys | Asn | Lys | Lys | Pro | Leu | Ile | |
| 1085 | | | | 1090 | | | | | 1095 | | | | | | |

| cag | gag | gaa | agt | gac | acc | att | gtt | tct | tct | tcc | aag | agt | gct | tta | | 3813 |
| Gln | Glu | Glu | Ser | Asp | Thr | Ile | Val | Ser | Ser | Ser | Lys | Ser | Ala | Leu | |
| 1100 | | | | 1105 | | | | | 1110 | | | | | | |

| cat | tca | tca | gtg | cct | aaa | agt | acc | aat | gac | aga | gat | gcc | aca | cct | | 3858 |
| His | Ser | Ser | Val | Pro | Lys | Ser | Thr | Asn | Asp | Arg | Asp | Ala | Thr | Pro | |
| 1115 | | | | 1120 | | | | | 1125 | | | | | | |

| ctg | tca | aga | gca | atg | gac | ttt | gaa | gga | aaa | ctg | gga | tgt | gac | tct | | 3903 |

| | | | | | | | | | | | | |
|---|---|---|---|---|---|---|---|---|---|---|---|---|
| Leu 1130 | Ser | Arg | Ala | Met Asp 1135 | Phe | Glu | Gly | Lys Leu 1140 | Gly | Cys | Asp | Ser |

| | | | | | | | | | | | | |
|---|---|---|---|---|---|---|---|---|---|---|---|---|
| gaa Glu 1145 | tct Ser | aat Asn | agc Ser | act Thr | ttg Leu 1150 | gaa Glu | aat Asn | agt Ser | tct Ser | gat Asp 1155 | acc Thr | gtg Val | tct Ser | att Ile | 3948 |

| | | | | | | | | | | | | |
|---|---|---|---|---|---|---|---|---|---|---|---|---|
| cag Gln 1160 | gat Asp | agc Ser | agt Ser | gaa Glu | gaa Glu 1165 | gat Asp | atg Met | att Ile | gtt Val | cag Gln 1170 | aat Asn | agc Ser | aat Asn | gaa Glu | 3993 |

| | | | | | | | | | | | | |
|---|---|---|---|---|---|---|---|---|---|---|---|---|
| agc Ser 1175 | att Ile | tct Ser | gaa Glu | cag Gln | ttc Phe 1180 | aga Arg | act Thr | cga Arg | gaa Glu | caa Gln 1185 | gat Asp | gtt Val | gaa Glu | gtc Val | 4038 |

| | | | | | | | | | | | | |
|---|---|---|---|---|---|---|---|---|---|---|---|---|
| ttg Leu 1190 | gag Glu | ccg Pro | tta Leu | aag Lys | tgt Cys 1195 | gag Glu | ttg Leu | gtt Val | tct Ser | ggt Gly 1200 | gag Glu | tcc Ser | act Thr | gga Gly | 4083 |

| | | | | | | | | | | | | |
|---|---|---|---|---|---|---|---|---|---|---|---|---|
| aac Asn 1205 | tgt Cys | gag Glu | gac Asp | agg Arg | ctg Leu 1210 | ccg Pro | gtc Val | aag Lys | ggg Gly | act Thr 1215 | gaa Glu | gca Ala | aat Asn | ggt Gly | 4128 |

| | | | | | | | | | | | | |
|---|---|---|---|---|---|---|---|---|---|---|---|---|
| aaa Lys 1220 | aaa Lys | cca Pro | agt Ser | cag Gln | cag Gln 1225 | aag Lys | aaa Lys | tta Leu | gag Glu | gag Glu 1230 | aga Arg | cca Pro | gtt Val | aat Asn | 4173 |

| | | | | | | | | | | | | |
|---|---|---|---|---|---|---|---|---|---|---|---|---|
| aaa Lys 1235 | tgt Cys | agt Ser | gat Asp | caa Gln | ata Ile 1240 | aag Lys | cta Leu | aaa Lys | aat Asn | acc Thr 1245 | act Thr | gac Asp | aaa Lys | aag Lys | 4218 |

| | | | | | | | | | | | | |
|---|---|---|---|---|---|---|---|---|---|---|---|---|
| aat Asn 1250 | aat Asn | gaa Glu | aat Asn | cga Arg | gag Glu 1255 | tct Ser | gaa Glu | aag Lys | aaa Lys | gga Gly 1260 | cag Gln | aga Arg | aca Thr | agt Ser | 4263 |

| | | | | | | | | | | | | |
|---|---|---|---|---|---|---|---|---|---|---|---|---|
| aca Thr 1265 | ttt Phe | caa Gln | ata Ile | aat Asn | gga Gly 1270 | aaa Lys | gat Asp | aat Asn | aaa Lys | ccc Pro 1275 | aaa Lys | ata Ile | tat Tyr | ttg Leu | 4308 |

| | | | | | | | | | | | | |
|---|---|---|---|---|---|---|---|---|---|---|---|---|
| aaa Lys 1280 | ggt Gly | gaa Glu | tgc Cys | ttg Leu | aaa Lys 1285 | gaa Glu | att Ile | tct Ser | gag Glu | agt Ser 1290 | aga Arg | gta Val | gta Val | agt Ser | 4353 |

| | | | | | | | | | | | | |
|---|---|---|---|---|---|---|---|---|---|---|---|---|
| ggt Gly 1295 | aat Asn | gtt Val | gaa Glu | cca Pro | aag Lys 1300 | gtt Val | aat Asn | aat Asn | ata Ile | aat Asn 1305 | aaa Lys | ata Ile | atc Ile | cct Pro | 4398 |

| | | | | | | | | | | | | |
|---|---|---|---|---|---|---|---|---|---|---|---|---|
| gag Glu 1310 | aat Asn | gat Asp | att Ile | aaa Lys | tca Ser 1315 | ttg Leu | act Thr | gtt Val | aaa Lys | gaa Glu 1320 | tct Ser | gct Ala | ata Ile | agg Arg | 4443 |

| | | | | | | | | | | | | |
|---|---|---|---|---|---|---|---|---|---|---|---|---|
| cca Pro 1325 | ttc Phe | att Ile | aat Asn | ggt Gly | gat Asp 1330 | gtc Val | atc Ile | atg Met | gaa Glu | gat Asp 1335 | ttt Phe | aat Asn | gaa Glu | aga Arg | 4488 |

| | | | | | | | | | | | | |
|---|---|---|---|---|---|---|---|---|---|---|---|---|
| aac Asn 1340 | agc Ser | tcc Ser | gaa Glu | aca Thr | aaa Lys 1345 | tcg Ser | cat His | ttg Leu | ctg Leu | agt Ser 1350 | tct Ser | tca Ser | gat Asp | gct Ala | 4533 |

| | | | | | | | | | | | | |
|---|---|---|---|---|---|---|---|---|---|---|---|---|
| gaa Glu 1355 | ggt Gly | aac Asn | tac Tyr | cga Arg | gat Asp 1360 | agc Ser | ctt Leu | gag Glu | acc Thr | ctg Leu 1365 | cca Pro | tca Ser | acc Thr | aaa Lys | 4578 |

| | | | | | | | | | | | | |
|---|---|---|---|---|---|---|---|---|---|---|---|---|
| gag Glu 1370 | tct Ser | gac Asp | agt Ser | aca Thr | cag Gln 1375 | acg Thr | acc Thr | aca Thr | ccc Pro | tca Ser 1380 | gca Ala | tct Ser | tgt Cys | cca Pro | 4623 |

| | | | | | | | | | | | | |
|---|---|---|---|---|---|---|---|---|---|---|---|---|
| gaa Glu 1385 | agc Ser | aat Asn | tca Ser | gtt Val | aat Asn 1390 | cag Gln | gta Val | gaa Glu | gat Asp | atg Met 1395 | gaa Glu | ata Ile | gaa Glu | acc Thr | 4668 |

| | | | | | | | | | | | | |
|---|---|---|---|---|---|---|---|---|---|---|---|---|
| tca Ser 1400 | gaa Glu | gtt Val | aag Lys | aaa Lys | gtt Val 1405 | act Thr | tca Ser | tca Ser | cct Pro | att Ile 1410 | act Thr | tct Ser | gaa Glu | gag Glu | 4713 |

| | | | | | | | | | | | | |
|---|---|---|---|---|---|---|---|---|---|---|---|---|
| gaa Glu 1415 | tct Ser | aat Asn | ctc Leu | agt Ser | aat Asn 1420 | gac Asp | ttt Phe | att Ile | gat Asp | gaa Glu 1425 | aat Asn | ggt Gly | ctg Leu | ccc Pro | 4758 |

| | | | | | | | | | | | | |
|---|---|---|---|---|---|---|---|---|---|---|---|---|
| atc | aac | aaa | aat | gaa | aat | gtc | aat | gga | gaa | tct | aaa | aga | aaa | acc | 4803 |
| Ile | Asn | Lys | Asn | Glu | Asn | Val | Asn | Gly | Glu | Ser | Lys | Arg | Lys | Thr | |
| 1430 | | | | 1435 | | | | | 1440 | | | | | | |

| gtc | atc | aca | gaa | gtc | acc | acg | atg | acc | tcc | aca | gtg | gcc | aca | gaa | 4848 |
| Val | Ile | Thr | Glu | Val | Thr | Thr | Met | Thr | Ser | Thr | Val | Ala | Thr | Glu | |
| 1445 | | | | 1450 | | | | | 1455 | | | | | | |

| tca | aaa | act | gtg | atc | aag | gta | gaa | aaa | ggc | gat | aag | caa | act | gtg | 4893 |
| Ser | Lys | Thr | Val | Ile | Lys | Val | Glu | Lys | Gly | Asp | Lys | Gln | Thr | Val | |
| 1460 | | | | 1465 | | | | | 1470 | | | | | | |

| gtt | tct | tcc | aca | gaa | aat | tgt | gca | aaa | tcc | act | gtc | aca | acc | acc | 4938 |
| Val | Ser | Ser | Thr | Glu | Asn | Cys | Ala | Lys | Ser | Thr | Val | Thr | Thr | Thr | |
| 1475 | | | | 1480 | | | | | 1485 | | | | | | |

| act | aca | aca | gtg | acc | aag | ctt | tcc | aca | ccc | tcc | aca | ggc | ggc | agt | 4983 |
| Thr | Thr | Thr | Val | Thr | Lys | Leu | Ser | Thr | Pro | Ser | Thr | Gly | Gly | Ser | |
| 1490 | | | | 1495 | | | | | 1500 | | | | | | |

| gtg | gac | atc | atc | tct | gta | aag | gag | cag | agc | aaa | acc | gtg | gtc | acc | 5028 |
| Val | Asp | Ile | Ile | Ser | Val | Lys | Glu | Gln | Ser | Lys | Thr | Val | Val | Thr | |
| 1505 | | | | 1510 | | | | | 1515 | | | | | | |

| acg | aca | gtg | aca | gac | tcc | ctg | acc | acc | acg | gga | ggc | aca | ctg | gtt | 5073 |
| Thr | Thr | Val | Thr | Asp | Ser | Leu | Thr | Thr | Thr | Gly | Gly | Thr | Leu | Val | |
| 1520 | | | | 1525 | | | | | 1530 | | | | | | |

| aca | tct | atg | act | gtg | agc | aaa | gag | tat | tcc | aca | cga | gac | aaa | gtg | 5118 |
| Thr | Ser | Met | Thr | Val | Ser | Lys | Glu | Tyr | Ser | Thr | Arg | Asp | Lys | Val | |
| 1535 | | | | 1540 | | | | | 1545 | | | | | | |

| aaa | ctg | atg | aaa | ttt | tca | aga | cca | aag | aag | act | cgt | tca | ggt | aca | 5163 |
| Lys | Leu | Met | Lys | Phe | Ser | Arg | Pro | Lys | Lys | Thr | Arg | Ser | Gly | Thr | |
| 1550 | | | | 1555 | | | | | 1560 | | | | | | |

| gct | ctg | cca | tcc | tat | aga | aaa | ttt | gtt | acc | aag | agc | acc | aag | aag | 5208 |
| Ala | Leu | Pro | Ser | Tyr | Arg | Lys | Phe | Val | Thr | Lys | Ser | Thr | Lys | Lys | |
| 1565 | | | | 1570 | | | | | 1575 | | | | | | |

| agc | att | ttt | gtt | ttg | cct | aat | gat | gac | tta | aaa | aag | ttg | gcc | cga | 5253 |
| Ser | Ile | Phe | Val | Leu | Pro | Asn | Asp | Asp | Leu | Lys | Lys | Leu | Ala | Arg | |
| 1580 | | | | 1585 | | | | | 1590 | | | | | | |

| aaa | gga | gga | atc | cga | gag | gtc | cct | tat | ttt | aat | tac | aat | gca | aaa | 5298 |
| Lys | Gly | Gly | Ile | Arg | Glu | Val | Pro | Tyr | Phe | Asn | Tyr | Asn | Ala | Lys | |
| 1595 | | | | 1600 | | | | | 1605 | | | | | | |

| cct | gct | ttg | gat | ata | tgg | cca | tat | cct | tct | cct | aga | ccg | acc | ttt | 5343 |
| Pro | Ala | Leu | Asp | Ile | Trp | Pro | Tyr | Pro | Ser | Pro | Arg | Pro | Thr | Phe | |
| 1610 | | | | 1615 | | | | | 1620 | | | | | | |

| ggc | atc | act | tgg | agg | tat | aga | ctt | cag | aca | gta | aag | tcc | tta | gct | 5388 |
| Gly | Ile | Thr | Trp | Arg | Tyr | Arg | Leu | Gln | Thr | Val | Lys | Ser | Leu | Ala | |
| 1625 | | | | 1630 | | | | | 1635 | | | | | | |

| gga | gtg | agc | ctg | atg | tta | cgg | tta | ctg | tgg | gca | agt | ttg | aga | tgg | 5433 |
| Gly | Val | Ser | Leu | Met | Leu | Arg | Leu | Leu | Trp | Ala | Ser | Leu | Arg | Trp | |
| 1640 | | | | 1645 | | | | | 1650 | | | | | | |

| gat | gat | atg | gcg | gcc | aag | gtt | cct | cca | gga | gga | ggg | agt | aca | cgg | 5478 |
| Asp | Asp | Met | Ala | Ala | Lys | Val | Pro | Pro | Gly | Gly | Gly | Ser | Thr | Arg | |
| 1655 | | | | 1660 | | | | | 1665 | | | | | | |

| aca | gaa | aca | tcc | gaa | act | gaa | atc | aca | aca | aca | gaa | ata | att | aag | 5523 |
| Thr | Glu | Thr | Ser | Glu | Thr | Glu | Ile | Thr | Thr | Thr | Glu | Ile | Ile | Lys | |
| 1670 | | | | 1675 | | | | | 1680 | | | | | | |

| agg | aga | gat | gtt | ggt | cct | tat | ggc | att | cga | ttt | gaa | tat | tgt | atc | 5568 |
| Arg | Arg | Asp | Val | Gly | Pro | Tyr | Gly | Ile | Arg | Phe | Glu | Tyr | Cys | Ile | |
| 1685 | | | | 1690 | | | | | 1695 | | | | | | |

| agg | aaa | atc | att | tgt | ccc | att | gga | gtt | cca | gaa | aca | cca | aaa | gaa | 5613 |
| Arg | Lys | Ile | Ile | Cys | Pro | Ile | Gly | Val | Pro | Glu | Thr | Pro | Lys | Glu | |
| 1700 | | | | 1705 | | | | | 1710 | | | | | | |

| acg | cct | aca | cct | cag | agg | aaa | ggc | ctt | cga | tca | agt | gca | ctg | cgg | 5658 |
| Thr | Pro | Thr | Pro | Gln | Arg | Lys | Gly | Leu | Arg | Ser | Ser | Ala | Leu | Arg | |
| 1715 | | | | 1720 | | | | | 1725 | | | | | | |

```
cca aag aga cca gaa acg ccc aag caa act ggc cct gtt att att         5703
Pro Lys Arg Pro Glu Thr Pro Lys Gln Thr Gly Pro Val Ile Ile
1730                1735                1740 gaa acc tgg gta gca gaa gaa gaa ctg gaa ttg tgg gag atc agg         5748
Glu Thr Trp Val Ala Glu Glu Glu Leu Glu Leu Trp Glu Ile Arg
1745                1750                1755 gca ttt gct gag aga gtg gag aaa gaa aag gca caa gca gtt gag         5793
Ala Phe Ala Glu Arg Val Glu Lys Glu Lys Ala Gln Ala Val Glu
    1760                1765                1770 caa cag gct aag aaa cga ctg gag cag cag aag ccg aca gtg att         5838
Gln Gln Ala Lys Lys Arg Leu Glu Gln Gln Lys Pro Thr Val Ile
1775                1780                1785 gca act tcc act act tcc cca aca agc agt aca acc agc acc atc         5883
Ala Thr Ser Thr Thr Ser Pro Thr Ser Ser Thr Thr Ser Thr Ile
1790                1795                1800 tct cca gca cag aaa gtt atg gtg gcc ccc ata agt ggc tca gtt         5928
Ser Pro Ala Gln Lys Val Met Val Ala Pro Ile Ser Gly Ser Val
1805                1810                1815 aca act gga acc aaa atg gta cta act act aaa gtt gga tct cca         5973
Thr Thr Gly Thr Lys Met Val Leu Thr Thr Lys Val Gly Ser Pro
1820                1825                1830 gct aca gta aca ttc caa caa aac aag aac ttt cat caa acc ttt         6018
Ala Thr Val Thr Phe Gln Gln Asn Lys Asn Phe His Gln Thr Phe
1835                1840                1845 gct aca tgg gtt aag caa ggc cag tca aat tca ggc gtt gtt caa         6063
Ala Thr Trp Val Lys Gln Gly Gln Ser Asn Ser Gly Val Val Gln
1850                1855                1860 gta cag cag aaa gtc ctg ggt atc att cca tca agt aca ggt acc         6108
Val Gln Gln Lys Val Leu Gly Ile Ile Pro Ser Ser Thr Gly Thr
1865                1870                1875 agt cag caa acc ttt act tca ttc cag ccc agg aca gca aca gtc         6153
Ser Gln Gln Thr Phe Thr Ser Phe Gln Pro Arg Thr Ala Thr Val
1880                1885                1890 aca att agg ccc aat acc tca ggc tct gga gga acc aca agc aat         6198
Thr Ile Arg Pro Asn Thr Ser Gly Ser Gly Gly Thr Thr Ser Asn
1895                1900                1905 tca caa gta atc aca ggg cct cag att cgc cct ggt atg acc gtg         6243
Ser Gln Val Ile Thr Gly Pro Gln Ile Arg Pro Gly Met Thr Val
1910                1915                1920 att aga aca cca ctc caa cag tca aca cta gga aag gca att att         6288
Ile Arg Thr Pro Leu Gln Gln Ser Thr Leu Gly Lys Ala Ile Ile
1925                1930                1935 cga aca cct gtg atg gta cag cca ggt gct cct cag caa gtg atg         6333
Arg Thr Pro Val Met Val Gln Pro Gly Ala Pro Gln Gln Val Met
1940                1945                1950 act caa atc atc agg ggg cag cct gtc tcc act gca gtc tcc gcc         6378
Thr Gln Ile Ile Arg Gly Gln Pro Val Ser Thr Ala Val Ser Ala
1955                1960                1965 cct aac acg gtt tcc tca aca cct ggg cag aaa agc tta act tca         6423
Pro Asn Thr Val Ser Ser Thr Pro Gly Gln Lys Ser Leu Thr Ser
1970                1975                1980 gca acg tcc act tca aat ata cag tct tca gcc tca caa ccc cct         6468
Ala Thr Ser Thr Ser Asn Ile Gln Ser Ser Ala Ser Gln Pro Pro
1985                1990                1995 cgc ccc caa caa gga caa gtg aag ctc acc atg gct caa ctt act         6513
Arg Pro Gln Gln Gly Gln Val Lys Leu Thr Met Ala Gln Leu Thr
2000                2005                2010 cag tta aca cag ggc cac ggt ggc aat caa ggt ttg aca gta gta         6558
Gln Leu Thr Gln Gly His Gly Gly Asn Gln Gly Leu Thr Val Val
```

```
             2015                2020                2025 att caa gga caa ggt caa act act gga cag ttg cag ttg ata cct      6603
Ile Gln Gly Gln Gly Gln Thr Thr Gly Gln Leu Gln Leu Ile Pro
2030                2035                2040 caa ggg gtg act gta ctc cca ggc cca ggc cag cag cta atg caa      6648
Gln Gly Val Thr Val Leu Pro Gly Pro Gly Gln Gln Leu Met Gln
2045                2050                2055 gct gca atg cca aat ggt act gtt cag cga ttc ctc ttt acc cca      6693
Ala Ala Met Pro Asn Gly Thr Val Gln Arg Phe Leu Phe Thr Pro
2060                2065                2070 ttg gca aca aca gcc acc aca gcc agc acc acc acc acc act gtt      6738
Leu Ala Thr Thr Ala Thr Thr Ala Ser Thr Thr Thr Thr Thr Val
2075                2080                2085 tcc acg aca gca gca ggt aca ggt gaa caa agg cag agt aaa ctg      6783
Ser Thr Thr Ala Ala Gly Thr Gly Glu Gln Arg Gln Ser Lys Leu
2090                2095                2100 tca ccc cag atg cag gta cat caa gac aaa acc ctg cca cca gct      6828
Ser Pro Gln Met Gln Val His Gln Asp Lys Thr Leu Pro Pro Ala
2105                2110                2115 cag tca tca agt gtg ggt cca gca aaa gcc cag cca cag act gct      6873
Gln Ser Ser Ser Val Gly Pro Ala Lys Ala Gln Pro Gln Thr Ala
2120                2125                2130 cag cct tca gct cgg ccc cag ccc caa acc cag ccc cag tcc cca      6918
Gln Pro Ser Ala Arg Pro Gln Pro Gln Thr Gln Pro Gln Ser Pro
2135                2140                2145 gct cag cct gaa gtt cag act cag cct gaa gtt cag acc caa aca      6963
Ala Gln Pro Glu Val Gln Thr Gln Pro Glu Val Gln Thr Gln Thr
2150                2155                2160 act gtt tca tcc cat gtc cct tct gaa gca caa ccc acc cac gca      7008
Thr Val Ser Ser His Val Pro Ser Glu Ala Gln Pro Thr His Ala
2165                2170                2175 cag tca tcc aag ccc caa gtt gca gca cag tct cag cct caa agt      7053
Gln Ser Ser Lys Pro Gln Val Ala Ala Gln Ser Gln Pro Gln Ser
2180                2185                2190 aat gtc caa gga cag tct cct gtt cgt gtc caa agt cca tca cag      7098
Asn Val Gln Gly Gln Ser Pro Val Arg Val Gln Ser Pro Ser Gln
2195                2200                2205 act cga ata cgt cca tca act cca tcc caa ctg tct cct gga caa      7143
Thr Arg Ile Arg Pro Ser Thr Pro Ser Gln Leu Ser Pro Gly Gln
2210                2215                2220 caa tcc cag gtt cag act aca acc tca caa ccg att cca att caa      7188
Gln Ser Gln Val Gln Thr Thr Thr Ser Gln Pro Ile Pro Ile Gln
2225                2230                2235 cca cat aca tct ctt cag ata cct tcc caa ggc cag cca cag tca      7233
Pro His Thr Ser Leu Gln Ile Pro Ser Gln Gly Gln Pro Gln Ser
2240                2245                2250 caa ccc cag gta cag tct tca act caa act ctt tca tca gga caa      7278
Gln Pro Gln Val Gln Ser Ser Thr Gln Thr Leu Ser Ser Gly Gln
2255                2260                2265 act tta aat caa gtt agt gtt tca tcc cca tcc cgt cct cag cta      7323
Thr Leu Asn Gln Val Ser Val Ser Ser Pro Ser Arg Pro Gln Leu
2270                2275                2280 caa ata cag cag cca cag ccc caa gtc att gct gtg cct cag ctg      7368
Gln Ile Gln Gln Pro Gln Pro Gln Val Ile Ala Val Pro Gln Leu
2285                2290                2295 caa caa caa gtc cag gtt ctc tct cag atc cag tca cag gtt gtg      7413
Gln Gln Gln Val Gln Val Leu Ser Gln Ile Gln Ser Gln Val Val
2300                2305                2310 gct cag ata cag gct cag caa agt ggt gtg ccc cag caa atc aaa      7458
```

```
Ala Gln Ile Gln Ala Gln Gln Ser Gly Val Pro Gln Gln Ile Lys
2315              2320                  2325 ctc cag tta cct atc caa att cag caa agc agt gct gtg cag act    7503
Leu Gln Leu Pro Ile Gln Ile Gln Gln Ser Ser Ala Val Gln Thr
2330              2335                  2340 cac cag att cag aat gtg gtt aca gtg cag gca gcc agt gtg caa    7548
His Gln Ile Gln Asn Val Val Thr Val Gln Ala Ala Ser Val Gln
2345              2350                  2355 gag cag ttg caa agg gtt cag caa ctc agg gat cag cag caa aag    7593
Glu Gln Leu Gln Arg Val Gln Gln Leu Arg Asp Gln Gln Gln Lys
2360              2365                  2370 aag aaa cag caa cag ata gaa att aag cgt gaa cac acc ctc caa    7638
Lys Lys Gln Gln Gln Ile Glu Ile Lys Arg Glu His Thr Leu Gln
2375              2380                  2385 gct tct aat caa agt gaa atc att cag aaa cag gtg gtg atg aag    7683
Ala Ser Asn Gln Ser Glu Ile Ile Gln Lys Gln Val Val Met Lys
2390              2395                  2400 cat aat gct gta ata gaa cat tta aaa cag aaa aag agc atg act    7728
His Asn Ala Val Ile Glu His Leu Lys Gln Lys Lys Ser Met Thr
2405              2410                  2415 cca gct gaa aga gaa gag aat caa aga atg att gtc tgt aac cag    7773
Pro Ala Glu Arg Glu Glu Asn Gln Arg Met Ile Val Cys Asn Gln
2420              2425                  2430 gtg atg aag tat att ttg gat aag ata gat aaa gaa gaa aaa cag    7818
Val Met Lys Tyr Ile Leu Asp Lys Ile Asp Lys Glu Glu Lys Gln
2435              2440                  2445 gca gca aaa aaa cgg aag cgt gaa gag agt gtg gag cag aaa cgt    7863
Ala Ala Lys Lys Arg Lys Arg Glu Glu Ser Val Glu Gln Lys Arg
2450              2455                  2460 agc aag cag aat gcc act aag ctg tca gct ctg ctc ttc aag cac    7908
Ser Lys Gln Asn Ala Thr Lys Leu Ser Ala Leu Leu Phe Lys His
2465              2470                  2475 aaa gag cag ctc aga gcc gag atc ctg aag aag aga gca ctc ctg    7953
Lys Glu Gln Leu Arg Ala Glu Ile Leu Lys Lys Arg Ala Leu Leu
2480              2485                  2490 gac aag gat ctg caa att gaa gtg cag gaa gag ctg aag aga gac    7998
Asp Lys Asp Leu Gln Ile Glu Val Gln Glu Glu Leu Lys Arg Asp
2495              2500                  2505 ctg aaa att aag aaa gaa aaa gac ctg atg cag ttg gct cag gcc    8043
Leu Lys Ile Lys Lys Glu Lys Asp Leu Met Gln Leu Ala Gln Ala
2510              2515                  2520 aca gca gta gct gca ccc tgc ccc cca gtg aca cca gtt ctt cca    8088
Thr Ala Val Ala Ala Pro Cys Pro Pro Val Thr Pro Val Leu Pro
2525              2530                  2535 gcc cct cca gcc cct cca cct tca cct ccc cca cct ggt gtg        8133
Ala Pro Pro Ala Pro Pro Pro Ser Pro Pro Pro Pro Gly Val
2540              2545                  2550 caa cac aca ggc ctt ctg tcc acg ccc acc tta cct gtt gct tcc    8178
Gln His Thr Gly Leu Leu Ser Thr Pro Thr Leu Pro Val Ala Ser
2555              2560                  2565 cag aag agg aag cgg gaa gag gaa aaa gac tcc agc tca aag tcc    8223
Gln Lys Arg Lys Arg Glu Glu Glu Lys Asp Ser Ser Ser Lys Ser
2570              2575                  2580 aag aaa aag aaa atg atc tct act acc tca aag gaa act aag aag    8268
Lys Lys Lys Lys Met Ile Ser Thr Thr Ser Lys Glu Thr Lys Lys
2585              2590                  2595 gac aca aag ctt tac tgt atc tgt aaa acg cct tat gat gaa tct    8313
Asp Thr Lys Leu Tyr Cys Ile Cys Lys Thr Pro Tyr Asp Glu Ser
2600              2605                  2610
```

| | |
|---|---|
| aaa ttt tat att ggc tgt gat cgg tgt cag aat tgg tac cat ggg<br>Lys Phe Tyr Ile Gly Cys Asp Arg Cys Gln Asn Trp Tyr His Gly<br>2615                    2620                  2625 | 8358 |
| cgc tgc gtt ggc atc ttg caa agt gag gca gag ctc att gat gag<br>Arg Cys Val Gly Ile Leu Gln Ser Glu Ala Glu Leu Ile Asp Glu<br>2630                    2635                  2640 | 8403 |
| tat gtc tgt cca cag tgc cag tca aca gag gat gcc atg aca gtg<br>Tyr Val Cys Pro Gln Cys Gln Ser Thr Glu Asp Ala Met Thr Val<br>2645                    2650                  2655 | 8448 |
| ctc acg cca cta aca gag aag gat tat gag ggg ttg aag agg gtg<br>Leu Thr Pro Leu Thr Glu Lys Asp Tyr Glu Gly Leu Lys Arg Val<br>2660                    2665                  2670 | 8493 |
| ctc cgt tcc tta cag gcc cat aag atg gcc tgg cct ttc ctt gaa<br>Leu Arg Ser Leu Gln Ala His Lys Met Ala Trp Pro Phe Leu Glu<br>2675                    2680                  2685 | 8538 |
| cca gta gac cct aat gat gca cca gat tat tat ggt gtt att aag<br>Pro Val Asp Pro Asn Asp Ala Pro Asp Tyr Tyr Gly Val Ile Lys<br>2690                    2695                  2700 | 8583 |
| gaa cct atg gac ctt gcc acc atg gaa gaa aga gta caa aga cga<br>Glu Pro Met Asp Leu Ala Thr Met Glu Glu Arg Val Gln Arg Arg<br>2705                    2710                  2715 | 8628 |
| tat tat gaa aag ctg acg gaa ttt gtg gca gat atg acc aaa att<br>Tyr Tyr Glu Lys Leu Thr Glu Phe Val Ala Asp Met Thr Lys Ile<br>2720                    2725                  2730 | 8673 |
| ttt gat aac tgt cgt tac tac aat cca agt gac tcc cca ttt tac<br>Phe Asp Asn Cys Arg Tyr Tyr Asn Pro Ser Asp Ser Pro Phe Tyr<br>2735                    2740                  2745 | 8718 |
| cag tgt gca gaa gtt ctc gaa tca ttc ttt gta cag aaa ttg aaa<br>Gln Cys Ala Glu Val Leu Glu Ser Phe Phe Val Gln Lys Leu Lys<br>2750                    2755                  2760 | 8763 |
| ggc ttc aaa gct agc agg tct cat aac aac aaa ctg cag tct aca<br>Gly Phe Lys Ala Ser Arg Ser His Asn Asn Lys Leu Gln Ser Thr<br>2765                    2770                  2775 | 8808 |
| gct tct taa agttcagcgt gttaacctaa cataaaacac agcaagaatc<br>Ala Ser<br>2780 | 8857 |
| tggttgtctg aactatttta aattaaggag ccagatgttt ttagtcaggc tatcctgaca | 8917 |
| agacttgacc taaacttcgt ttttattggt cataacagtc caattatatt cttggccaat | 8977 |
| tttgtccaac ggacaagaaa aaagcaaagt caacgacacc attatcttgt caagatcaga | 9037 |
| tggttttact attgtggcag aagcgagaaa actttgttta ttgaaaaaaa agaaaaaga | 9097 |
| aagcaagaaa aaaagatact atggggtcaa gtgtaactcc atggaaatgc acgtctgct | 9157 |
| cttcagtgaa gaagctggtt tagagtctca cagaaaactt ttgactgtat ttatttattg | 9217 |
| ttgcaaaaaa gacgcttttt tattgctgcc ctcatttgtc agctaagtat tttttcttat | 9277 |
| aaaatccagc cccggttaca tataatcatc tgtatcttat catgattcct gtaggtaaaa | 9337 |
| gtacaagacg acctctagat gtcttttctt tctatgaaag gagctgctat gtacacatgt | 9397 |
| gcacacacac acaactggga atcaacaatg agtttattgt tcatggtaga ttaaaattaa | 9457 |
| gcttgcataa aggttgggct aagtggtcct tgggctacag actctgttgc cttgaatata | 9517 |
| acagtacaat ttgtcaatta ctctgcacca ggctaaagtg agtaaaatct atttgaaggt | 9577 |
| atcttgtttg taaacatttg tcagattcta attttttttct tttgtattaa aattcaacta | 9637 |
| tggatgtata tgaaacaaaa taaatggaga taatttttct cccacaaaaa aaaaaaaaa | 9697 |
| aaa | 9700 |

```
<210> SEQ ID NO 2
<211> LENGTH: 2781
<212> TYPE: PRT
<213> ORGANISM: Homo sapiens

<400> SEQUENCE: 2

Met Val Ser Glu Glu Glu Glu Asp Gly Asp Ala Glu Thr
1               5                   10                  15

Gln Asp Ser Glu Asp Asp Glu Asp Glu Met Glu Glu Asp Asp Asp
                20                  25                  30

Asp Ser Asp Tyr Pro Glu Glu Met Glu Asp Asp Asp Ala Ser
            35                  40                  45

Tyr Cys Thr Glu Ser Ser Phe Arg Ser His Ser Thr Tyr Ser Ser Thr
50                          55                          60

Pro Gly Arg Arg Lys Pro Arg Val His Arg Pro Arg Ser Pro Ile Leu
65                  70                      75                  80

Glu Glu Lys Asp Ile Pro Pro Leu Glu Phe Pro Lys Ser Ser Glu Asp
                    85                  90                  95

Leu Met Val Pro Asn Glu His Ile Met Asn Val Ile Ala Ile Tyr Glu
                100                 105                 110

Val Leu Arg Asn Phe Gly Thr Val Leu Arg Leu Ser Pro Phe Arg Phe
                115                 120                 125

Glu Asp Phe Cys Ala Ala Leu Val Ser Gln Glu Gln Cys Thr Leu Met
130                 135                 140

Ala Glu Met His Val Val Leu Leu Lys Ala Val Leu Arg Glu Glu Asp
145                 150                 155                 160

Thr Ser Asn Thr Thr Phe Gly Pro Ala Asp Leu Lys Asp Ser Val Asn
                165                 170                 175

Ser Thr Leu Tyr Phe Ile Asp Gly Met Thr Trp Pro Glu Val Leu Arg
                180                 185                 190

Val Tyr Cys Glu Ser Asp Lys Glu Tyr His His Val Leu Pro Tyr Gln
                195                 200                 205

Glu Ala Glu Asp Tyr Pro Tyr Gly Pro Val Glu Asn Lys Ile Lys Val
210                 215                 220

Leu Gln Phe Leu Val Asp Gln Phe Leu Thr Thr Asn Ile Ala Arg Glu
225                 230                 235                 240

Glu Leu Met Ser Glu Gly Val Ile Gln Tyr Asp Asp His Cys Arg Val
                245                 250                 255

Cys His Lys Leu Gly Asp Leu Leu Cys Cys Glu Thr Cys Ser Ala Val
                260                 265                 270

Tyr His Leu Glu Cys Val Lys Pro Pro Leu Glu Glu Val Pro Glu Asp
            275                 280                 285

Glu Trp Gln Cys Glu Val Cys Val Ala His Lys Val Pro Gly Val Thr
290                 295                 300

Asp Cys Val Ala Glu Ile Gln Lys Asn Lys Pro Tyr Ile Arg His Glu
305                 310                 315                 320

Pro Ile Gly Tyr Asp Arg Ser Arg Arg Lys Tyr Trp Phe Leu Asn Arg
                325                 330                 335

Arg Leu Ile Ile Glu Glu Asp Thr Glu Asn Glu Asn Glu Lys Lys Ile
                340                 345                 350

Trp Tyr Tyr Ser Thr Lys Val Gln Leu Ala Glu Leu Ile Asp Cys Leu
            355                 360                 365

Asp Lys Asp Tyr Trp Glu Ala Glu Leu Cys Lys Ile Leu Glu Glu Met
370                 375                 380
```

-continued

```
Arg Glu Glu Ile His Arg His Met Asp Ile Thr Glu Asp Leu Thr Asn
385                 390                 395                 400

Lys Ala Arg Gly Ser Asn Lys Ser Phe Leu Ala Ala Asn Glu Glu
            405                 410                 415

Ile Leu Glu Ser Ile Arg Ala Lys Lys Gly Asp Ile Asp Asn Val Lys
            420                 425                 430

Ser Pro Glu Glu Thr Glu Lys Asp Lys Asn Glu Thr Glu Asn Asp Ser
        435                 440                 445

Lys Asp Ala Glu Lys Asn Arg Glu Glu Phe Glu Asp Gln Ser Leu Glu
    450                 455                 460

Lys Asp Ser Asp Asp Lys Thr Pro Asp Asp Pro Glu Gln Gly Lys
465                 470                 475                 480

Ser Glu Val Gly Asp Phe Lys Ser Glu Lys Ser Asn Gly Glu Leu Ser
            485                 490                 495

Glu Ser Pro Gly Ala Gly Lys Gly Ala Ser Gly Ser Thr Arg Ile Ile
        500                 505                 510

Thr Arg Leu Arg Asn Pro Asp Ser Lys Leu Ser Gln Leu Lys Ser Gln
    515                 520                 525

Gln Val Ala Ala Ala His Glu Ala Asn Lys Leu Phe Lys Glu Gly
530                 535                 540

Lys Glu Val Leu Val Val Asn Ser Gln Gly Glu Ile Ser Arg Leu Ser
545                 550                 555                 560

Thr Lys Lys Glu Val Ile Met Lys Gly Asn Ile Asn Asn Tyr Phe Lys
            565                 570                 575

Leu Gly Gln Glu Gly Lys Tyr Arg Val Tyr His Asn Gln Tyr Ser Thr
        580                 585                 590

Asn Ser Phe Ala Leu Asn Lys His Gln His Arg Glu Asp His Asp Lys
    595                 600                 605

Arg Arg His Leu Ala His Lys Phe Cys Leu Thr Pro Ala Gly Glu Phe
610                 615                 620

Lys Trp Asn Gly Ser Val His Gly Ser Lys Val Leu Thr Ile Ser Thr
625                 630                 635                 640

Leu Arg Leu Thr Ile Thr Gln Leu Glu Asn Asn Ile Pro Ser Ser Phe
            645                 650                 655

Leu His Pro Asn Trp Ala Ser His Arg Ala Asn Trp Ile Lys Ala Val
        660                 665                 670

Gln Met Cys Ser Lys Pro Arg Glu Phe Ala Leu Ala Leu Ala Ile Leu
    675                 680                 685

Glu Cys Ala Val Lys Pro Val Val Met Leu Pro Ile Trp Arg Glu Phe
690                 695                 700

Leu Gly His Thr Arg Leu His Arg Met Thr Ser Ile Glu Arg Glu Glu
705                 710                 715                 720

Lys Glu Lys Val Lys Lys Glu Lys Lys Gln Glu Glu Glu Glu Thr
            725                 730                 735

Met Gln Gln Ala Thr Trp Val Lys Tyr Thr Phe Pro Val Lys His Gln
        740                 745                 750

Val Trp Lys Gln Lys Gly Glu Glu Tyr Arg Val Thr Gly Tyr Gly Gly
    755                 760                 765

Trp Ser Trp Ile Ser Lys Thr His Val Tyr Arg Phe Val Pro Lys Leu
770                 775                 780

Pro Gly Asn Thr Asn Val Asn Tyr Arg Lys Ser Leu Glu Gly Thr Lys
785                 790                 795                 800

Asn Asn Met Asp Glu Asn Met Asp Glu Ser Asp Lys Arg Lys Cys Ser
```

-continued

```
                805                 810                 815
Arg Ser Pro Lys Lys Ile Lys Ile Glu Pro Asp Ser Glu Lys Asp Glu
            820                 825                 830

Val Lys Gly Ser Asp Ala Ala Lys Gly Ala Asp Gln Asn Glu Met Asp
            835                 840                 845

Ile Ser Lys Ile Thr Glu Lys Lys Asp Gln Asp Val Lys Glu Leu Leu
850                 855                 860

Asp Ser Asp Ser Asp Lys Pro Cys Lys Glu Glu Pro Met Glu Val Asp
865                 870                 875                 880

Asp Asp Met Lys Thr Glu Ser His Val Asn Cys Gln Glu Ser Ser Gln
                885                 890                 895

Val Asp Val Val Asn Val Ser Glu Gly Phe His Leu Arg Thr Ser Tyr
            900                 905                 910

Lys Lys Lys Thr Lys Ser Ser Lys Leu Asp Gly Leu Leu Glu Arg Arg
            915                 920                 925

Ile Lys Gln Phe Thr Leu Glu Glu Lys Gln Arg Leu Glu Lys Ile Lys
            930                 935                 940

Leu Glu Gly Gly Ile Lys Gly Ile Gly Lys Thr Ser Thr Asn Ser Ser
945                 950                 955                 960

Lys Asn Leu Ser Glu Ser Pro Val Ile Thr Lys Ala Lys Glu Gly Cys
                965                 970                 975

Gln Ser Asp Ser Met Arg Gln Glu Gln Ser Pro Asn Ala Asn Asn Asp
            980                 985                 990

Gln Pro Glu Asp Leu Ile Gln Gly Cys Ser Gln Ser Asp Ser Ser Val
            995                 1000                1005

Leu Arg Met Ser Asp Pro Ser His Thr Thr Asn Lys Leu Tyr Pro
    1010                1015                1020

Lys Asp Arg Val Leu Asp Asp Val Ser Ile Arg Ser Pro Glu Thr
    1025                1030                1035

Lys Cys Pro Lys Gln Asn Ser Ile Glu Asn Asp Ile Glu Glu Lys
    1040                1045                1050

Val Ser Asp Leu Ala Ser Arg Gly Gln Glu Pro Thr Lys Ser Lys
    1055                1060                1065

Thr Lys Gly Asn Asp Phe Phe Ile Asp Asp Ser Lys Leu Ala Ser
    1070                1075                1080

Ala Asp Asp Ile Gly Thr Leu Ile Cys Lys Asn Lys Lys Pro Leu
    1085                1090                1095

Ile Gln Glu Glu Ser Asp Thr Ile Val Ser Ser Ser Lys Ser Ala
    1100                1105                1110

Leu His Ser Ser Val Pro Lys Ser Thr Asn Asp Arg Asp Ala Thr
    1115                1120                1125

Pro Leu Ser Arg Ala Met Asp Phe Glu Gly Lys Leu Gly Cys Asp
    1130                1135                1140

Ser Glu Ser Asn Ser Thr Leu Glu Asn Ser Ser Asp Thr Val Ser
    1145                1150                1155

Ile Gln Asp Ser Ser Glu Glu Asp Met Ile Val Gln Asn Ser Asn
    1160                1165                1170

Glu Ser Ile Ser Glu Gln Phe Arg Thr Arg Glu Gln Asp Val Glu
    1175                1180                1185

Val Leu Glu Pro Leu Lys Cys Glu Leu Val Ser Gly Glu Ser Thr
    1190                1195                1200

Gly Asn Cys Glu Asp Arg Leu Pro Val Lys Gly Thr Glu Ala Asn
    1205                1210                1215
```

-continued

Gly Lys Lys Pro Ser Gln Gln Lys Lys Leu Glu Glu Arg Pro Val
1220            1225            1230

Asn Lys Cys Ser Asp Gln Ile Lys Leu Lys Asn Thr Thr Asp Lys
1235            1240            1245

Lys Asn Asn Glu Asn Arg Glu Ser Glu Lys Lys Gly Gln Arg Thr
1250            1255            1260

Ser Thr Phe Gln Ile Asn Gly Lys Asp Asn Lys Pro Lys Ile Tyr
1265            1270            1275

Leu Lys Gly Glu Cys Leu Lys Glu Ile Ser Glu Ser Arg Val Val
1280            1285            1290

Ser Gly Asn Val Glu Pro Lys Val Asn Asn Ile Asn Lys Ile Ile
1295            1300            1305

Pro Glu Asn Asp Ile Lys Ser Leu Thr Val Lys Glu Ser Ala Ile
1310            1315            1320

Arg Pro Phe Ile Asn Gly Asp Val Ile Met Glu Asp Phe Asn Glu
1325            1330            1335

Arg Asn Ser Ser Glu Thr Lys Ser His Leu Leu Ser Ser Ser Asp
1340            1345            1350

Ala Glu Gly Asn Tyr Arg Asp Ser Leu Glu Thr Leu Pro Ser Thr
1355            1360            1365

Lys Glu Ser Asp Ser Thr Gln Thr Thr Thr Pro Ser Ala Ser Cys
1370            1375            1380

Pro Glu Ser Asn Ser Val Asn Gln Val Glu Asp Met Glu Ile Glu
1385            1390            1395

Thr Ser Glu Val Lys Lys Val Thr Ser Ser Pro Ile Thr Ser Glu
1400            1405            1410

Glu Glu Ser Asn Leu Ser Asn Asp Phe Ile Asp Glu Asn Gly Leu
1415            1420            1425

Pro Ile Asn Lys Asn Glu Asn Val Asn Gly Glu Ser Lys Arg Lys
1430            1435            1440

Thr Val Ile Thr Glu Val Thr Thr Met Thr Ser Thr Val Ala Thr
1445            1450            1455

Glu Ser Lys Thr Val Ile Lys Val Glu Lys Gly Asp Lys Gln Thr
1460            1465            1470

Val Val Ser Ser Thr Glu Asn Cys Ala Lys Ser Thr Val Thr Thr
1475            1480            1485

Thr Thr Thr Thr Val Thr Lys Leu Ser Thr Pro Ser Thr Gly Gly
1490            1495            1500

Ser Val Asp Ile Ile Ser Val Lys Glu Gln Ser Lys Thr Val Val
1505            1510            1515

Thr Thr Thr Val Thr Asp Ser Leu Thr Thr Thr Gly Gly Thr Leu
1520            1525            1530

Val Thr Ser Met Thr Val Ser Lys Glu Tyr Ser Thr Arg Asp Lys
1535            1540            1545

Val Lys Leu Met Lys Phe Ser Arg Pro Lys Lys Thr Arg Ser Gly
1550            1555            1560

Thr Ala Leu Pro Ser Tyr Arg Lys Phe Val Thr Lys Ser Thr Lys
1565            1570            1575

Lys Ser Ile Phe Val Leu Pro Asn Asp Asp Leu Lys Lys Leu Ala
1580            1585            1590

Arg Lys Gly Gly Ile Arg Glu Val Pro Tyr Phe Asn Tyr Asn Ala
1595            1600            1605

-continued

Lys Pro Ala Leu Asp Ile Trp Pro Tyr Pro Ser Pro Arg Pro Thr
1610                1615                1620

Phe Gly Ile Thr Trp Arg Tyr Arg Leu Gln Thr Val Lys Ser Leu
    1625                1630                1635

Ala Gly Val Ser Leu Met Leu Arg Leu Leu Trp Ala Ser Leu Arg
    1640                1645                1650

Trp Asp Asp Met Ala Ala Lys Val Pro Pro Gly Gly Gly Ser Thr
    1655                1660                1665

Arg Thr Glu Thr Ser Glu Thr Glu Ile Thr Thr Thr Glu Ile Ile
    1670                1675                1680

Lys Arg Arg Asp Val Gly Pro Tyr Gly Ile Arg Phe Glu Tyr Cys
    1685                1690                1695

Ile Arg Lys Ile Ile Cys Pro Ile Gly Val Pro Glu Thr Pro Lys
    1700                1705                1710

Glu Thr Pro Thr Pro Gln Arg Lys Gly Leu Arg Ser Ser Ala Leu
    1715                1720                1725

Arg Pro Lys Arg Pro Glu Thr Pro Lys Gln Thr Gly Pro Val Ile
    1730                1735                1740

Ile Glu Thr Trp Val Ala Glu Glu Leu Glu Leu Trp Glu Ile
    1745                1750                1755

Arg Ala Phe Ala Glu Arg Val Glu Lys Glu Lys Ala Gln Ala Val
    1760                1765                1770

Glu Gln Gln Ala Lys Lys Arg Leu Glu Gln Lys Pro Thr Val
    1775                1780                1785

Ile Ala Thr Ser Thr Thr Ser Pro Thr Ser Ser Thr Thr Ser Thr
    1790                1795                1800

Ile Ser Pro Ala Gln Lys Val Met Val Ala Pro Ile Ser Gly Ser
    1805                1810                1815

Val Thr Thr Gly Thr Lys Met Val Leu Thr Thr Lys Val Gly Ser
    1820                1825                1830

Pro Ala Thr Val Thr Phe Gln Gln Asn Lys Asn Phe His Gln Thr
    1835                1840                1845

Phe Ala Thr Trp Val Lys Gln Gly Gln Ser Asn Ser Gly Val Val
    1850                1855                1860

Gln Val Gln Gln Lys Val Leu Gly Ile Ile Pro Ser Ser Thr Gly
    1865                1870                1875

Thr Ser Gln Gln Thr Phe Thr Ser Phe Gln Pro Arg Thr Ala Thr
    1880                1885                1890

Val Thr Ile Arg Pro Asn Thr Ser Gly Ser Gly Gly Thr Thr Ser
    1895                1900                1905

Asn Ser Gln Val Ile Thr Gly Pro Gln Ile Arg Pro Gly Met Thr
    1910                1915                1920

Val Ile Arg Thr Pro Leu Gln Gln Ser Thr Leu Gly Lys Ala Ile
    1925                1930                1935

Ile Arg Thr Pro Val Met Val Gln Pro Gly Ala Pro Gln Gln Val
    1940                1945                1950

Met Thr Gln Ile Ile Arg Gly Gln Pro Val Ser Thr Ala Val Ser
    1955                1960                1965

Ala Pro Asn Thr Val Ser Ser Thr Pro Gly Gln Lys Ser Leu Thr
    1970                1975                1980

Ser Ala Thr Ser Thr Ser Asn Ile Gln Ser Ser Ala Ser Gln Pro
    1985                1990                1995

Pro Arg Pro Gln Gln Gly Gln Val Lys Leu Thr Met Ala Gln Leu

```
            2000                2005                2010
Thr Gln Leu Thr Gln Gly His Gly Gly Asn Gln Gly Leu Thr Val
            2015                2020                2025

Val Ile Gln Gly Gln Gly Gln Thr Thr Gly Gln Leu Gln Leu Ile
            2030                2035                2040

Pro Gln Gly Val Thr Val Leu Pro Gly Pro Gly Gln Gln Leu Met
            2045                2050                2055

Gln Ala Ala Met Pro Asn Gly Thr Val Gln Arg Phe Leu Phe Thr
            2060                2065                2070

Pro Leu Ala Thr Thr Ala Thr Thr Ala Ser Thr Thr Thr Thr Thr
            2075                2080                2085

Val Ser Thr Thr Ala Ala Gly Thr Gly Glu Gln Arg Gln Ser Lys
            2090                2095                2100

Leu Ser Pro Gln Met Gln Val His Gln Asp Lys Thr Leu Pro Pro
            2105                2110                2115

Ala Gln Ser Ser Ser Val Gly Pro Ala Lys Ala Gln Pro Gln Thr
            2120                2125                2130

Ala Gln Pro Ser Ala Arg Pro Gln Pro Gln Thr Gln Pro Gln Ser
            2135                2140                2145

Pro Ala Gln Pro Glu Val Gln Thr Gln Pro Glu Val Gln Thr Gln
            2150                2155                2160

Thr Thr Val Ser Ser His Val Pro Ser Glu Ala Gln Pro Thr His
            2165                2170                2175

Ala Gln Ser Ser Lys Pro Val Ala Ala Gln Ser Gln Pro Gln
            2180                2185                2190

Ser Asn Val Gln Gly Gln Ser Pro Val Arg Val Gln Ser Pro Ser
            2195                2200                2205

Gln Thr Arg Ile Arg Pro Ser Thr Pro Ser Gln Leu Ser Pro Gly
            2210                2215                2220

Gln Gln Ser Gln Val Gln Thr Thr Thr Ser Gln Pro Ile Pro Ile
            2225                2230                2235

Gln Pro His Thr Ser Leu Gln Ile Pro Ser Gln Gly Gln Pro Gln
            2240                2245                2250

Ser Gln Pro Gln Val Gln Ser Ser Thr Gln Thr Leu Ser Ser Gly
            2255                2260                2265

Gln Thr Leu Asn Gln Val Ser Val Ser Ser Pro Ser Arg Pro Gln
            2270                2275                2280

Leu Gln Ile Gln Gln Pro Gln Pro Gln Val Ile Ala Val Pro Gln
            2285                2290                2295

Leu Gln Gln Gln Val Gln Val Leu Ser Gln Ile Gln Ser Gln Val
            2300                2305                2310

Val Ala Gln Ile Gln Ala Gln Gln Ser Gly Val Pro Gln Gln Ile
            2315                2320                2325

Lys Leu Gln Leu Pro Ile Gln Ile Gln Gln Ser Ser Ala Val Gln
            2330                2335                2340

Thr His Gln Ile Gln Asn Val Val Thr Val Gln Ala Ala Ser Val
            2345                2350                2355

Gln Glu Gln Leu Gln Arg Val Gln Gln Leu Arg Asp Gln Gln Gln
            2360                2365                2370

Lys Lys Lys Gln Gln Gln Ile Glu Ile Lys Arg Glu His Thr Leu
            2375                2380                2385

Gln Ala Ser Asn Gln Ser Glu Ile Ile Gln Lys Gln Val Val Met
            2390                2395                2400
```

Lys His Asn Ala Val Ile Glu His Leu Lys Gln Lys Lys Ser Met
2405                2410                2415

Thr Pro Ala Glu Arg Glu Glu Asn Gln Arg Met Ile Val Cys Asn
2420                2425                2430

Gln Val Met Lys Tyr Ile Leu Asp Lys Ile Asp Lys Glu Glu Lys
2435                2440                2445

Gln Ala Ala Lys Lys Arg Lys Arg Glu Glu Ser Val Glu Gln Lys
2450                2455                2460

Arg Ser Lys Gln Asn Ala Thr Lys Leu Ser Ala Leu Leu Phe Lys
2465                2470                2475

His Lys Glu Gln Leu Arg Ala Glu Ile Leu Lys Lys Arg Ala Leu
2480                2485                2490

Leu Asp Lys Asp Leu Gln Ile Glu Val Gln Glu Glu Leu Lys Arg
2495                2500                2505

Asp Leu Lys Ile Lys Lys Glu Lys Asp Leu Met Gln Leu Ala Gln
2510                2515                2520

Ala Thr Ala Val Ala Ala Pro Cys Pro Pro Val Thr Pro Val Leu
2525                2530                2535

Pro Ala Pro Pro Ala Pro Pro Pro Ser Pro Pro Pro Pro Pro Gly
2540                2545                2550

Val Gln His Thr Gly Leu Leu Ser Thr Pro Thr Leu Pro Val Ala
2555                2560                2565

Ser Gln Lys Arg Lys Arg Glu Glu Lys Asp Ser Ser Ser Ser Lys
2570                2575                2580

Ser Lys Lys Lys Lys Met Ile Ser Thr Thr Ser Lys Glu Thr Lys
2585                2590                2595

Lys Asp Thr Lys Leu Tyr Cys Ile Cys Lys Thr Pro Tyr Asp Glu
2600                2605                2610

Ser Lys Phe Tyr Ile Gly Cys Asp Arg Cys Gln Asn Trp Tyr His
2615                2620                2625

Gly Arg Cys Val Gly Ile Leu Gln Ser Glu Ala Glu Leu Ile Asp
2630                2635                2640

Glu Tyr Val Cys Pro Gln Cys Gln Ser Thr Glu Asp Ala Met Thr
2645                2650                2655

Val Leu Thr Pro Leu Thr Glu Lys Asp Tyr Glu Gly Leu Lys Arg
2660                2665                2670

Val Leu Arg Ser Leu Gln Ala His Lys Met Ala Trp Pro Phe Leu
2675                2680                2685

Glu Pro Val Asp Pro Asn Asp Ala Pro Asp Tyr Tyr Gly Val Ile
2690                2695                2700

Lys Glu Pro Met Asp Leu Ala Thr Met Glu Glu Arg Val Gln Arg
2705                2710                2715

Arg Tyr Tyr Glu Lys Leu Thr Glu Phe Val Ala Asp Met Thr Lys
2720                2725                2730

Ile Phe Asp Asn Cys Arg Tyr Tyr Asn Pro Ser Asp Ser Pro Phe
2735                2740                2745

Tyr Gln Cys Ala Glu Val Leu Glu Ser Phe Phe Val Gln Lys Leu
2750                2755                2760

Lys Gly Phe Lys Ala Ser Arg Ser His Asn Asn Lys Leu Gln Ser
2765                2770                2775

Thr Ala Ser
2780

```
<210> SEQ ID NO 3
<211> LENGTH: 29
<212> TYPE: DNA
<213> ORGANISM: Artificial Sequence
<220> FEATURE:
<223> OTHER INFORMATION: BPTF shRNA1

<400> SEQUENCE: 3
tggctgtgat cggtgtcaga attggtacc                                    29

<210> SEQ ID NO 4
<211> LENGTH: 29
<212> TYPE: DNA
<213> ORGANISM: Artificial Sequence
<220> FEATURE:
<223> OTHER INFORMATION: BPTF shRNA2

<400> SEQUENCE: 4
ggtgatgaag cataatgctg taatagaac                                    29

<210> SEQ ID NO 5
<211> LENGTH: 21
<212> TYPE: DNA
<213> ORGANISM: Artificial Sequence
<220> FEATURE:
<223> OTHER INFORMATION: BPTF shRNA3

<400> SEQUENCE: 5
atttagattc atcataaggc g                                            21
```